United States Patent
Altschuler

(10) Patent No.: US 11,878,090 B2
(45) Date of Patent: *Jan. 23, 2024

(54) SOLID SUBSTRATES FOR PROMOTING CELL AND TISSUE GROWTH

(71) Applicant: CARTIHEAL (2009) LTD., Kfar Saba (IL)

(72) Inventor: Nir Altschuler, Tsur Yitskhak (IL)

(73) Assignee: CARTIHEAL (2009) LTD., Kfar Saba (IL)

( * ) Notice: Subject to any disclaimer, the term of this patent is extended or adjusted under 35 U.S.C. 154(b) by 113 days.

This patent is subject to a terminal disclaimer.

(21) Appl. No.: 17/471,760

(22) Filed: Sep. 10, 2021

(65) Prior Publication Data
US 2021/0402059 A1 Dec. 30, 2021

Related U.S. Application Data

(63) Continuation of application No. 16/837,232, filed on Apr. 1, 2020, now Pat. No. 11,116,873, which is a
(Continued)

(51) Int. Cl.
| | | |
|---|---|---|
| A61L 27/36 | (2006.01) | |
| A61L 27/52 | (2006.01) | |
| A61L 27/54 | (2006.01) | |
| A61L 27/56 | (2006.01) | |
| A61L 27/12 | (2006.01) | |

(Continued)

(52) U.S. Cl.
CPC ............ *A61L 27/3608* (2013.01); *A61F 2/28* (2013.01); *A61F 2/30* (2013.01); *A61F 2/30756* (2013.01); *A61L 27/12* (2013.01); *A61L 27/20* (2013.01); *A61L 27/3604* (2013.01); *A61L 27/365* (2013.01); *A61L 27/3637* (2013.01); *A61L 27/3654* (2013.01); *A61L 27/3834* (2013.01); *A61L 27/40* (2013.01); *A61L 27/50* (2013.01); *A61L 27/52* (2013.01); *A61L 27/54* (2013.01); *A61L 27/56* (2013.01); *C01B 25/32* (2013.01); *C01F 11/18* (2013.01); *G01N 1/00* (2013.01); *A61F 2230/0006* (2013.01); *A61F 2230/0065* (2013.01); *A61F 2230/0067* (2013.01); *A61F 2230/0069* (2013.01); *A61F 2230/0071* (2013.01); *A61F 2230/0086* (2013.01); *A61L 2300/112* (2013.01); *A61L 2300/41* (2013.01); *A61L 2300/412* (2013.01); *A61L 2300/414* (2013.01); *A61L 2300/426* (2013.01); *A61L 2430/02* (2013.01); *A61L 2430/06* (2013.01); *C01P 2006/90* (2013.01)

(58) Field of Classification Search
CPC ...... A61L 27/3608; A61L 27/12; A61L 27/20; A61L 27/3604; A61L 27/3637; A61L 27/365; A61L 27/3654; A61L 27/3834; A61L 27/40; A61L 27/50; A61L 27/52; A61L 27/54; A61L 27/56; A61L 2300/112; A61L 2300/41; A61L 2300/412; A61L 2300/414; A61L 2300/426; A61L 2430/02; A61L 2430/06; A61F 2/28; A61F 2/30; A61F 2/30756; A61F 2230/0006; A61F 2230/0065; A61F 2230/0067; A61F 2230/0069; A61F 2230/0071; A61F 2230/0086; C01B 25/32; C01F 11/18; G01N 1/00; C01P 2006/90; A61P 7/00; A61P 15/00; A61P 17/06; A61P 19/02; A61P 19/08; A61P 27/02; A61P 31/00; A61P 33/00; A61P 35/00; A61P 37/02; A61P 43/00

See application file for complete search history.

(56) References Cited

U.S. PATENT DOCUMENTS 7,166,133 B2    1/2007  Evans et al.
7,758,643 B2    7/2010  Stone et al.
(Continued)

FOREIGN PATENT DOCUMENTS

CN    102665604 A    9/2012
CN      1386478 A    8/2014
(Continued)

OTHER PUBLICATIONS

Office action from CNIPA dated Aug. 25, 2021, for CN patent Application No. 202010250265.2.
(Continued)

*Primary Examiner* — Robert S Cabral
(74) *Attorney, Agent, or Firm* — Sterne, Kessler, Goldstein & Fox P.L.L.C.

(57) ABSTRACT

This invention provides solid substrates for promoting cell or tissue growth or restored function, which solid substrate is characterized by a specific fluid uptake capacity value of at least 75%, which specific fluid uptake capacity value is determined by establishing a spontaneous fluid uptake value divided by a total fluid uptake value. This invention also provides solid substrates for promoting cell or tissue growth or restored function, which solid substrate is characterized by having a contact angle value of less than 60 degrees, when in contact with a fluid. This invention also provides solid substrates for promoting cell or tissue growth or restored function, which said substrate is characterized by a substantial surface roughness (Ra) as measured by scanning electron microscopy or atomic force microscopy. The invention also provides for processes for selection of an optimized coral-based solid substrate for promoting cell or tissue growth or restored function and applications of the same.

22 Claims, 21 Drawing Sheets

Related U.S. Application Data continuation of application No. 14/767,428, filed as application No. PCT/IL2014/050141 on Feb. 10, 2014, now Pat. No. 10,806,823.

(60) Provisional application No. 61/773,219, filed on Mar. 6, 2013, provisional application No. 61/773,228, filed on Mar. 6, 2013, provisional application No. 61/763,981, filed on Feb. 13, 2013, provisional application No. 61/764,467, filed on Feb. 13, 2013, provisional application No. 61/763,985, filed on Feb. 13, 2013, provisional application No. 61/764,496, filed on Feb. 13, 2013.

(51) Int. Cl.
| | |
|---|---|
| A61L 27/20 | (2006.01) |
| A61L 27/40 | (2006.01) |
| C01B 25/32 | (2006.01) |
| C01F 11/18 | (2006.01) |
| G01N 1/00 | (2006.01) |
| A61L 27/50 | (2006.01) |
| A61F 2/28 | (2006.01) |
| A61F 2/30 | (2006.01) |
| A61L 27/38 | (2006.01) |

(56) References Cited

U.S. PATENT DOCUMENTS

| | | |
|---|---|---|
| 7,887,598 B2 | 2/2011 | Evans et al. |
| 8,790,681 B2 | 7/2014 | Altschuler et al. |
| 8,802,115 B2 | 8/2014 | Altschuler et al. |
| 8,808,725 B2 | 8/2014 | Altschuler et al. |
| 8,932,581 B2 | 1/2015 | Vago |
| 9,770,531 B2 | 9/2017 | Altschuler |
| 10,046,084 B2 | 8/2018 | Altschuler et al. |
| 10,080,818 B2 | 9/2018 | Altschuler et al. |
| 10,271,938 B2 | 4/2019 | Altschuler |
| 10,342,897 B2 | 7/2019 | Altschuler |
| 10,702,627 B2 | 7/2020 | Altschuler et al. |
| 10,799,251 B2 | 10/2020 | Altschuler et al. |
| 10,806,823 B2 | 10/2020 | Altschuler |
| 11,116,873 B2 | 9/2021 | Altschuler |
| 2003/0236573 A1 | 12/2003 | Evans et al. |
| 2008/0249632 A1 | 10/2008 | Stone et al. |
| 2009/0110710 A1 | 4/2009 | Evans et al. |
| 2009/0123547 A1 | 5/2009 | Hill et al. |
| 2011/0256228 A1 | 10/2011 | Altschuler et al. |
| 2012/0177702 A1 | 7/2012 | Altschuler et al. |
| 2012/0189669 A1 | 7/2012 | Altschuler et al. |
| 2014/0287017 A1 | 9/2014 | Altschuler et al. |
| 2015/0056262 A1 | 2/2015 | Altschuler et al. |
| 2015/0134065 A1 | 5/2015 | Altschuler |
| 2015/0147397 A1 | 5/2015 | Altschuler |
| 2015/0289889 A1 | 10/2015 | Altschuler et al. |
| 2015/0374880 A1 | 12/2015 | Altschuler |
| 2016/0175098 A1 | 6/2016 | Altschuler et al. |
| 2016/0175480 A1 | 6/2016 | Altschuler et al. |
| 2016/0184477 A1 | 6/2016 | Altschuler |

FOREIGN PATENT DOCUMENTS

| | | |
|---|---|---|
| WO | WO 2009/066283 A2 | 5/2009 |
| WO | WO 2010/058400 A1 | 5/2010 |
| WO | WO 2010/146574 A1 | 12/2010 |
| WO | WO 2010/146575 A2 | 12/2010 |
| WO | WO 2014/072982 A2 | 12/2010 |
| WO | WO 2012/036286 A1 | 3/2012 |
| WO | WO 2012/100100 A2 | 7/2012 |
| WO | WO 2013/150537 A1 | 10/2013 |
| WO | WO 2014/125477 A1 | 10/2013 |
| WO | WO 2010/058400 A1 | 11/2013 |
| WO | WO 2013/171736 A1 | 11/2013 |
| WO | WO 2016/178226 A1 | 5/2014 |
| WO | WO 2014/125477 A1 | 8/2014 |

OTHER PUBLICATIONS

Second Office Action from CNIPA dated Mar. 28, 2022 for CN Patent Appl. No. 202010250265.2.
"Principles and Techniques of Tissue Engineering," Jin Yan (main editor), Fourth Military Medical University Press, p. 5, published Jun. 30, 2004.
"Mechanical Experiments of Indoor Rocks," Fu Xiaomin and Deng Ronggui, ed., Southwest Jiaotong University Press, p. 30, published Apr. 30, 2012.
International Search Report (ISR) for PCT/IL2014/050141; I.A. fd dated Feb. 10, 2014, dated May 26, 2014 from the European Patent Office, Rijswijk, Netherlands.
International Preliminary Report on Patentability (Chapter II of the Patent Cooperation Treaty) for PCT/IL2014/050141; I.A. fd dated Feb. 10, 2014, completed May 12, 2015, by the European Patent Office, Rijswijk, Netherlands.
Vago, R et al., "Hard tissue remodeling using biofabricated coralline biomaterials," J Biochem Biophys Methods 50(2-3):253-259 (Jan. 2002), Elsevier/North-Holland Biomedical Press, Amsterdam, Netherlands.
Xu, Y. et al., "Hydrothermal conversion of coral into hydroxyapatite," Materials Characterization 47:83-87 (Aug. 2001), Elsevier, Amsterdam, Netherlands.
Ben-Nissan, B. et al., "Morphology of sol-gel derived nano-coated coralline hydroxyapatite," Biomaterials 25(20):4971-4975 (Sep. 2004), Elsevier Science Publishers BV, Amsterdam, Netherlands.
Excerpted file history, U.S. Appl. No. 14/983,890, amendment and reply filed Aug. 30, 2017, non-final rejection dated May 30, 2017 and preliminary amendment filed Dec. 30, 2015, downloaded Nov. 7, 2017, US Patent and Trademark Office, Alexandria, VA.
Excerpted file history, U.S. Appl. No. 14/767,432, issue notification dated Sept. 6, 2017, notice of allowance dated May 22, 2017, examiner-initiated interview summary dated May 22, 2017, third preliminary amendment filed May 109, 2017, reply to restriction/election of species requirement filed May 1, 2017, 2nd preliminary amendment filed May 1, 2017, restriction/election of species requirement dated Feb. 24, 2017, and first preliminary amendment, filed Nov. 11, 2015, downloaded Nov. 7, 2017, US Patent and Trademark Office, Alexandria, VA.
"Notice of Reasons for Rejection" (Translation) for JP Patent Appl. No. 2015-557567, dated Sep. 26, 2017, by the Japan Patent Office, Tokyo, Japan.
Yanagisawa, I., "The effect of 'wettability' of the biomaterials on culture cells," Nihon Univ Dent J, 1988, vol. 62, pp. 8-19, Nihon University School of Dentistry, Chiyoda, Japan.
Wu, Y-C, "A comparative study of the physical and mechanical properties of three natural corals based on the criteria for bone-tissue engineering scaffolds," J Mater Sci: Mater Med (Jun. 2009) 20:1273-1280 (published online Mar. 9, 2009), Springer, Norwell, MA.
Volpi, N, "Adsorption of glycosaminoglycans onto coral—a new possible implant biomaterials for regeneration therapy," Biomaterials 20:1359-1363 (Aug. 1999), Elsevier, Amsterdam, Netherlands.
Vago, R, "Beyond the skeleton—nidarian biomaterials as bioactive extracellular microenvironments for tissue engineering," Organigenesis 4:1, 18-22 (Jan.-Feb.-Mar. 2008), Landes Bioscience, Georgetown, TX.
Supplementary Search, for CN Patent Appl. No. 201480021035.1, dated Sep. 29, 2017, by The State Intellectual Property Office of the People's Republic of China, Beijing, CN.
"The First Office Action" for CN Patent Appl. No. 201480021035.1, dated Sep. 28, 2016, by The State Intellectual Property Office of the People's Republic of China, Beijing, CN.
"The Second Office Action" for CN Patent Appl. No. 201480021035.1, dated May 12, 2017, by The State Intellectual Property Office of the People's Republic of China, Beijing, CN.

(56) References Cited

OTHER PUBLICATIONS

"The Third Office Action" for CN Patent Appl. No. 201480021035.1, dated Oct. 25, 2017, by The State Intellectual Property Office of the People's Republic of China, Beijing, CN.

Lin, S. et al., "Preparation and Characteristics of Digital Coral Hydroxyapatite Artificial Bone," Orthopedic J of China 18(24):2082-2086 (2010) (7 page translation), China Disabled Persons Rehabilitation Assoc, Tai'an City, Shandong Province, China.

Wu, Q., ed., "Modern digital medical equipment and key technology, the first edition," The Medicine Science and Technology Press of China, 2008, Beijing, Cn, ISBN 978-7-5067-3844-6, pp. 301-303.

Excerpted file history, U.S. Appl. No. 14/983,890, final Office action dated Dec. 12, 2017, The United States Patent and Trademark Office, Alexandria, VA.

Excerpted file history, U.S. Appl. No. 14/983,890, Final rejection (dated Jul. 2, 2018); RCE and amendment and reply (filed Jun. 11, 2018), The United States Patent and Trademark Office, Alexandria, VA.

Excerpted file history, U.S. Appl. No. 14/983,890, Notice of Abandonment (dated Jan. 14, 2019); The United States Patent and Trademark Office, Alexandria, VA.

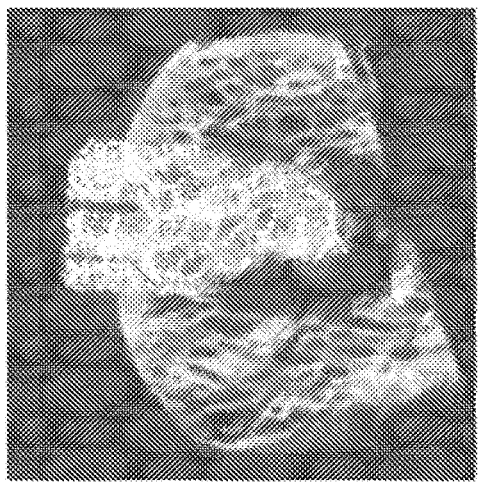
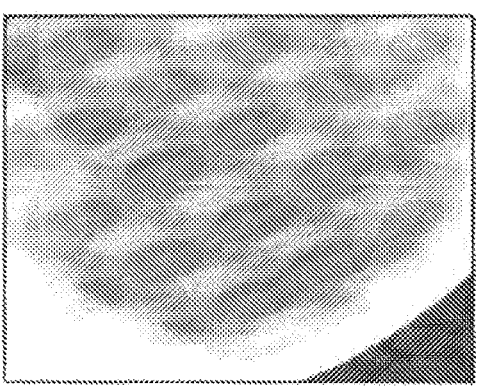
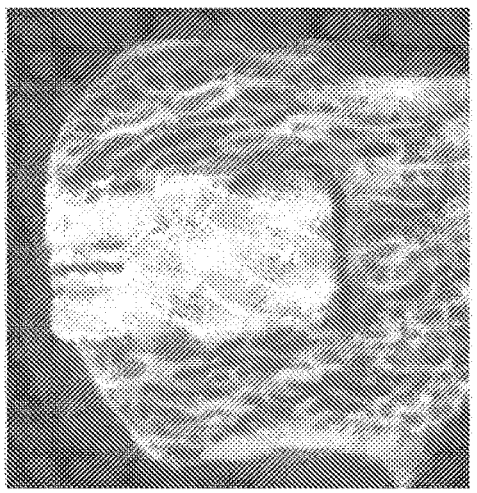
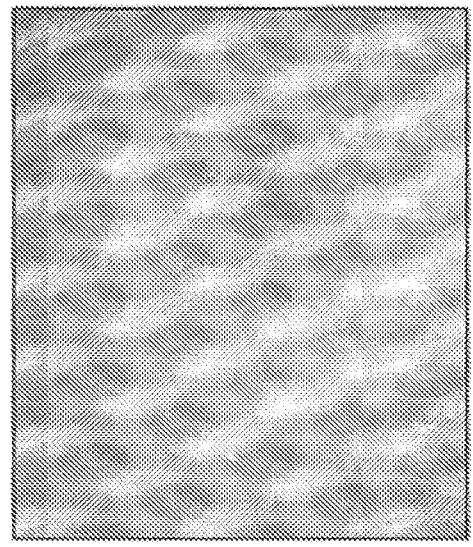

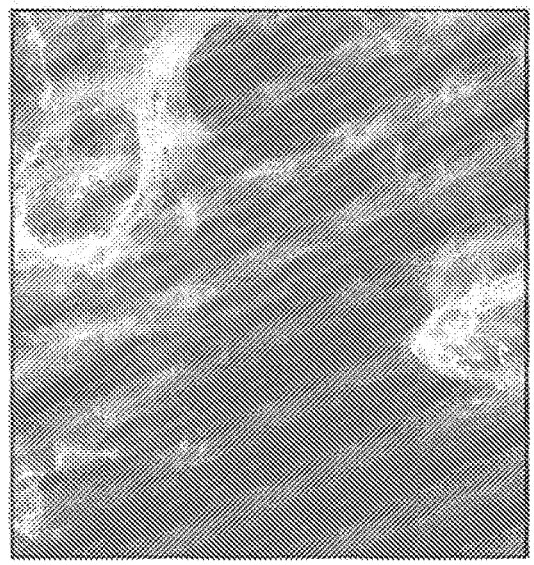
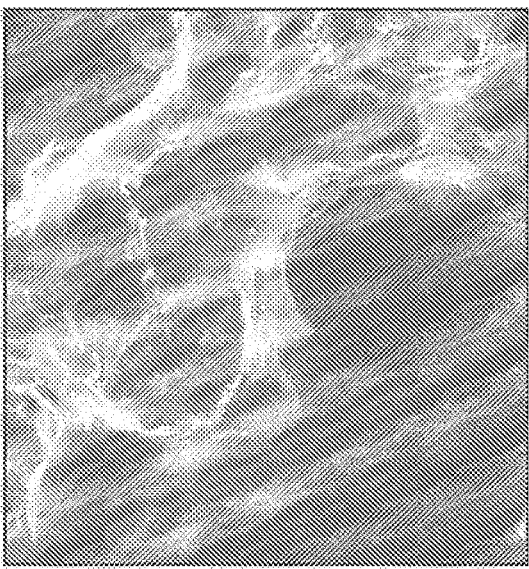

Fig.23C
Before Purification
R48
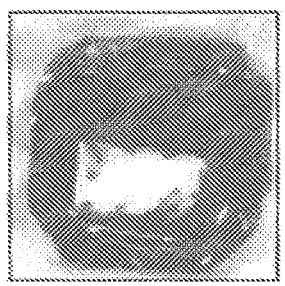
R91
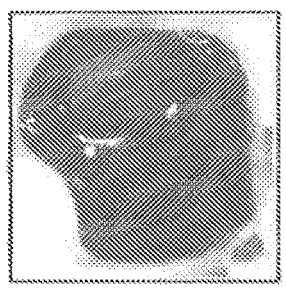
Fig.23D
Before Purification
R48
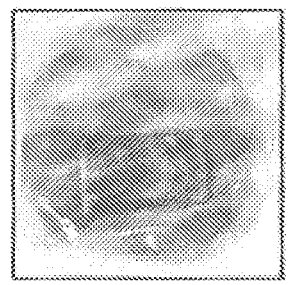
R91
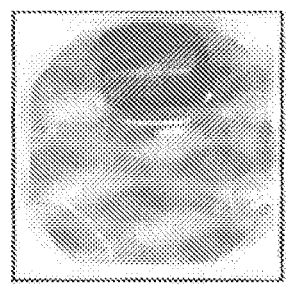
Fig.23E
After purification
(After Ethanol step)
R48
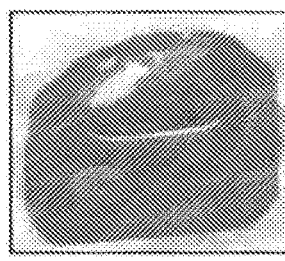
R91
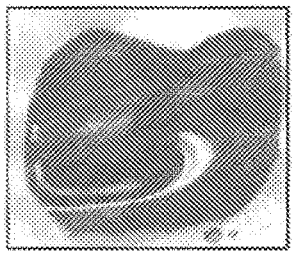
Fig.23F
After purification
(After Ethanol step)
R48
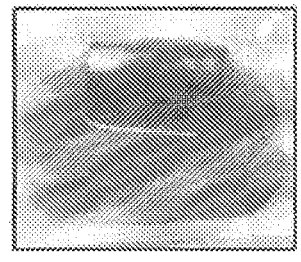
R91
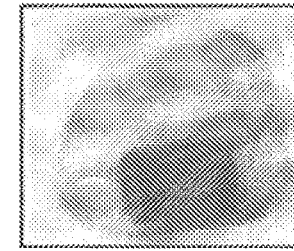

SOLID SUBSTRATES FOR PROMOTING CELL AND TISSUE GROWTH

CROSS REFERENCE TO RELATED APPLICATIONS

U.S. application Ser. No. 14/767,428, U.S. Provisional Application No. 61/763,981, U.S. Provisional Application No. 61/763,985, U.S. Provisional Application No. 61/764,467, and U.S. Provisional Application No. 61/764,496, all of which were filed Feb. 13, 2013, as well as U.S. Provisional Application No. 61/773,219 and U.S. Provisional Application No. 61/773,228, both of which were filed Mar. 6, 2013 are all hereby incorporated by reference herein in their entirety.

BACKGROUND OF THE INVENTION

Tissue growth, regeneration and repair are often necessary to restore function and reconstruct the morphology of the tissue, for example, as a result of exposure to trauma, neoplasia, abnormal tissue growth, aging, and others.

Synthetic materials have also used as a substrate for promoting ex-vivo tissue assembly and repair, and similarly for restoring and reconstructing different tissues, for example for bone, for many years, with mixed success. Another possibility is autologous tissue grafting, although the supply of autologous tissue is limited and its collection may be painful, with the risk of infection, hemorrhage, cosmetic disability, nerve damage, and loss of function. In addition, significant morbidity is associated with autograft harvest sites. These problems may be overcome by engineering tissue using solid substrates made of synthetic or natural biomaterials that promote the adhesion, migration, proliferation, and differentiation of stem cells, for example, mesenchymal stem cells (MSCs).

Many diseases and conditions whose treatment is sought would benefit from the ability to promote cell and tissue growth in a site-specific manner, promoting growth and incorporation of new tissue within a damaged or diseased site.

In bone and cartilage applications, the immediate microenvironment and the three-dimensional (3D) organization are important factors in differentiation in general and particularly in chondrogenic and osteogenic differentiation.

Some bone tissue engineering scaffolds consists of natural polymers, such as collagen, alginate, hyaluronic acid, and chitosan. Natural materials offer the advantages of specific cell interaction, easy seeding of cells because of their hydrophilic interactions, low toxicity and low chronic inflammatory response. However, these scaffolds often are mechanically unstable and do not readily contribute to the creation of tissue structures with a specific predefined shape for transplantation. To obtain mechanical strength, chemical modification is required, which may lead to toxicity.

Defects and degeneration of the articular cartilage surfaces of joints causes pain and stiffness. Damage to cartilage which protects joints can result from either physical injury as a result of trauma, sports or repetitive stresses (e.g., osteochondral fracture, secondary damage due to cruciate ligament injury) or from disease (e.g. osteoarthritis, rheumatoid arthritis, aseptic necrosis, osteochondritis dissecans).

Osteoarthritis (OA) results from general wear and tear of joints, most notably hip and knee joints. Osteoarthritis is common in the elderly but, in fact, by age 40 most individuals have some osteoarthritic changes in their weight bearing joints. Another emerging trend increasing the prevalence of osteoarthritis is the rise in obesity. The CDC estimates that 30% of American adults (or 60 million people) are obese. Obese adults are 4 times more likely to develop knee OA than normal weight adults Rheumatoid arthritis is an inflammatory condition which results in the destruction of cartilage. It is thought to be, at least in part, an autoimmune disease with sufferers having a genetic predisposition to the disease.

Orthopedic prevention and repair of damaged joints is a significant burden on the medical profession both in terms of expense and time spent treating patients. In part, this is because cartilage does not posses the capacity for self-repair. Attempts to re-grow hyaline cartilage for repair of cartilage defects remain unsuccessful. Orthopedic surgery is available in order to repair defects and prevent articular damage in an effort to forestall serious degenerative changes in a joint. The use of surgical techniques often requires the removal and donation of healthy tissue to replace the damaged or diseased tissue. Techniques utilizing donated tissue from autografts, allografts, or xenografts are wholly unsatisfactory as autografts add additional trauma to a subject and allografts and xenografts are limited by immunological reactivity to the host subject and possible transfer of infective agents. Surgical attempts to utilize materials other than human or animal tissue for cartilage regeneration have been unsuccessful.

More broadly, there is also a lack of appropriate solid substrates for other applications in cell and tissue growth, expansion and modeling, as well.

An ideal material which restores tissue function and facilitates reconstruction of the morphology of such tissue is as yet, lacking.

SUMMARY OF THE INVENTION

In some embodiments, the present invention provides optimized solid substrates for promoting cell or tissue growth or restored function. In some embodiments, the invention provides a process for the selection of an optimized marine organism skeletal derivative-based solid substrate for promoting cell or tissue growth or restored function, comprising establishing a specific fluid uptake capacity value for the marine organism skeletal derivative-based solid material, and selecting a marine organism skeletal derivative-based solid material characterized by a specific fluid uptake capacity value of at least 75%.

In some embodiments, the invention provides a solid substrate for promoting cell or tissue growth or restored function, which solid substrate comprises a optimized marine organism skeletal derivative and is characterized by a specific fluid uptake capacity value of at least 75%, which specific fluid uptake capacity value is determined by establishing a spontaneous fluid uptake value divided by a total fluid uptake value and which solid substrate has been exposed to certain post-isolation purification and/or processing procedures.

In some embodiments, the solid substrate in accordance with this invention and obtained via the processes of this invention is characterized by a specific fluid uptake capacity value of at least 80%, and in some embodiments, the solid substrate in accordance with this invention and obtained via the processes of this invention is characterized by a specific fluid uptake capacity value of at least 85%, and in some embodiments, the solid substrate in accordance with this invention and obtained via the processes of this invention is characterized by a specific fluid uptake capacity value of at least 90%, and in some embodiments, the solid substrate in accordance with this invention and obtained via the processes of this invention is characterized by a specific fluid uptake capacity value of at least 95%, and in some embodiments, the solid substrate in accordance with this invention and obtained via the processes of this invention is characterized by a specific fluid uptake capacity value of at least 97%. In some embodiments, the solid substrate in accordance with this invention and obtained via the processes of this invention is characterized by a specific fluid uptake capacity value of from 75-100%.

In some embodiments, the term "a specific fluid uptake capacity value" is also referred to herein as "SFUC" or "SWC", all of which are to be understood to be interchangeable.

In some embodiments, a specific fluid uptake capacity value of this invention is determined using an apparatus, which is automated. In some aspects, and as exemplified and further described hereinunder, assessment of the specific fluid uptake capacity value of various samples may be simultaneously or sequentially assessed, as part of an automated scaled-up process appropriate for commercial production. In some aspects, such apparatus may further provide for the individual selection and transport of samples having desired characteristics.

In some embodiments, the invention provides a solid substrate for promoting cell or tissue growth or restored function, or a process for obtaining same, which solid substrate comprises a organism skeletal derivative and is characterized by having a contact angle value of less than 60 degrees, when in contact with a fluid.

As the skilled artisan will appreciate, a contact angle may be determined as described and exemplified herein, using standard methodology and equipment, for example, via goniometry. In some embodiments, such methods may make use of processes as described in P. A. Thomson, W. B. Brinckerhoff, M. O. Robbins, in: K. L. Mittal (Ed.), Contact Angle Wettability and Adhesion, VSP, Utrecht, 1993, pp. 139-158; E. L. Decker, S. Garof, Langmuir 13 (1997) 6321; and M. G. Orkoula et al.: Colloids and Surfaces A: Physicochem. Eng. Aspects 157 (1999) 333-340; Hiemenz, P. C.; Rajagopalan, R. Principles of Colloid and Surface Chemistry, 1997, 3rd Ed., Marcel Dekker, Inc; Applied Colloid and Surface Chemistry Chapter 2: Surface Tension and wetting, by Richard Pashley, Marilyn Karaman, 2004, John Wiley and sons, all of which are hereby incorporated in their entirety.

In some embodiments, the invention provides a solid substrate for promoting cell or tissue growth or restored function, or a process for obtaining same, which solid substrate is characterized by substantial surface roughness (Ra) as measured by scanning electron microscopy or atomic force microscopy.

In some embodiments, the coral or coral derivative is aragonite, calcite, mixtures thereof, or other polymorphs of the same.

In some embodiments the structure composition of the coral or coral derivative is determined by X-ray diffraction (XRD) or Feigl solution positive staining.

In some embodiments, the solid substrate is isolated from a *Porites* species, a *Goniopora*, a *Millepora* species or an *Acropora* species.

In some embodiments, the solid substrate is isolated from a barnacle or mollusk. In some embodiments, the solid substrate is comprised of nacre.

In some embodiments, the invention provides a kit comprising one or more solid substrates as herein described. In some embodiments, the kit will comprise a series of solid substrates characterized by a specific fluid uptake capacity value of at least 75% and/or produced by a process of this invention, where the marine organism skeletal derivative-based solid materials in the kit have a specific fluid uptake capacity value of from 75% to 99%, and in some embodiments, the kit contains a series of solid substrates characterized by a specific fluid uptake capacity value of from 80% to 99%, and in some embodiments, the kit contains a series of solid substrates characterized by a specific fluid uptake capacity value of from 85% to 99%, and in some embodiments, the kit contains a series of solid substrates characterized by a specific fluid uptake capacity value of from 90% to 99%, and in some embodiments, the kit contains a series of solid substrates characterized by a specific fluid uptake capacity value of from 95% to 99% or, in other embodiments, from 95% to 100%.

In another embodiment, the invention provides a process for selection of an optimized marine organism skeletal derivative-based solid substrate for promoting cell or tissue growth or restored function, said process comprising:

isolating a marine organism skeletal derivative-based solid material;

establishing a specific fluid uptake capacity value of said marine organism skeletal derivative-based solid material, which specific fluid uptake capacity value is determined by establishing a spontaneous fluid uptake value divided by a total fluid uptake value; and selecting a marine organism skeletal derivative-based solid material characterized by a specific fluid uptake capacity value of at least 75%.

In some embodiments, according to this aspect, the process further comprises the step of contacting said marine organism skeletal derivative-based solid material with a fluid for from 0.1-15 minutes to promote spontaneous fluid uptake of said fluid within said marine organism skeletal derivative-based solid material to arrive at said spontaneous fluid uptake value.

In some embodiments, according to this aspect, the process further comprises the step of contacting said marine organism skeletal derivative-based solid material with a fluid and applying negative pressure to said marine organism skeletal derivative-based solid material to promote maximal uptake of said fluid within said marine organism skeletal derivative-based solid material to arrive at said total fluid uptake value.

In some embodiments, according to this aspect, the specific fluid uptake capacity value is a function of change in weight in said marine organism skeletal derivative-based solid material.

In some embodiments, according to this aspect, the change in weight in said marine organism skeletal derivative-based solid material is due to absorbance of said fluid within interstices in said solid material, or in some embodiments, due to absorbance of said fluid within pores in said solid material, or in some embodiments, the change in weight in said marine organism skeletal derivative-based solid material is due to absorbance of said fluid within interstices in said solid material and due to absorbance of said fluid within pores in said solid material, which in some embodiments, is within or in some embodiments, between, individual coral crystals.

In some embodiments, according to this aspect, the specific fluid uptake capacity value is a function of change in fluid volume of applied fluid to said coralline-based solid material.

In some embodiments, this invention provides a solid substrate for promoting cell or tissue growth or restored function, which solid substrate comprises an organism skeletal derivative and is characterized by having a contact angle value of less than 60 degrees, when in contact with a fluid.

In some embodiments, this invention provides a process for selection of an optimized organism skeletal derivative-based solid substrate for promoting cell or tissue growth or restored function, said process comprising:
  Isolating or preparing a organism skeletal derivative-based solid material;
  contacting said organism skeletal derivative-based solid material with a fluid and establishing a contact angle for said organism skeletal derivative; and
  selecting a organism skeletal derivative-based solid material characterized by a contact angle of less than 60 degrees.

In some embodiments, the processes of this invention, which facilitate selection of an optimized organism skeletal derivative-based solid substrate for promoting cell or tissue growth or restored function may include a step whereby the contact of the organism skeletal derivative-based solid material with a fluid and establishing a contact angle for said organism skeletal derivative, or the establishing a specific fluid uptake capacity value of said marine organism skeletal derivative-based solid material, which specific fluid uptake capacity value is determined by establishing a spontaneous fluid uptake value divided by a total fluid uptake value may be performed on samples immediately proximal to a sample of interest, and in some embodiments, from within a comparable region, for example, in terms of a region of coral growth in a growth ring, with the selection envisioned to be based in some embodiments, on the performance of proximal regions, and their achievement of the desired criteria for selection, as herein described.

In some embodiments, the marine organism skeletal derivative-based solid material is substantially comprised of calcium carbonate.

In some embodiments the process further comprises the steps of:
  establishing the presence of a substantially rough surface on said marine organism skeletal derivative-based solid material, which substantially rough surface is determined by scanning electron microscopy or atomic force microscopy; and
  selecting a marine organism skeletal derivative-based solid material characterized by a determination of the presence of a substantially rough surface on said marine organism skeletal derivative-based solid material.

In some embodiments, the invention provides a process for selection of an optimized organism skeletal derivative-based solid substrate for promoting cell or tissue growth or restored function, said process comprising:
  establishing the presence of a substantially rough surface on said marine organism skeletal derivative-based solid material, which substantially rough surface is determined by scanning electron microscopy or atomic force microscopy; and
  selecting a marine organism skeletal derivative-based solid material characterized by a determination of the presence of a substantially rough surface on said marine organism skeletal derivative-based solid material.

In some embodiments, the invention provides process for selection of an optimized organism skeletal derivative-based solid substrate for promoting cell or tissue growth or restored function, comprising a combination of the steps described for such processes as described herein.

In some embodiments, a process of this invention further comprises the step of contacting said solid substrate with cells or tissue.

In some embodiments, according to this aspect, the contacting promotes adhesion, proliferation or differentiation, or a combination thereof, of said cells or cells within said tissue.

In some embodiments, a fluid is a protein-containing, salt-containing or carbohydrate containing solution, or in some embodiments, the fluid is a biologic fluid, and in some embodiments, the biologic fluid is autologous or allogeneic with respect to a cell or tissue of a subject when said solid substrate is contacted with a cell or tissue of said subject. In some embodiments, the fluid is water.

In some embodiments, the solid substrate promotes cell or tissue growth in tissue damaged by trauma or disease.

In some embodiments, the invention provides a solid substrate produced by the process according to any aspect as herein described.

In some embodiments, this invention provides a process for converting a suboptimal marine organism skeletal derivative-based solid substrate to an optimized marine organism skeletal derivative-based solid substrates for promoting cell or tissue growth or restored function, said process comprising:
  a) establishing a specific fluid uptake capacity value for a group of marine organism skeletal derivative-based solid materials, which specific fluid uptake capacity value is determined by establishing a spontaneous fluid uptake value divided by a total fluid uptake value for each sample in said group;
  b) selecting a marine organism skeletal derivative-based solid material characterized by a specific fluid uptake capacity value;
  c) contacting said marine organism skeletal derivative-based solid material of (b) with an amphiphillic material, a polar solvent, a cationic material, an anionic material, or a combination thereof;
  d) determining a specific fluid uptake capacity as in (a) in said marine organism skeletal derivative-based solid materials obtained in (c); and
  e) selecting marine organism skeletal derivative-based solid materials obtained in (d) having a newly established increased specific fluid uptake capacity value.

This invention also provides a process for converting a suboptimal marine organism skeletal derivative-based solid substrate to an optimized marine organism skeletal derivative-based solid substrates for promoting cell or tissue growth or restored function, said process comprising:
  a) establishing a specific fluid uptake capacity value for a group of marine organism skeletal derivative-based solid materials, which specific fluid uptake capacity value is determined by establishing a spontaneous fluid uptake value divided by a total fluid uptake value for each sample in said group;
  b) selecting a marine organism skeletal derivative-based solid material characterized by a specific fluid uptake capacity value;
  c) subjecting said marine organism skeletal derivative-based solid material of (b) to cold plasma treatment, corona treatment, or a combination thereof;
  d) determining a specific fluid uptake capacity as in (a) in said marine organism skeletal derivative-based solid materials obtained in (c); and
  e) selecting marine organism skeletal derivative-based solid materials obtained in (d) having a newly established increased specific fluid uptake capacity value.

In some embodiments, the specific fluid uptake capacity value is increased by at least 5%. In some embodiments, the selected marine organism skeletal derivative-based solid material is characterized by a specific fluid uptake capacity value of between 75% and 95%. In some embodiments, the increased specific fluid uptake capacity value is increased by at least 15%. In some embodiments, the selected marine organism skeletal derivative-based solid material is characterized by a specific fluid uptake capacity value of between 45% and 70%. In some embodiments, the increased specific fluid uptake capacity value is increased by at least 35%. In some embodiments, the selected marine organism skeletal derivative-based solid material is characterized by a specific fluid uptake capacity value of between 1% and 40%. In some embodiments, the solid substrate is comprised substantially of a coral or coral-based derivative. In some embodiments, the solid substrate is comprised substantially of aragonite, calcite, hydroxyapatite or a combination thereof. In some embodiments, the process further comprises the step of fully or partially converting or coating a marine organism skeletal derivative-based solid material to hydroxyapatite prior to establishing said specific fluid uptake capacity value in (d), wherein said marine organism skeletal derivative-based solid material is aragonite. In some embodiments, the process further comprises the step of fully or partially converting a marine organism skeletal derivative-based solid material to hydroxyapatite subsequent to establishing said specific fluid uptake capacity value in (d), wherein said marine organism skeletal derivative-based solid material is mostly calcium carbonate. In some embodiments, the marine organism skeletal derivative-based solid material can be used as a bone filler or bone substitute material. In some embodiments, the amphiphillic material, a polar solvent, a cationic material or an anionic material is tween, pluronic, ethanol, methylene blue, hyaluronic acid, chondroitin sulfate or a combination thereof.

In some embodiments, the process further comprises the step of applying a secondary cleansing method to said marine organism skeletal derivative-based solid materials of (b), following contact with said amphiphillic material, polar solvent, cationic material, anionic material, or combinations thereof. In some embodiments, the secondary cleansing method includes applying heat, sonication, positive pressure, negative pressure, or a combination thereof. In some embodiments, the marine organism skeletal derivative-based solid material further comprises a bone filler, bone cement, bioglass or bone substitute material.

In some embodiments, the process further comprises the step of contacting said marine organism skeletal derivative solid material with a fluid for from 0.1-15 minutes, or in some embodiments, from 1-2 seconds to 20 minutes, or in some embodiments from 0.5-40 minutes, or in some embodiments from 0.1-60 minutes, allowing for spontaneous fluid uptake of said fluid within said marine organism skeletal derivative-based solid material to arrive at said spontaneous fluid uptake value. In some embodiments, the process further comprises the step of contacting said marine organism skeletal derivative-based solid material with a fluid for from 12 up to 24 hours, or in some embodiments, for from 2 to up to 15 hours, or in some embodiments, for from 1 to up to 24 hours, or in some embodiments from 0.05 up to 24 hours, or in some embodiments, for from 6 to up to 24 hours, or in some embodiments, for from 18 to up to 24 hours, allowing for spontaneous fluid uptake of said fluid within said marine organism skeletal derivative-based solid material to arrive at said spontaneous fluid uptake value.

In some embodiments, the process further comprises the step of contacting said marine organism skeletal derivative-based solid material with a fluid and applying negative pressure to said marine organism skeletal derivative-based solid material to provide for maximal uptake of said fluid within said marine organism skeletal derivative-based solid material to arrive at said total fluid uptake value. In some embodiments, the specific fluid uptake capacity value is a function of change in weight in said marine organism skeletal derivative-based solid material. In some embodiments, the specific fluid uptake capacity value is a function of change in fluid volume of applied fluid to said marine organism skeletal derivative-based solid material. In some embodiments, the fluid is a protein-containing, salt-containing or carbohydrate containing solution. In some embodiments, the biologic fluid is autologous with respect to a cell or tissue of a subject when said solid substrate is contacted with a cell or tissue of said subject. In some embodiments, the fluid is water. In some embodiments, the marine organism skeletal derivative-based solid material is isolated from a *Porites* species, *Goniopora, Millepora* species or an *Acropora* species. In some embodiments, the solid substrate is isolated from a barnacle or mollusk, or bone or ivory or dentin. In some embodiments, the solid substrate is comprised of nacre.

In some embodiments, the marine organism skeletal derivative-based solid material approximates the form of a cylinder, cone, tac, pin, screw, rectangular bar, plate, disc, pyramid, granule, powder, coral sand, ball, bone, condyle, rib, vertebra or cube. In some embodiments, the marine organism skeletal derivative-based solid material approximates a shape which accommodates a site of desired tissue growth or repair. In some embodiments, the marine organism skeletal derivative-based solid material comprises a hollow or hollows along a Cartesian coordinate axis of said coralline-based solid material.

In some embodiments, this invention provides a process for selection of an optimized marine organism skeletal derivative-based solid substrate for promoting cell or tissue growth or restored function, said process comprising:

Isolating or preparing a marine organism skeletal derivative-based solid material;

establishing a specific fluid uptake capacity value of said marine organism skeletal derivative-based solid material, which specific fluid uptake capacity value is determined by establishing a spontaneous fluid uptake value divided by a total fluid uptake value; or establishing a contact angle value; and selecting a marine organism skeletal derivative-based solid material characterized by a specific fluid uptake capacity value of at least 75% or characterized by having a contact angle value of less than 60 degrees, when in contact with a fluid establishing the presence of a substantially rough surface on said marine organism skeletal derivative-based solid material, which substantially rough surface is determined by scanning electron microscopy, x-ray diffraction or atomic force microscopy; and selecting a marine organism skeletal derivative-based solid material characterized by a determination of the presence of a substantially rough surface on said marine organism skeletal derivative-based solid material.

In some embodiments, this invention provides a process for selection of an optimized marine organism skeletal derivative-based solid substrate for promoting cell or tissue growth or restored function, said process comprising:

Isolating or preparing a marine organism skeletal derivative-based solid material;

establishing a specific fluid uptake capacity value of said marine organism skeletal derivative-based solid material, which specific fluid uptake capacity value is determined by establishing a spontaneous fluid uptake value divided by a total fluid uptake value; or establishing a contact angle value;

selecting a marine organism skeletal derivative-based solid material characterized by a specific fluid uptake capacity value of at least 75% or characterized by having a contact angle value of less than 60 degrees, when in contact with a fluid; and establishing a crystalline composition or structure of said marine organism skeletal derivative-based solid material, by use of x-ray diffraction or Feigl stain positive staining.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIGS. 1A-1C show 3 types of patterns of uptake within small coral solid substrate samples, reasonably full uptake as determined by surface color change observation, moderate uptake and minimal uptake, respectively. FIGS. 1D-1F show a larger block of the coral solid substrate from which the smaller implants were isolated.

FIGS. 3A-3F demonstrate the correlation between biologic fluid uptake before implantation and site healing over time. Implantation sites treated with implants characterized by significant water and blood uptake, or minimal uptake thereof within the implant before implantation, were evaluated macroscopically, at 4 weeks post. Tissue consistent with cartilage appearance substantially covered the implant, in samples with significant fluid uptake, whereas samples which were characterized by minimal/diminished fluid uptake presented with a more fibrous covering over the implant implantation (FIG. 3A versus 3D, respectively). X-ray and micro-CT analysis of the respective implants characterized by minimal/diminished fluid uptake [FIGS. 3B and 3C] versus those characterized by significant fluid uptake [FIGS. 3E and 3F] demonstrated that implant characterized by significant fluid uptake are appeared to be properly integrated within the implantation site with no significant adverse reaction with excellent osteointegration, ostoconduction and osteotransduction, while implants characterized by minimal/diminished fluid uptake are appeared to induce bone resorption, lysis and loss of mechanical integrity, possibly due to enhanced osteoclast activity.

FIGS. 4A and 4B show where the samples which were assessed for their contact angle characterization were cut from a larger block, and FIGS. 4C and 4D provide the contact angle values obtained for the indicated regions. The majority of regions of the block assessed in FIGS. 4A and 4B provided for a contact angle primarily of less than 60 degrees. Certain areas in FIGS. 4C and 4D provided for a contact angle of between 60 and 90 degrees (FIG. 4C) and over 90 degrees (FIG. 4D).

FIG. 5A shows regions cut from the larger block, which were assessed for their contact angle characterization. The majority of regions of the block assessed in FIGS. 5B and 5C provided for a contact angle primarily of less than 60 degrees. Certain areas in FIGS. 5B and 5C provided for a contact angle of between 60 and 90 degrees and over 90 degrees.

FIG. 6A shows regions cut from the larger block, which were assessed for their contact angle characterization. The majority of regions of the block assessed in FIG. 6B provided for a contact angle primarily of less than 60 degrees. Certain areas in FIG. 6B provided for a contact angle of between 60 and 90 degrees and over 90 degrees.

FIGS. 7A-7E demonstrate the results of ESEM analysis showing comparative surface wetting characteristics. The sample assessed in FIG. 7A showed a zero drop angle value, and no drop formation, indicating high hydrophilic structure. FIG. 7B depicts a sample, which following the application of fluid, failed to "wet" when water was applied. FIG. 7C shows that following re-desiccation, water droplets were evident on the surface, consistent with a phenotype of poor surface wetting. FIG. 7D present the results for a different sample, with results consistent with of contact angle less than 60 degrees and FIG. 7E present the results for a different sample, with contact angle higher than 60 degrees.

FIGS. 23A-23F depict traditional Feigl staining as reported in the literature (FIGS. 23A-23B), and blood uptake versus Feigl staining in coral samples isolated and processed by an embodied process of this invention, before (FIGS. 23C, 23D) and following a further ethanol purification step (FIGS. 23E, 23F).

DETAILED DESCRIPTION OF THE PRESENT INVENTION

Figure 1A:
FIGS. 1A-1F provide a series of photographs of implants, which were assessed for their ability to imbibe a biologic fluid, in this case, whole human blood.

This invention provides, inter alia, processes for selecting for and obtaining optimized solid substrates for promoting cell or tissue growth or restored function and materials obtained thereby.

In some embodiments, the invention provides a solid substrate for promoting cell or tissue growth or restored function, which solid substrate comprises coral and is characterized by a specific fluid uptake capacity value of at least 75%, which specific fluid uptake capacity value is determined by establishing a spontaneous fluid uptake value divided by a total fluid uptake value.

In some embodiments, this invention provides a solid substrate for promoting cell or tissue growth or restored function, which solid substrate comprises a organism skeletal derivative and is characterized by having a contact angle value of less than 60 degrees, when in contact with a fluid.

In some embodiments, the invention provides a solid substrate for promoting cell or tissue growth or restored function, which solid substrate comprises a marine organism skeletal derivative and is characterized by substantial surface roughness (Ra) as measured by scanning electron microscopy or atomic force microscopy.

The solid substrates of this invention will comprise a marine organism skeletal derivative-based material.

In some embodiments, the term "marine organism skeletal derivative-based material" refers to a solid piece or ground material derived from a marine organism, and from a skeletal component of the organism, such as an exoskeleton of the same further processed to be suitable for implantation in a human or veterinary subject, and further processed to be optimized for implantation as described hereinunder.

In some embodiments, the term "marine organism skeletal derivative-based material" refers to a coralline-based material further processed to be suitable for implantation in a human or veterinary subject, and further processed to be optimized for implantation as described hereinunder.

Coral, which is mainly comprised of $CaCO_3$ has been shown to possess the advantage of supporting fast cellular invasion, adherence and proliferation. Coral has been shown to be an effective substrate for facilitation of the adherence, proliferation and differentiation of mesenchymal stem cells, and ultimate incorporation into cartilage and/or bone tissue. Coral has also been shown to serve as an excellent substrate for promoting adherence and proliferation of a number of other cell types, serving as an excellent support for cell and tissue growth.

The terms "coral" and "calcium carbonate" and "aragonite" and "calcite" may be used interchangeably herein, unless specifically stated to the contrary.

In some embodiments, the term "marine organism skeletal derivative-based material" refers to a coral or coral derivative further processed to be suitable for implantation in a human or veterinary subject, and further processed to be optimized for implantation as described hereinunder. In some embodiments, the term "marine organism skeletal derivative-based material" refers to barnacle or mollusk-derived skeletal material further processed to be suitable for implantation in a human or veterinary subject, and further processed to be optimized for implantation as described hereinunder, and in some embodiments, inclusion of nacre further processed to be suitable for implantation in a human or veterinary subject, and further processed to be optimized for implantation as described hereinunder is contemplated.

In some embodiments, the term "marine organism skeletal derivative-based material" refers to a coral or coral derivative, which is isolated from a native marine organism, and subsequently processed as described herein, so as to be suitable for implantation within a human or veterinary subject, which marine organism skeletal derivative-based material has been specifically subjected to further processing, as described herein, including a prior cleaning and purification step, in order to convert a suboptimal isolated marine organism skeletal derivative-based material to an optimized marine organism skeletal derivative-based material for promoting cell or tissue growth or restored function.

In some embodiments, such optimization specifically includes contacting said marine organism skeletal derivative-based solid material with an amphiphilic material, a polar solvent, a cationic material, an anionic material, or a combination thereof.

In some embodiments, the solid substrate contains ground particles derived from coral, suspended in a biocompatible matrix. In some embodiments, the biocompatible matrix is a hydrogel.

In some embodiments, reference to an "implant" or "plug" or "solid substrate", as used herein refers to any embodiment or combined embodiments as herein described with regard to the solid substrates and to be considered as being included in the described aspect of this invention. For example, reference to a "solid substrate" as used herein, is to be understood to refer to any embodiment of a solid substrate as described herein being applicable for the indicated purpose or containing the indicated attribute, etc.

In one embodiment, "solid substrate" refers to a shaped platform used for cell and/or tissue repair and/or restored function, wherein the shaped platform provides a site for such repair and/or restored function. In one embodiment, the solid substrate is a temporary platform. In one embodiment, "temporary platform" refers to a natural degradation of a coral of this invention that occurs over time during such repair, wherein the natural fully or partially degradation of the coral may results in a change of solid substrate shape over time and/or change in solid substrate size over time.

It will be appreciated that different species of coral vary in terms of their average pore diameter and pore volume and the invention contemplates use of any such coral as a starting material for the preparation of the solid substrates as herein described, where the solid substrate is characterized in that it is characterized by a specific fluid uptake capacity value of at least 75% further processed to be suitable for implantation in a human or veterinary subject, and further processed to be optimized for implantation as described hereinunder.

As used herein, the term "pore volume" refers to volume or open spaces inside the porous scaffolding of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials; 26(27):5474-91, which is hereby incorporated by reference in its entirety.

It will be appreciated that the term "coral" will refer to a starting material from which aragonite, calcium carbonate, calcite, or hydroxyapatite etc. may be isolated and further processed to be suitable for implantation in a human or veterinary subject, and further processed to be optimized for implantation as described hereinunder.

In one embodiment, the solid substrates, processes and/or kits of this invention employ use of a coral further processed to be suitable for implantation in a human or veterinary subject, and further processed to be optimized for implantation as described hereinunder. In one embodiment, the coral comprise any species, including, inter alia, *Porites, Acropora, Goniopora, Millepora*, or a combination thereof. In another embodiment the solid substrates, processes and/or kits of this invention employ use of nacre, mollusc shell, or bone morsels.

In one embodiment, the coral is from the *Porites* species. In one embodiment, the coral is *Porites Lutea*. In one embodiment, the coral is from the *Acropora* species. In one embodiment, the coral is *Acropora grandis*, which in one embodiment is very common, fast growing, and easy to grow in culture. Thus, in one embodiment *Acropora* samples can be easily collected in sheltered areas of the coral reefs and collection from the coral reefs can be avoided by use of cultured coral material.

In another embodiment, the coral is from the *Millepora* species. In one embodiment, the coral is *Millepora dichotoma*. In one embodiment, the coral has a pore size of 150 μm and can be cloned and cultured, making *Millepora* useful as a framework in the solid substrates, methods and/or kits of this invention.

In one embodiment, the coral is from the *Goniopora* species. In some embodiments, the coral is *Goniopora albiconus, Goniopora burgosi, Goniopora cellulosa, Goniopora ceylon, Goniopora ciliatus, Goniopora columna, Goniopora djiboutiensis, Goniopora eclipsensis, Goniopora fruticosa, Goniopora gracilis, Goniopora klunzingeri, Goniopora lobata, Goniopora mauritiensis, Goniopora minor, Goniopora norfolkensis, Goniopora palmensis, Goniopora pandoraensis, Goniopora parvistella, Goniopora pearsoni, Goniopora pendulus, Goniopora planulata, Goniopora polyformis, Goniopora reptans, Goniopora savignyi, Goniopora somaliensis, Goniopora stokes, Goniopora stutchburyi, Goniopora sultani, Goniopora tenella, Goniopora tenuidens* or *Goniopora viridis*.

In another embodiment, the coral is from any one or more of the following species *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora cf hemprichi; Acropora kosurini; Acropora cf loisettae; Acropora longicyathus; Acropora loripes; Acropora cf lutkeni; Acropora paniculata; Acropora proximalis; Acropora rudis; Acropora selago; Acropora solitaryensis; Acropora cf spicifera* as per Veron; *Acropora cf spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia cf echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora cf vietnamensis; Oulophyllia laevis; Oxypora crassispinosa; Oxypora lacera; Pavona bipartita; Pavona venosa; Pectinia alcicornis; Pectinia paeonea; Platygyra acuta; Platygyra pini; Platygyra* sp "green"; *Platygyra verweyi; Podabacia cf lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata*; or any coral known in the art, or a combination thereof.

In another embodiment, derivatives of marine animals— such as coral, sponges, moluscs shells and other related organisms may be used in the solid substrates, methods and/or kits of this invention may be *Madreporaria, Helioporida* of the order Coenothecalia, *Tubipora* of the order Stolonifera, *Millepora* of the order Milleporina, or others known in the art. In some embodiments, coral for use in the substrates, methods and/or kits of this invention may comprise scleractinian coral, including in some embodiments, *Goniopora* and others. In some embodiments, coral for use in the substrates, methods and/or kits of this invention may comprise Alveoppora. In some embodiments, coral for use in the substrates, methods and/or kits of this invention may comprise bamboo corals, including in some embodiments, coral from the family Isididae, genera *Keratoisis, Isidella*, and others.

In one embodiment of this invention, the term "coral" refers to coral which is cut from a single piece of coral and further processed to be suitable for implantation in a human or veterinary subject, and still further processed to be optimized for implantation as described hereinunder.

In some embodiments, the solid substrate is of any desired shape.

In one embodiment, coral may be machined into a variety of configurations, and quite complex shapes such as cylindrical structures and threaded structures may be formed by appropriate machine or other processing, such as chemical processing. In another embodiment, coral may be shaped to form solid blocks, rods or granular forms. In one embodiment, coralline materials are shaped in such a way as to conform to the shape of a desired tissue structure or to fill gap and contour defects in a potential implantation site. In one embodiment, coral is implanted in an orientation that allows it to contact the maximum surface area of an adjacent-located tissue structure.

In some embodiments, the solid substrate approximates the form of a cylinder, cone, tac, pin, screw, rectangular bar, plate, disc, pyramid, granule, powder, coral sand, ball, bone, condyle, rib, vertebra, or cube. In some embodiments, the solid substrate approximates a shape which accommodates a site of desired tissue growth or repair.

In some embodiments, the solid substrate comprises a hollow or hollows along a Cartesian coordinate axis of said solid substrate.

In one embodiment, the size of coral solid substrates may be any size that would be useful for the purposes of the present invention, as would be known to one of skill in the Art depending on the purpose. For example and in one embodiment, the solid substrate may be substantially the same size as the structure it is meant to replace, while in another embodiment, the solid substrate or a portion thereof may be the size of a defect, fissure or fracture such that it may be placed therein to enhance/replace tissue formation/function in a discrete location. In one embodiment, a coral for use in a solid substrate of this invention comprises an average void diameter, average pore size or a combination thereof appropriate for cell seeding and/or development of vasculature.

The processes and materials of this invention, in some embodiments, rely on the isolation or preparation of the marine organism skeletal derivative-based solid material for use. In some embodiments, such isolation and preparation may include, inter alia, selection of a desired sample, including selecting a number of samples from a desired region of a growth ring in a larger coral sample, and/or in some embodiments, first processing of such sample, and/or in some embodiments, prescreening of such samples for their uptake of a fluid as described herein, and/or in some embodiments, further processing of such sample, as herein described. According to this aspect, such isolation and preparation will be effected prior to the described establishment of a specific fluid uptake capacity value of said marine organism skeletal derivative-based solid material, as herein described, and in some embodiments, prior to the selection of the marine organism skeletal derivative-based solid material as characterized by the described specific fluid uptake capacity value of at least 75% or contact angle value of less than 60 degrees, when in contact with a fluid, or surface roughness or Feigl stain positivity as herein described.

In one embodiment, coral is washed, bleached, frozen, dried, exposed to electrical forces, magnetic forces or ultrasound waves or microwaves or electromagnetic radiation or high pressure or a combination thereof prior to use thereof. According to this aspect, and in some embodiments, the coral is exposed to further processing, as described hereinunder.

In some embodiments, the solid substrate is of a size that is appropriate for the intended purpose, as will be appreciated by the skilled artisan.

For example, and in some embodiments, solid substrates for use in osteochondral therapy or repair may make use of a substrate that is cylindrical or oval in shape and in some embodiments, solid substrates of this invention and/or for use in the kits and methods as described may have a diameter of about 5-15 mm, and a height of about 5-25 mm. In some embodiments, the solid substrate has a diameter of about 1-35 mm, and a height of about 1-45 mm, or about 5-40 mm, and a height of about 5-60 mm, or about 5-15 mm, and a height of about 5-45 mm. 5-30 mm, 15-60 mm, or larger.

For example, and in some embodiments, solid substrates of this invention and/or for use in the kits and methods as described may make use of a substrate that is cylindrical or oval in shape and in some embodiments, solid substrates of this invention and/or for use in the kits and methods as described may have a diameter in the nanometer or micrometer scale. In some embodiments, solid substrates for use in osteochondral therapy or repair may make use of a substrate that is cylindrical or oval in shape and has a diameter of about 1-100 nm, or in some embodiments, having a diameter of about 50-1000 nm, or in some embodiments, having a diameter of about 10-2000 nm, or in some embodiments, having a diameter of about 100-4000 nm. In some embodiments, solid substrates for use in osteochondral therapy or repair may make use of a substrate that is cylindrical or oval in shape and has a diameter of about 1-100 μm, or in some embodiments, having a diameter of about 50-1000 μm, or in some embodiments, having a diameter of about 10-2000 μm, or in some embodiments, having a diameter of about 100-4000 μm.

For example, and in some embodiments, solid substrates of this invention and/or for use in the kits and methods as described may make use of a substrate that is cylindrical or oval in shape and in some embodiments, solid substrates of this invention and/or for use in the kits and methods as described may have a diameter in the millimeter or centimeter scale. In some embodiments, solid substrates for use in osteochondral therapy or repair may make use of a substrate that is cylindrical or oval in shape and has a diameter of about 1-100 mm, or in some embodiments, having a diameter of about 50-1000 mm, or in some embodiments, having a diameter of about 10-2000 mm, or in some embodiments, having a diameter of about 100-4000 mm. In some embodiments, solid substrates for use in osteochondral therapy or repair may make use of a substrate that is cylindrical or oval in shape and has a diameter of about 1-100 cm, or in some embodiments, having a diameter of about 50-1000 cm, or in some embodiments, having a diameter of about 10-2000 cm, or in some embodiments, having a diameter of about 100-4000 cm.

It will be appreciated by the skilled artisan that the size of the substrate may be so selected so as to be suitable to a particular application, for example, when using as a scaffolding material for bone repair, then the size may approximate the dimensions of a long bone in the subject. Accordingly, this invention is not to be limited by the size of the solid substrate.

The average diameter of the voids within the phases of the solid substrates of this invention may be determined by any means, including digital images analysis.

In some embodiments, the coral for use in accordance with the instant invention may be prepared as described in PCT International Application publication Number WO 2009/066283, PCT International Application publication Number WO 2010/058400, PCT International Application publication Number WO 2010/146574 and PCT International Application publication Number WO 2010/146574, each of which is fully incorporated by reference herein, in its entirety.

In some embodiments, coral is isolated from a natural source by known methods, and as described herein. In some embodiments, care is taken to isolate coral slices from a region of one or more growth rings within a larger coral sample, which region has been shown to possess the appropriate specific fluid uptake capacity value, the appropriate contact angle value and/or surface roughness, as described herein and in some embodiments, is then exposed to further processing as described hereinunder.

The processes of this invention promote obtaining a solid substrate of this invention, characterized by a specific fluid uptake capacity value as desired for the specific application for example of at least 75%, which specific fluid uptake capacity value is determined by establishing a spontaneous fluid uptake value divided by a total fluid uptake value.

As described and exemplified herein, for example, as described in Examples 3 and 4, a specific fluid uptake capacity value may be determined by evaluating spontaneous uptake of a biologic fluid versus a total uptake capacity for a given sample and arriving at the specific fluid uptake capacity level, whereby if the value is over 75%, then such solid substrate will be used in applications promoting cell and tissue growth and/or restored function.

In some embodiments, the process for selection of the solid substrate comprises isolating a sample of a coralline-based solid material and establishing a specific fluid uptake capacity value of the material, which specific fluid uptake capacity value is determined by establishing a spontaneous fluid uptake value divided by a total fluid uptake value and selecting material characterized by a specific fluid uptake capacity value of at least 75%.

In some embodiments, the biologic fluid is blood, and in some embodiments, the biologic fluid is water. In some embodiments, the biologic fluid is hydrophilic.

In some embodiments, the biologic fluid is autologous with respect to a cell or tissue of a subject when said solid substrate is contacted with such cell or tissue of said subject.

It will be understood that the biologic fluid may be any fluid which is biocompatible and whose incorporation is appropriate within a solid substrate for the desired application.

In some embodiments, the process further comprises the step of contacting the material with a fluid for from 2-15 minutes to promote spontaneous fluid uptake of said fluid within said coralline-based solid material to arrive at said spontaneous fluid uptake value. In some embodiments, the process may allow for the contacting of the material with a fluid for from 0.5-15 minutes, or in some embodiments, from 0.5-5 minutes, or in some embodiments, 10-60 minutes, or in some embodiments, from 60 to 90 minutes, or in some embodiments, other intervals, to promote spontaneous fluid uptake. The skilled artisan will appreciate that the amount of time for which the fluid is applied to determine the spontaneous uptake may be extended or shortened as a function of the dimensions and geometry of the sample substrate being assessed. In some embodiments, when a larger sample is being assessed, the process further comprises the step of contacting the material with a fluid for from 2-24 hours to promote spontaneous fluid uptake of said fluid within said coralline-based solid material to arrive at said spontaneous fluid uptake value In some embodiments, the process further comprises the step of contacting said marine organism skeletal derivative-based solid material with a fluid and applying negative pressure, or in some embodiments, mechanical pressure, to said coralline-based solid material to promote maximal uptake of said fluid within said coralline-based solid material to arrive at said total fluid uptake value. In some embodiments, application of positive pressure is via the application of a vacuum or in some embodiments, mechanical pressure, to the substrate immersed in the fluid, promoting entry of the fluid therewithin.

In some embodiments, the process may further comprise the step of contacting said coralline-based solid material with a fluid and applying positive pressure to said coralline-based solid material to promote maximal uptake of said fluid within said coralline-based solid material to arrive at said total fluid uptake value. According to this aspect, and in some embodiments, care will be taken to ensure that the application of pressure does not in any way compromise the structural integrity of the solid substrate.

In some embodiments, application of positive pressure is via any manual means, for example, via the use of any applicator, syringe, etc., gravitational pressure, and others, as will be appreciated by the skilled artisan. In some embodiments, application of positive pressure is via forced osmosis, centrifugation and others. In some embodiments, combinations of the described methods and others are envisioned.

In some embodiments, a prescreening step may be undertaken. For example, and in some embodiments, a coral slice of a desired thickness is taken, which for example may be perpendicular to the coral sample ring growth. The slice may be evaluated for rapid uptake of a biological fluid, such as, for example, uptake of a colored proteinaceous fluid, such as blood. In some embodiments, blood from any source may be used, such as, for example, from livestock or other sources.

Samples which provide a rapid uptake as part of the described prescreen procedure may be further assessed for their specific fluid uptake capacity value.

For example, and in some embodiments, smaller samples or specific scaffolds may be isolated from the block from which the coral slice was taken for prescreening, from regions which were determined by the prescreen to provide rapid uptake of the biological fluid.

In some embodiments, scaffold and/or smaller samples are dried and then subjected to further processing. Such further processing, for example, ensures removal of matter, which would render the implants unfit for implantation in human or veterinary subjects. In some embodiments, such processing produces a product that is fit for implantation, in accordance with any regulatory body guidance, such as, for example, the ASTM F 1185-03: Standard Specification for Composition of Hydroxylapatite for Surgical Implants, or ASTM F 1581-08: Standard Specification for Composition of Anorganic Bone for Surgical Implants.

In some embodiments, such further processing includes the oxidation of organic residuals in the scaffold and/or smaller samples, and subsequent elimination of the oxidizing agent used. In some aspects, such oxidizing agent may include sodium hypochlorite, hydrogen peroxide (solutions thereof) or use of both, which in some embodiments, is followed by the application of a polar solvent.

In some embodiments, such further processing steps may be undertaken following the establishment of a specific fluid uptake capacity value and in some embodiments, such further processing steps may be undertaken prior to establishing the specific fluid uptake capacity value for the sample(s).

According to this aspect, and in some embodiments, such scaffold or smaller samples may be fully dried, and then assessed for their spontaneous fluid uptake value, for example, as described in Example 1 below. For example, the dry sample may be immersed in water and the spontaneous fluid uptake value assessed, followed by an assessment of the total fluid uptake value. According to this aspect, and in one embodiment, samples producing a specific fluid uptake capacity value of at least 75% are selected for further processing. In some embodiments, samples producing a specific fluid uptake capacity value of at least 60-95% are selected for still further processing.

In some aspects, such still further processing includes a process to improve or further optimize a specific fluid uptake capacity value of a given scaffold and/or sample, including processes to optimize same as described herein. In some embodiments, such further processing may include subjecting the scaffold and/or sample to polar solvent exposure, as herein described.

In some embodiments, the invention also provides a process for converting a suboptimal marine organism skeletal derivative-based solid substrate to an optimized marine organism skeletal derivative-based solid substrates for promoting cell or tissue growth or restored function, said process comprising:
a) establishing a specific fluid uptake capacity value for a group of marine organism skeletal derivative-based solid materials, which specific fluid uptake capacity value is determined by establishing a spontaneous fluid uptake value divided by a total fluid uptake value for each sample in said group;
b) selecting a marine organism skeletal derivative-based solid material characterized by a specific fluid uptake capacity value;
c) subjecting said marine organism skeletal derivative-based solid material of (b) to cold plasma treatment, corona treatment, or a combination thereof;
d) determining a specific fluid uptake capacity as in (a) in said marine organism skeletal derivative-based solid materials obtained in (c); and
e) selecting marine organism skeletal derivative-based solid materials obtained in (d) having a newly established increased specific fluid uptake capacity value.

In some embodiments, the further processing specifically contemplates cold plasma treatment, corona treatment or a combination thereof. In some embodiments, the further processing may include surface conversion to hydroxyapatite, for example, via hydrothermal reaction, by known methods.

In some embodiments, the solid substrates for promoting cell or tissue growth or restored function of this invention comprise an organism skeletal derivative characterized by having a contact angle value of less than 60 degrees, when in contact with a fluid.

Example 5 demonstrated that solid substrates characterized by a contact angle value of less than 60 degrees is comparable to samples having a specific fluid uptake capacity value of at least 75%, and therefore such samples are also to be considered as comprising part of this invention.

Methods for determining a contact angle are well known, and any appropriate method can be used. One embodiment of such a method is provided herein with regard to Example 5 and as described hereinabove.

In some embodiments the structure composition of the coral or coral derivative is determined by X-ray diffraction (XRD) or Feigl solution positive staining.

In some embodiments, the term "Feigl solution positive staining" or "Feigl stain positivity" refers to a staining pattern consistent with a standard Feigl staining pattern (black) as known in the art and as described herein, indicative of an aragonite crystalline structure.

Similarly, in some embodiments of this invention, there is provided a process for selection of an optimized organism skeletal derivative-based solid substrate for promoting cell or tissue growth or restored function, said process comprising:
Isolating or preparing a organism skeletal derivative-based solid material;
contacting said organism skeletal derivative-based solid material with a fluid and establishing a contact angle for said organism skeletal derivative; and
selecting a organism skeletal derivative-based solid material characterized by a contact angle of less than 60 degrees.

In some embodiments, coral-based solid substrates of this invention may be converted to partially or fully into hydroxyapatite by known methods.

According to this aspect, a solid substrate characterized by a specific fluid uptake capacity value of at least 75%, which specific fluid uptake capacity value is determined by establishing a spontaneous fluid uptake value divided by a total fluid uptake value may be converted to hydroxyapatite, and the indicated activity is present in the converted substrate.

In another embodiment, solid substrate characterized by having a contact angle value of less than 60 degrees, when in contact with a fluid may be converted to hydroxyapatite, and the indicated activity is present in the converted substrate.

In another aspect, a solid substrate is converted to hydroxyapatite, and the same is then assessed for the presence of a specific fluid uptake capacity value of at least 75%, which specific fluid uptake capacity value is determined by establishing a spontaneous fluid uptake value divided by a total fluid uptake value, and such substrates fulfilling the stated criteria are specifically selected and encompassed by the subject application.

In another aspect, a solid substrate is converted to hydroxyapatite, and the same is then assessed in terms of its contact angle and whether the angle is less than 60 degrees, and such substrates fulfilling the stated criteria are specifically selected and encompassed by the subject application.

According to this aspect, and in one embodiment, solid substrates as herein defined, such as, for example, coral samples or nacre or others as herein described are assessed by selecting a small dry sample for use in the processes as herein described, whose region of isolation from a larger block may be ascertained, in order to provide information regarding the characteristics of the area in the block from which additional samples may be isolated and then used.

In some aspects, the sample is dried under vacuum and/or heated or pressurized or steam treated.

In some embodiments, for aspects relating to a specific fluid uptake capacity value, such value is a function of change in weight in said coralline-based solid material.

According to this aspect and in some embodiments, the dry weight for each sample is recorded and fluid as described herein is added an assay container.

According to this aspect and in some embodiments, at least 1:1 ratio of the size of the sample in mm to the volume of fluid added in ml is applied to the container. In some embodiments, the amount of fluid applied is in excess, as compared to the sample size.

According to this aspect and in some embodiments, once the initial fluid uptake is assessed, according to this aspect and in some embodiments, the solid substrate sample is then brought into contact with the fluid and the weight of the solid substrate sample is assessed. In other embodiments the specific gravity is assessed by gradient centrifugation of by the Archimedean principle.

According to this aspect and in some embodiments, spontaneous fluid uptake is assessed and a spontaneous fluid uptake value is established, based on the change in weight of the sample.

According to this aspect and in some embodiments, the specific fluid uptake capacity value is a function of change in fluid volume of applied fluid to said marine organism skeletal derivative-based solid material. According to this aspect, spontaneous fluid uptake is assessed and a spontaneous fluid uptake value is established based on the complete uptake of the volume applied to the sample.

According to this aspect and in some embodiments, the process then further comprises contacting a significantly increased amount of fluid with the sample and applying pressure thereto to promote maximal fluid uptake to the total fluid uptake capacity of the sample.

According to this aspect and in some embodiments, as noted, such pressure may be either positive or negative pressure, and the application time is for a period of time sufficient to ensure maximal uptake of the applied fluid into the marine organism skeletal derivative sample.

According to this aspect and in some embodiments, such time may include an interval of from 0.5-60 minutes, or in some embodiments, when a larger sample is being assessed, such time may include an interval of from 2-24 hours to arrive at said spontaneous fluid uptake value. It will be appreciated that the time intervals recited herein are applicable for any embodiment with regard thereto as described herein. The skilled artisan will appreciate that the amount of time for which the fluid is applied to determine the full capacity fluid uptake may be extended or shortened as a function of the dimensions and geometry of the sample substrate being assessed.

According to these aspects, the total fluid uptake capacity is thus assessed and the specific fluid uptake capacity value is then determined.

In some embodiments, the invention specifically contemplates solid substrates having a specific fluid uptake capacity value exceeding the cutoff value of 75%, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

In some embodiments, the invention specifically contemplates solid substrates characterized by having a contact angle value of less than 60 degrees, when in contact with a fluid, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

It is to be noted that the usefulness for coralline substrates for promoting tissue growth such as cartilage and bone has been previously shown. Surprisingly, it has now been found that while numerous coral-based substrates isolated can be used for such repair, consistent and superior function was found when the substrates were chosen specifically for their enhanced spontaneous uptake of biologic fluids. Surprisingly, it was found, not only that coral based materials can be an effective material for promoting cell and tissue growth and/or restored function, but that the spontaneous fluid absorptive characteristics of the selected sample of coral for use in the same provided even greater activity in this regard.

Without being bound by theory, and representing non-limiting embodiments of the substrates, processes and applications of this invention, specific selection of marine organism skeletal derivative-based solid substrates characterized by the desired specific fluid uptake capacity value of at least 75%, or specific selection of organism skeletal derivative-based solid substrates characterized by having a contact angle value of less than 60 degrees, when in contact with a fluid, may select for a sample whose vascularization is enhanced, or in some embodiments, whose access to lymph is enhanced, or in some embodiments, whose absorptive capacity heralds an affinity for extracellular matrix-associated materials, or in some embodiments, whose absorptive capacity heralds an affinity for cellular attraction including extravasation from proximal vessels.

In other embodiments, the substrates, processes and applications of this invention, specific selection of marine organism skeletal derivative-based solid substrates characterized by the desired specific fluid uptake capacity value of at least 75%, or specific selection of organism skeletal derivative-based solid substrates characterized by having a contact angle value of less than 60 degrees, when in contact with a fluid, or having a described surface roughness, may select for a sample which is particularly useful in anti-cancer applications.

In other embodiments, the substrates, processes and applications of this invention, specific selection of marine organism skeletal derivative-based solid substrates characterized by the desired specific fluid uptake capacity value of at least 75%, or specific selection of organism skeletal derivative-based solid substrates characterized by having a contact angle value of less than 60 degrees, or having a described surface roughness, when in contact with a fluid, may select for a sample which is particularly useful in promoting osteo-integration, osteo-conduction, osteo-transduction, chondrogenesis or cartilage regeneration.

In other embodiments, the substrates, processes and applications of this invention, specific selection of marine organism skeletal derivative-based solid substrates characterized by the desired specific fluid uptake capacity value of at least 75%, or specific selection of organism skeletal derivative-based solid substrates characterized by having a contact angle value of less than 60 degrees, when in contact with a fluid, or having a described surface roughness, may select for a sample which is particularly useful in promoting ex-vivo three-dimensional support and structure for cell, tissue or organ growth. In some embodiments, such cell, tissue or organ growth may include that for heart, muscle, liver, skin, kidney, blood vessel and neuronal growth and development.

In other embodiments, the substrates, processes and applications of this invention, specific selection of marine organism skeletal derivative-based solid substrates characterized by the desired specific fluid uptake capacity value of at least 75%, or specific selection of organism skeletal derivative-based solid substrates characterized by having a contact angle value of less than 60 degrees, when in contact with a fluid, or having a described surface roughness, may select for a sample which is particularly useful in promoting ex-vivo or in vitro stem cell growth, proliferation and/or differentiation for applications of same, including providing same for three-dimensional support and structure for cell, tissue or organ growth arising from same, for example, for applications in heart, muscle, liver, skin, kidney, blood vessel and neuronal growth and development.

It is to be understood that any of these mechanisms, and others, may account for the phenomenon of enhanced cell or tissue growth or restored function, and that any such mechanism associated with the application of an optimized marine organism skeletal derivative-based solid substrate for promoting cell or tissue growth or restored function characterized by a specific fluid uptake capacity value of at least 75% is to be understood as being part of this invention.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid may then be used for the isolation of proximally located regions of a section from which such sample was taken, which samples can then be reliably used and considered as being optimized in accordance with the processes of this invention. In some embodiments, with regard to coral-based samples, such regions may include the entire annual growth ring region within the coral from which the sample was derived.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid, may then be dried fully and utilized for implantation into a subject or for use as an ex-vivo substrate for cell, tissue or organ growth for subsequent implantation.

In some embodiments, and as exemplified in Example 9, herein, the substrates, processes and applications of this invention, whereby a marine organism skeletal derivative-based solid substrates is characterized by the desired specific fluid uptake capacity value, contact angle value or surface roughness promotes improved cell adhesion and viability to such substrates. According to this aspect, and in some embodiments, the cell adhesion and cell viability assays demonstrate that samples considered to be optimized for fluid uptake promote greater full cell adherence and viability over time.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

A solid substrate of this invention may in some embodiments be instead or concurrently characterized by a substantial surface roughness (Ra) as measured by scanning electron microscopy or atomic force microscopy, X-ray diffraction or Feigl solution analysis for positive staining or other known means for establishing the same, as will be appreciated by the skilled artisan.

As described and exemplified herein, for example, as described in Examples 6, certain sections of isolated coral provide a different phenotype, as compared to samples harvested from another region of a larger coral piece. Such phenotype may be reflected in the sample's absorptive capacity, surface structure roughness or both, with the stated difference resulting in a sample characterized in promoting cell and tissue growth and/or restored function.

In some embodiments, the process for selection of the solid substrate comprises isolating a sample of a coralline-based solid material and establishing the presence of a substantially rough surface on said marine organism skeletal derivative-based solid material, which substantially rough surface is determined by scanning electron microscopy or atomic force microscopy, X-ray diffraction or Feigl solution positive staining and selecting a marine organism skeletal derivative-based solid material characterized by a determination of the presence of a substantially rough surface on said marine organism skeletal derivative-based solid material, or positive staining (black) via Feigl solution staining.

In some embodiments, coral-based solid substrates of this invention may be converted to partially or fully into hydroxyapatite by known methods.

In another aspect, a solid substrate is converted to hydroxyapatite, and the same is then assessed for the presence of substantial surface roughness (Ra) as measured by scanning electron microscopy or atomic force microscopy or XRD analysis, and such substrates fulfilling the stated criteria are specifically selected and encompassed by the subject application.

Without being bound by theory, and representing non-limiting embodiments of the substrates, processes and applications of this invention, specific selection of marine organism skeletal derivative-based solid substrates characterized by the desired specific fluid uptake capacity value or desired surface roughness (Ra) as measured by methods for determining these characteristics as described herein, may select for a sample whose vascularization is enhanced, or in some embodiments, whose access to lymph is enhanced, or in some embodiments, whose absorptive capacity heralds an affinity for extracellular matrix-associated materials, or in some embodiments, whose absorptive capacity heralds an affinity for cellular attraction including extravasation from proximal vessels.

In some embodiments, the specific selection of marine organism skeletal derivative-based solid substrates characterized by the desired specific fluid uptake capacity value or desired surface roughness (Ra) as measured by methods for determining these characteristics as described herein, are useful in promoting anti-cancer activity. In some embodiments, the specific selection of marine organism skeletal derivative-based solid substrates characterized by the desired specific fluid uptake capacity value or desired surface roughness (Ra) as measured by methods for determining these characteristics as described herein, are useful in promoting osteo-integration, osteo-conduction, osteo-transduction, chondrogenesis or cartilage regeneration, or a combination thereof. In some embodiments, the specific selection of marine organism skeletal derivative-based solid substrates characterized by the desired specific fluid uptake capacity value or desired surface roughness (Ra) as measured by methods for determining these characteristics as described herein, are useful in promoting ex-vivo three-dimensional structural support for cells, tissue or organ growth, which in some embodiments, is particularly suitable for applications in the heart, muscle, liver, skin, kidney, blood vessel, or neurons.

It is to be understood that any of these mechanisms, and others, may account for the phenomenon of enhanced cell or tissue growth or restored function, and that any such mechanism associated with the application of an optimized marine organism skeletal derivative-based solid substrate for promoting cell or tissue growth or restored function characterized by the desired specific fluid uptake capacity value or desired surface roughness (Ra) as measured by methods for determining these characteristics as described herein, is to be understood as being part of this invention.

In some embodiments, samples thus processed and found to be characterized by the desired specific fluid uptake capacity value or desired surface roughness (Ra) as measured by methods for determining these characteristics as described herein, may then be used for the isolation of proximally located regions of a section from which such sample was taken, which samples can then be reliably used and considered as being optimized in accordance with the processes of this invention. In some embodiments, with regard to coral-based samples, such regions may include the entire annual growth ring region within the coral from which the sample was derived.

In some embodiments, samples thus processed and found to be characterized by the desired specific fluid uptake capacity value or desired surface roughness (Ra) as measured by methods for determining these characteristics as described herein, may then be utilized for implantation into a subject or for use as an ex-vivo substrate for cell or tissue growth for subsequent implantation.

In some embodiments, the marine organism skeletal derivative-based solid substrates of this invention may be processed/prepared to form a bone filler or bone substitute material.

In some embodiments, the marine organism skeletal derivative-based solid substrates of this invention are useful in orthopedic applications, including use as orthopedic screws, prostheses and others as will be appreciated by the skilled artisan. In some embodiments, the marine organism skeletal derivative-based solid substrates of this invention are useful in applications requiring a filler material, such as gap filler.

In some embodiments, such fillers may include active glasses, as are known to the skilled artisan. Other commercial products may be combined with the marine organism skeletal derivative-based solid substrates of this invention. In some embodiments, the bone filler materials described in the following U.S. patents may be combined with the marine organism skeletal derivative-based solid substrates of this invention: U.S. Pat. Nos. 5,939,039; 6,325,987; 6,383,519; 6,521,246; 6,969,501; and 6,991,803, all of which are hereby incorporated by reference in their entirety.

In some embodiments, the marine organism skeletal derivative-based solid substrates of this invention are useful in applications making use of reinforcing structures, for example as reinforcing screws, grafts, of others. In some embodiments, the methods and materials of this invention are useful in fixation of screws, prosthesis and other structures suitable for such application.

In some embodiments, the methods and materials of this invention are useful in wound healing. In some embodiments, the materials of this invention include a solid marine organism skeletal derivative-based solid substrate, in accordance with any embodiment thereof as described herein, including, inter alia, substrates on a millimeter or centimeter scale, or in some embodiments, use of powdered or granulated marine organism skeletal derivative-based solid substrates are envisioned.

In some embodiments, such wound healing may include healing of burns, necrotic tissue, diabetic ulcers, surgical wounds, and any wound, as will be appreciated by the skilled artisan.

In some embodiments, the methods and materials of this invention are useful in applications in avascular necrosis, cyst or bone tumor treatment, for example, following surgical excision of same.

In some embodiments, the methods and materials of this invention are useful in applications in cranio-facial skeletal surgery and skeletal reconstruction applications.

In other embodiments the substrate may be a mixture of several marine originated materials or a mixture of bone and coral granules or cartilage and coral granules. In some embodiments, the solid substrate may be a composite material comprised of multiple samples of the marine organism skeletal derivatives as herein described.

In one embodiment of this invention, the solid substrate may be isolated marine organism skeletal derivative material alone, or in some embodiment, the substrate may further comprise an additional material.

In some embodiments, such additional material may include a polymer.

The term "polymer" refers, in some embodiments, to the presence of a layer of polymeric material in association with at least a portion of the solid substrate material. In some embodiments, such polymer layer is a coating for the solid substrate material.

In some embodiments, such coating may be over the entirety of the solid substrate, and in some embodiments, such coating may penetrate to within the voids and/or pores and/or hollows of the solid substrate. In some embodiments, such coating may be selectively applied to a particular region of the solid substrate, such that it creates a separate phase on the solid substrate, and in some embodiments, such polymer may be so applied that a thick polymer layer or phase is associated with a portion of a solid substrate, thereby creating a separate polymer phase in association with the solid substrate as herein described.

In one embodiment, the polymer coating provides added features to the solid substrates as herein described, for example, added tensile strength, added flexibility, reduced brittleness, and other attributes, to the solid substrate and in some embodiments, the polymer coating results in greater cellular attraction and attachment to the solid substrates as herein described, which in turn, inter alia, results in enhanced repair in terms of quantity, quality and timing of repair. In some embodiments, the polymer coating enhance cells proliferation and/or differentiation into desired mature tissue which in turn, inter alia, results in enhanced repair in terms of quantity, quality and timing of repair.

In one embodiment of this invention, a polymer coating is permeable. In one embodiment, the permeable polymer coating comprises a special porous membrane. In one embodiment, the term "permeable" refers to having pores and openings. In one embodiment, the permeable polymer coating of this invention has pores and openings which allow entry of nutrients, a therapeutic compound, a cell population, a chelator, or a combination thereof. In one embodiment, the permeable polymer coating of this invention has pores and openings which allow exit/release of nutrients, a therapeutic compound, a cell population, a chelator, or a combination thereof.

In one embodiment, a polymer coating of this invention is discontinuous. In one embodiment, a region or a plurality of sub-regions of the coral of this invention comprise an absence of polymer coating, allowing direct contact between the coral and the environment.

In some embodiments, the marine organism skeletal derivative-based solid material comprises a biocompatible polymer attached to an outer surface of the substrate. In some embodiments, the solid substrate incorporates a biocompatible polymer therewithin, which is associated with the aragonite or calcite component, via any physical or chemical association. In some embodiments, the polymer is a part of a hydrogel, which is incorporated in the solid substrates of this invention. In some embodiments, such hydrogel-containing solid substrates may thereafter be lyophilized or desiccated, and may thereafter be reconstituted.

In some embodiments of the solid substrates of this invention, the polymer may be applied to the solid substrate so as to form a separate phase, or in some embodiments, the polymer may be applied as a layer onto the solid substrate, or in some embodiments, the solid substrate may comprise both polymer as an internal or externally associated layer with a separate phase attached thereto comprising the same or a different polymeric material.

Such polymer-containing solid substrates may be particularly suited for cartilage repair, regeneration or enhancement of formation thereof. In some embodiments, according to this aspect, for example, in the treatment of osteochondral defects, the coralline-based solid substrate is of a dimension suitable for incorporation within affected bone, and further comprises a polymer-containing phase, which phase, when inserted within the affected defect site, is proximal to affected cartilage. In another aspect and representing an embodiment of this invention, the solid substrate comprises a polymer, which has permeated within the voids and pores of the solid substrate, which solid substrate is inserted within a site of cartilage repair and which polymer facilitates cartilage growth, regeneration or healing of the defect site.

Such polymer-containing solid substrates may be particularly suited for bone repair, regeneration or enhancement of formation thereof. In some embodiments, according to this aspect, for example, in the treatment of bone edema, bone breakage or fragmentation, disease or defect, the coralline-based solid substrate is of a dimension suitable for incorporation within affected bone, and further comprises a polymer, which polymer has permeated within the voids and pores of the solid substrate, which solid substrate is inserted within the bone and which polymer facilitates bone growth, regeneration or healing of the defect site.

In one embodiment, the biocompatible polymer comprises a natural polymer comprising a glycosaminoglycan, collagen, fibrin, elastin, silk, chitosan, alginate, and any combination thereof. In one embodiment, a polymer coating of this invention comprises a natural polymer comprising, collagen, fibrin, elastin, silk, hyaluronic acid, sodium hyaluronate, cross linked hyaluronic acid, chitosan, cross linked chitosan, alginate, calcium alginate, cross linked calcium alginate and any combination thereof.

In one embodiment, the polymer comprises synthetically modified natural polymers, and may include cellulose derivatives such as alkyl celluloses, hydroxyalkyl celluloses, cellulose ethers, cellulose esters and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

In one embodiment, of this invention, a polymer comprises a synthetic biodegradable polymer. In one embodiment of this invention, a synthetic biodegradable polymer comprises alpha-hydroxy acids including poly-lactic acid, polyglycolic acid, enantioners thereof, co-polymers thereof, polyorthoesters, and combinations thereof.

In one embodiment, a polymer of this invention comprises a poly(cianoacrylate), poly(alkyl-cianoacrylate), poly (ketal), poly(caprolactone), poly(acetal), poly($\alpha$-hydroxy-ester), poly($\alpha$-hydroxy-ester), poly(hydroxyl-alkanoate), poly(propylene-fumarate), poly (imino-carbonate), poly(ester), poly(ethers), poly(carbonates), poly(amide), poly(siloxane), poly(silane), poly(sulfide), poly(imides), poly (urea), poly(amide-enamine), poly(organic acid), poly (electrolytes), poly(p-dioxanone), poly(olefin), poloxamer, inorganic or organomatallic polymers, elastomer, or any of their derivatives, or a copolymer obtained by a combination thereof.

In one embodiment, a polymer of this invention comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly[lactide-co-($\varepsilon$-caprolactone)]; poly[glycolide-co($\varepsilon$-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment of this invention, a polymer comprises proteins such as zein, modified zein, casein, gelatin, gluten, serum albumin, collagen, actin, $\alpha$-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharide, polysaccharides such as alginate, carrageenan ($\chi$, $\lambda$, $\mu$, $\kappa$), chitosan, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly($\beta$-hydroxybutyrate), poly(3-hydroxyoctanoate) or poly(3-hydroxyfatty acids), or any combination thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a coral of this invention is covalently associated with the polymer coating via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfohydroxy succinamide (Sulfo NHS), 5-iodopyrimidines, N-carbalkoxydihydroquinolines, pyrroloquinolinequinones, genipin or a combination thereof.

In one embodiment, the cross-linking agent is a homobifunctional cross-linker, such as, for example, a N-hydroxysuccinimide ester (e.g. disuccinimidyl suberate or dithiobis (succinimidylpropionate), homobifunctional imidoester (e.g. dimethyladipimidate or dimethyl pimelimidate), sulfhydryl-reactive crosslinker (e.g. 1,4-di-[3'-(2'-pyridyldithio) propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazonium derivative (e.g. o-tolidine), bis-alkylhalide, or a combination thereof.

In one embodiment, the cross-linking agent is a heterobifunctional cross-linker, such as, for example, an amine-reactive and sulfhydryl-reactive crosslinker (e.g. N-succinimidyl 3-(2-pyridyldithio)propionate, a carbonyl-reactive and sulfhydryl-reactive crosslinker (e.g. 4-(4-N-maleimidophenyl)butyric acid hydrazide), or a combination thereof.

In some embodiments, the cross-linking agent is a trifunctional cross-linkers, such as, for example, 4-azido-2-nitrophenylbiocytin-4-nitrophenyl ester, sulfosuccinimidyl-2-[6-biotinamido]-2-(p-azidobenzamido)hexanoamido] ethyl-1,3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a coral of this invention with a polymer coating of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, freezing, applying mechanical forces or any combination thereof, to promote the physical association between a coral and a polymer coating as described herein.

In some embodiments, the choice of polymer, or application of polymer to a solid substrate as herein described may be so chosen, for an added ability to increase fluid uptake. Similarly, the surface of the solid substrate may be treated to increase fluid uptake therewithin, as well. In some embodiments, such surface treatment may include application of plasma to the solid substrate.

It will be apparent to one skilled in the art that the physical and/or chemical properties of a polymer application to a solid substrate of this invention and components thereof may influence methods of use of this invention and kits thereof, for inducing or enhancing cartilage and/or bone repair.

In one embodiment, the polymer as applied to the solid substrates of this invention has a thickness of between 2.0 µm and 0.1 µm. In one embodiment, the polymer coating has a thickness of about 1.0 µm. In one embodiment, the polymer coating of this invention has a thickness of between 10 µm and 50 µm. In one embodiment, the polymer coating as applied to the solid substrates of this invention has a thickness of about 10-25, or about 15-30, or about 25-50 µm. In one embodiment, the polymer coating as applied to the solid substrates of this invention has a thickness of about 0.0001-0.1 µm. In one embodiment, the polymer coating as applied to the solid substrates of this invention has a thickness of about 20-200 µm. In one embodiment, the polymer coating as applied to the solid substrates of this invention has a thickness of about 100-1500 µm.

In some embodiments, the polymer as applied to the solid substrates of this invention is a thin coating, which is associated with the solid substrates of this invention and has a thickness as indicated hereinabove.

In some embodiments, the polymer as applied to the solid substrates of this invention is applied throughout the solid substrates of this invention, such that, in some embodiments, the pores and voids within the solid substrates of the invention may be filled with polymers as herein described, and such polymer layer as applied may have a thickness of about 60-900 µm.

In some embodiments, the polymer as applied to the solid substrates of this invention is to a terminus or a portion of the coating forming an additional polymer phase on the solid substrates of the invention. According to this aspect, and in some embodiments, the polymer layer as applied will have a thickness of between about 0.01-10 mm.

In some embodiments, multiple solid substrates comprising polymeric additives are implanted into a desired implantation site, wherein the polymer thickness applied to a first solid substrate may vary as compared to a polymer thickness as applied to a second solid substrate, implanted in the desired site. Variations in such thickness may reflect the range described herein.

In one embodiment, the thickness of the polymer as applied to the solid substrates of this invention influences physical characteristics of a solid substrate of this invention. For example, the thickness of a polymeric application may influence elasticity, tensile strength, adhesiveness, or retentiveness, or any combination thereof of a solid substrate of this invention. In one embodiment, the polymer application increases the elasticity of a solid substrate of this invention. In one embodiment, a polymeric application increases the tensile strength of a solid substrate of this invention. In one embodiment, the adhesiveness of a polymeric application relates to adhesion of mesenchymal stem cells, blood vessels, tissue at a site of desired repair, including cartilage repair, cartilage tissue, or bone tissue, or a combination thereof. In one embodiment, a polymeric application decreases the adhesiveness of a solid substrate of this invention. In one embodiment, a polymeric application increases the adhesiveness of a solid substrate of this invention. One skilled in the art will recognize that a polymeric application may increase adhesiveness for an item while decreasing adhesiveness for another item. For example, in one embodiment, the polymeric application increases adhesiveness for a mesenchymal stem cell and decreases adhesiveness of an infective agent. In one embodiment, the retentiveness of a polymeric application relates to retention of a cell population. In one embodiment, the cell population retained within a polymer coating is a mesenchymal stem cell population, chondrocyte population osteoblast population, etc. In one embodiment, the retentiveness of a polymeric application relates to retention of effector compounds.

In one embodiment, the thickness of the polymeric application influences proliferation and/or differentiation of cells applied to the solid substrates of this invention, or influences the activation or migration of cells associated with cell or tissue growth/restored function to the substrates of this invention, or a combination thereof.

Incorporation of a biocompatible polymer such as hyaluronic acid within a solid substrate of this invention may be accomplished via any means, including, in some embodiments, pressure-driven application, for example, via application under vacuum, centrifugal force or mechanical pressure. In some embodiments, gravitational force is sufficient to allow appropriate and relatively homogenous penetration of the hyaluronic acid to a desired depth of the implant. According to this aspect, in one embodiment, visual inspection of the implant, for example using the staining with Fast Green/Safranin O, demonstrates uniform distribution of the hyaluronic acid through the substrate to a desired depth as a function of the time and conditions of application.

In one embodiment, the solid substrates of this invention may further comprise an effector compound, which in some embodiments, may be associated directly with the solid substrates of this invention, or in some embodiments, may be associated with a polymer, and applied in connection therewith.

In one embodiment, such effector compounds might include silver ions, copper ions or other metals, or combinations thereof. In another embodiment release of this compound might be facilitated by the application of electrical charge.

In another embodiment a first implant may be coated with a metal such as silver and a second implant may be coated with a second metal such as gold. Application of electrical field or actuation by battery might cause an electrical charge to flow between the implanted materials and lead to sterilization of the area due to discharge of silver ions. Such implementation might, for example, be useful in the treatment of osteomyelitis.

In one embodiment, the effector compound comprises a component of a kit of this invention for use for incorporation into a solid substrate of this invention as herein described.

In one embodiment of this invention, the effector compound comprises a cytokine, a bone morphogenetic protein (BMP), growth factors, a chelator, a cell population, a therapeutic compound, or an antibiotic, or any combination thereof.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immune-stimulatory. In another embodiment, the therapeutic compound inhibits inflammatory or immune responses. In one embodiment, the therapeutic compound comprises a pro-angiogenic factor. In one embodiment, the therapeutic compound or drug comprises an anti-inflammatory compound, an anti-infective compound, a pro-angiogenic factors or a combination thereof.

In one embodiment, the effector compound comprises, an anti-helminth, an antihistamine, an immune-modulatory, an anticoagulant, a surfactant, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the solid substrates, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the solid substrate and/or kits of this invention, or whose use thereof, is desired. In one embodiment, the agent is incorporated directly within a solid substrate, and/or kit of this invention. In another embodiment, the agent is incorporated within a solid substrate and/or kit of this invention, either by physical interaction with a polymer coating, a coral, or coral particles of this invention, and/or a kit of this invention, or association thereto.

In one embodiment, the "effector compound" is a therapeutic compound.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P, transcription factors or combinations thereof.

In any of the embodiments herein, coralline solid substrates, and their use in the methods of the present invention may further comprise, or be implanted with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet rich plasma (PRP), platelet derived growth factor (PDGF), or any combinations thereof. Examples of antibiotics include antimicrobials and antibacterials.

In one embodiment, effector compounds for use in a solid substrate and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the solid substrates and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The solid substrates and/or kits of this invention and/or methods of use of this invention may comprise nucleic acids, in one embodiment, or in another embodiment, the solid substrates and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, effector compounds for use in a solid substrate and/or a kit of this invention and/or a method of this invention may comprise, inter-alia, a cytokine, a bone morphogenetic protein (BMP), growth factor, a chelator, a cell population, a therapeutic compound, an anti-inflammatory compound, a pro-angiogenic compound or an antibiotic, or any combination thereof.

In some embodiments, the kits and/or marine organism skeletal derivative-based solid substrates of this invention comprise known osteoinductive materials, bone cements, bone glasses, or bone fillers or a combination thereof.

In some embodiments, the bone cements may include any known cement, including β-Tricalcium phosphate, Monocalcium phosphate monohydrate (MCPM) (Ca(H2PO4) 2H2O) and mixtures thereof, including Brucite cement. In some embodiments, the cement may include amorphous calcium phosphate (ACP), dicalcium phosphate dihydrate (DCPD), dicalcium phosphate anhydrous (DCPA), α-tricalcium phosphate (α-TCP), dicalcium phosphate (DCP), tetracalcium phosphate (TTCP), monocalcium phosphate monohydrate (MCPM), calcium carbonate (CC) and others, and mixtures thereof.

In some embodiments, the kits and/or marine organism skeletal derivative-based solid substrates of this invention comprise known, and in some embodiments, commercially available osteoinductive materials, including, for example, bioactive glasses, bone cement components such as β-TCP, poly(-methyl methacrylate).

In some embodiments, the solid substrates of this invention may be seeded with cells, cell populations or tissue.

In some embodiments, the cells or tissue comprise stem or progenitor cells, or a combination thereof.

In one embodiment of this invention, the cells or tissue as used in accordance with the substrates, methods of use or kits of this invention, are engineered to express a desired product.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be seeded on the solid substrate, or in some embodiments, may be incorporated into a polymeric application thereto, or a combination thereof.

In one embodiment, a cell population of this invention comprises mesenchymal stem cells. In one embodiment, the mesenchymal stem cells are transformed.

In one embodiment, a cell population comprises cells beneficial in repair of a tissue for which the implantation of a solid substrate of this invention is desired.

In some embodiments, the cells are beneficial in and/or promote cartilage and/or bone formation and/or repair. Such cells may include chondroblasts or chondrocytes; fibrochondrocyte; osteocyte; osteoblast; osteoclast; synoviocyte; bone marrow cell; stromal cell; stem cell; embryonic stem cell;

precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. the precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment, the solid substrate of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the solid substrate of this invention incorporates any cell which may participate in tissue repair, for example, in cartilage and/or bone formation or repair. In some embodiments, such cells represent autografts, in that cells are cultured ex-vivo to seed the cells on the solid substrates of the invention, and such seeded solid substrates are implanted into the subject.

In some embodiments, such cells may represent allografts or xenografts, which may be incorporated within the solid substrates of this invention and implanted within a site of repair.

In one embodiment, a coral of this invention comprises a cell population from in vitro culture of the coral for a time period sufficient to seed the cells in the coral. In one embodiment, the cell population is a mesenchymal stem cell population, chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In one embodiment, the mesenchymal stem cells; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof seeded in vitro are transformed. In one embodiment, the cell population comprises a cell population beneficial for cartilage repair. In one embodiment, the culture comprises a chelator. In one embodiment of this invention, the chelator in a culture comprises a calcium chelator.

In some embodiments, the solid substrate may further serve as a bone substitute or bone void filler. In some embodiments, the solid substrate may further incorporate a bone-substitute or bone void filler. In some embodiments, such bone-containing material may comprise autologous or allogeneic bone. In some embodiments, such bone-containing material may comprise animal bone.

As exemplified herein, blood, water and other hydrophilic fluids as described were applied to the coral samples and absorption of the fluid within the coral samples was assessed.

FIGS. 1A-1F depict the results of a representative absorption studies conducted as described, showing patterns of uptake, substantial uptake and partial, minimal or no uptake of a fluid, respectively, depending upon the sample assessed. This variability in the pattern of absorption surprisingly provided a means of selecting solid substrates with optimized efficacy in cell and tissue growth and/or restored function following implantation.

Example 2 as provided herein demonstrates correlation between substantial uptake of biological fluid within the implanted coral solid substrate and subsequent healing at the implantation site, in a surprisingly superior manner, as compared to coral solid substrates, which had minimal biological fluid uptake.

Also exemplified is the development of a screening protocol established to select for such optimized coral-based solid substrate for promoting cell or tissue growth, provided in Example 3.

Example 5 provides support for the characterization of organism skeletal derivative-based solid substrates having a contact angle value of less than 60 degrees, when in contact with a fluid, as being a comparable selection means as that provided by the specific fluid uptake capacity value, as described hereinabove.

This invention provides the unexpected application of optimally selected coral based solid substrates being useful in cell and tissue growth and/or restored function, and exemplified herein is the particular application for cartilage and bone repair and enhancement of formation.

In particular, this invention provides the unexpected application that bone regeneration, (optionally with osteo-integration, osteo-conduction and osteo-transduction) repair and enhancement of formation is optimal when the solid substrate is characterized by a specific fluid uptake capacity value of at least 75%, which specific fluid uptake capacity value was determined by establishing a spontaneous fluid uptake value divided by a total fluid uptake value and such substrate is inserted within a site for bone repair.

In particular, this invention provides the unexpected application that bone regeneration, repair and enhancement of formation is optimal when the solid substrate is characterized by having a contact angle value of less than 60 degrees, when in contact with a fluid and such substrate is inserted within a site for bone repair.

In other embodiments, this invention provides the unexpected advantage in terms of greater chondrogenesis, when the solid substrate is characterized by a specific fluid uptake capacity value of at least 75%, which specific fluid uptake capacity value was determined by establishing a spontaneous fluid uptake value divided by a total fluid uptake value and such substrate was inserted within the cartilage defect site.

In other embodiments, this invention provides the unexpected advantage in terms of greater chondrogenesis, when the solid substrate is characterized by having a contact angle value of less than 60 degrees, when in contact with a fluid and such substrate was inserted within the cartilage defect site.

This invention in some embodiments also provides the unexpected application of optimally selected coral based solid substrates being useful in cell and tissue growth and/or restored function, and exemplified herein is the particular application for cartilage and bone repair and enhancement of formation.

In particular, this invention provides the unexpected application that bone regeneration, repair and enhancement of formation optionally with osteointegration, osteoconduction and osteotransduction is optimal when the solid substrate is characterized by a substantial surface roughness (Ra) as measured by scanning electron microscopy or atomic force microscopy or XRD analysis and such substrate is inserted within a site for bone repair.

In other embodiments, this invention provides the unexpected advantage in terms of greater chondrogenesis, when the solid substrate is characterized by substantial surface roughness (Ra) as measured by scanning electron microscopy or atomic force microscopy or XRD analysis and such substrate was inserted within the cartilage defect site.

In some embodiments, solid substrates of this invention may be applied for use in a subject with a bone defect in need of repair, wherein access to the bone defect results in the creation of a defect in the overlying cartilage, and the solid substrates of this invention allow for the healing of affected bone or bone and cartilage tissues.

In other embodiments, such solid substrates may be administered to a subject with a cartilage defect in need of repair, wherein optimal insertion of the solid substrate for stimulation of cartilage repair necessitates anchoring of the scaffold in the underlying bone, for example, by creating void in the underlying bone for insertion of the solid substrates, and once inserted, the solid substrate facilitates repair of both the overlying cartilage and underlying bone.

In other embodiments, such solid substrate may be administered to a subject with an osteochondral defect, where both bone and cartilage tissue are in need of repair as part of the pathogenesis of the disorder. The solid substrates according to this aspect are in some embodiments, particularly suited for such applications.

It will be appreciated by the skilled artisan, that the applications, in particular, as related to bone therapy may include use of a solid substrate that incorporates any additional element as described herein, including, for example, bone allograft, bone autograft, bone substitutes, known bone void fillers, therapeutic compounds, and the like.

In some embodiments, the solid substrates of this invention may be used in conjunction with other known and/or available materials for stimulating/enhancing cell and/or tissue growth and/or restored function, for example, by promoting bone and/or cartilage repair.

In some embodiments, the solid substrates of this invention may be utilized to affix additional solid substrates, for example for use in whole joint repair or ligament repair, or other connector tissue repair.

In some embodiments, the solid substrates of this invention may be used for example, as a pin, in conjunction with other scaffolds for bone repair or regeneration, etc. It is to be understood that any use of the solid substrates of this invention, alone or in conjunction with other appropriate materials, for the treatment, repair or stimulation of cell or tissue growth or restored function is to be considered as part of this invention It will be appreciated that the solid substrates of this invention may be of any suitable shape or size to accommodate its application in accordance with the methods of this invention. For example, and in some embodiments, for applications of the solid substrates of this invention within long bones of a subject, the dimensions of the solid substrate will be scaled to approximate that of the site into which the scaffold will be implanted, and may be on an order of magnitude scaling from millimeters to centimeters, as needed. Similarly, shapes of the solid substrates of the invention may be any shape into which the solid substrates of this invention may be machined or processed, and may have any configuration as will be appropriate to achieve the desired application for cell and/or tissue growth and restored function.

In one embodiment, the coral is shaped in the form of the tissue to be grown. For example, the coral can be shaped as a piece of cartilaginous tissue, such as a meniscus for a knee or elbow; vertebra, spine applications, skull, disk, a joint; an articular surface of a bone, the rib cage, a hip, a pelvis, an ear, a nose, a ligament, the bronchial tubes and the intervertebral discs.

This invention provides, in some embodiments, coralline solid substrates for use in repairing cartilage and/or bone tissue defects associated with physical trauma or cartilage and/or bone tissue defects associated with a disease or disorder in a subject.

In one embodiment, the coralline solid substrate is shaped prior to use in a method of cartilage and/or bone repair. In one embodiment, the coralline solid substrates is shaped concurrent with a method of cartilage and/or bone repair, e.g., the coralline solid substrates may be shaped during surgery when the site of repair may be best observed, thus optimizing the shape of the coralline solid substrates used.

In some embodiments, multiple coralline solid substrates are inserted to maximally occupy a defect site, such that each coralline solid substrate may be inserted at a different angle and/or shape and/or depth and/or porosity to accommodate proper insertion into the desired region within a desired implantation site. It is to be understood that the reference to angles or positioning may be with regard to one or more coralline solid substrates inserted in a particular implantation site.

In one embodiment, the phrase "cartilage repair" refers to restoring a cartilage defect to a more healthful state. In one embodiment, restoring cartilage results in regeneration of cartilage tissue. In one embodiment, restoring cartilage results in regeneration of a full or partial thickness articular cartilage defect. In one embodiment, restoring cartilage results in complete or partial regeneration of cartilage tissue at a site of cartilage repair. In one embodiment, cartilage repair may result in restoration/repair of missing or defective bone tissue, wherein repair of a cartilage defect necessitates removal of bone tissue at a site of cartilage repair. In one embodiment, restoring cartilage results in regeneration of osteochondral defect. In one embodiment, cartilage repair comprises restoring cartilage defects of joints (e.g. knee, elbow, hip, shoulder joints), of ears, of a nose, or of a wind pipe.

In some embodiments, the "cartilage repair" refers to treating, preventing or ameliorating or abrogating the symptoms of, or ameliorating or abrogating the pathogenesis of osteoarthritis and degenerative changes in cartilage.

In one embodiment, the phrase "bone repair" refers to restoring a bone defect to a more healthful state. In one embodiment, restoring bone results in regeneration of bone tissue. In one embodiment, restoring bone results in the filling in of any fracture or void within a bone tissue. In one embodiment, restoring bone results in complete or partial regeneration of bone tissue at a site of bone repair. In one embodiment, bone repair may result in restoration/repair of missing or defective bone tissue. In one embodiment, bone repair comprises restoring bone defects of any bone, treating bone edema, and other bone disorders, as needed.

In some embodiments, the phrase "bone repair" refers to the treatment of a subject with osteoporosis, Paget's disease, fibrous dysplasias, bone edema or osteodystrophies. In another embodiment, the subject has bone and/or cartilage infirmity. In another embodiment, the subject has other bone remodeling disorders include osteomalacia, rickets, rheumatoid arthritis, achondroplasia, osteochodrytis, hyperparathyroidism, osteogenesis imperfecta, congenital hypophosphatasia, fribromatous lesions, multiple myeloma, abnormal bone turnover, osteolytic bone disease, periodontal disease, or a combination thereof. In one embodiment, bone remodeling disorders include metabolic bone diseases which are characterized by disturbances in the organic matrix, bone mineralization, bone remodeling, endocrine, nutritional and other factors which regulate skeletal and mineral homeostasis, or a combination thereof. Such disorders may be hereditary or acquired and in one embodiment, are systemic and affect the entire skeletal system.

In some embodiments, the phrase "bone repair" refers to treating, preventing or ameliorating or abrogating the symptoms of, or ameliorating or abrogating the pathogenesis of osteochondral defects, bone cysts, tumors, avascular necrosis and other related diseases or conditions.

The solid substrates, kits and methods of the invention may also be used to enhance bone and/or cartilage formation in conditions where a bone and/or cartilage deficit is caused by factors other than bone remodeling disorders. Such bone deficits include fractures, bone trauma, conditions associated with post-traumatic bone surgery, post-prosthetic joint surgery, post plastic bone surgery, bone chemotherapy, post dental surgery and bone radiotherapy. Fractures include all types of microscopic and macroscopic fractures. In one embodiment, some examples of fractures includes avulsion fracture, comminuted fracture, transverse fracture, oblique fracture, spiral fracture, segmental fracture, displaced fracture, impacted fracture, greenstick fracture, torus fracture, fatigue fracture, intra-articular fracture (epiphyseal fracture), closed fracture (simple fracture), open fracture (compound fracture) and occult fracture. In one embodiment, fractures meant to be treated using the methods of the present invention are non-union fractures.

In one embodiment, methods of this invention are utilized for induced or enhanced repair of a cartilage and/or bone defect or disorder or disease. In one embodiment, the cartilage defect results from a trauma, a tear, a sports injury, a full thickness articular cartilage defect, a joint defect, or a repetitive stresses injury (e.g., osteochondral fracture, secondary damage due to cruciate ligament injury). In one embodiment, the cartilage disorder comprises a disease of the cartilage. In one embodiment, methods of this invention induce or enhance cartilage repair in osteoarthritis, rheumatoid arthritis, aseptic necrosis, osteochondritis dissecans, articular cartilage injuries, chondromalacia patella, chondrosarcoma, chondrosarcoma—head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, ligaments, and fibrous tissue, but also the growth plate, meniscal system, and intervertebral discs.

In one embodiment, the solid substrates, kits and methods of the invention may also be used to augment long bone fracture repair; generate bone in segmental defects; provide a bone graft substitute for fractures; facilitate tumor reconstruction or spine fusion; provide a local treatment (by injection) for weak or osteoporotic bone, such as in osteoporosis of the hip, vertebrae, or wrist, or a combination thereof. In another embodiment, the solid substrates, kits and methods of the invention may also be used in a method to accelerate the repair of fractured long bones; treat of delayed union or non-unions of long bone fractures or pseudoarthrosis of spine fusions; induce new bone formation in avascular necrosis of the hip or knee, or a combination thereof.

In one embodiment, methods of this invention are evaluated by examining the site of cartilage and/or bone tissue repair, wherein assessment is by histology, histochemistry, palpation, biopsy, endoscopy, arthroscopy, or imaging techniques comprising X-ray photographs, computerized X-ray densitometry, computerized fluorescence densitometry, CT, MRI or another method known in the art, or any combination thereof.

In one embodiment, a method of this invention comprises inducing and enhancing cartilage and/or bone repair wherein implanting a solid substrate of this invention within a site of cartilage and/or bone repair influences and improves cartilage and/or bone repair.

In one embodiment, a method of this invention induces or enhances cartilage and/or bone repair, wherein the solid substrate attracts a population of cells to the solid substrate, thereby influencing or improving cartilage and/or bone repair.

A clinician skilled in the art will recognize that methods of this invention, which entail implanting a coralline solid substrate within a site of cartilage and/or bone repair, may require preparation of a site of cartilage and/or bone repair. These preparations may occur prior to implantation of a coralline solid substrate or simultaneously with implantation. For example, cartilage and/or bone tissue and/or other tissues proximal to a site of cartilage and/or bone repair may initially be drilled through to create a channel of dimensions appropriate for a coralline solid substrate used in the methods of this invention. Then the coralline solid substrate is implanted within the site so that a region of the coralline solid substrate penetrates the drilled cartilage and/or bone tissues. Alternatively, the coralline solid substrate may be attached to a tool capable of penetrating through cartilage and/or bone or other tissues, or a combination thereof. In this case, as the tool penetrates through the cartilage and/or bone tissue, the attached coralline solid substrate is simultaneously implanted.

In some embodiments, following implantation of the coralline solid substrate within a repair site, or several coralline solid substrates within the repair site, the coralline solid substrate is processed to optimize incorporation and optimal cartilage and/or bone repair. In some embodiments, such processing may comprise cutting, sanding or otherwise smoothing the surface of the coralline solid substrate or coralline solid substrates, for optimal repair.

In some embodiments, the solid substrates as herein defined will be characterized by a specific fluid uptake capacity value of at least 75%, which specific fluid uptake capacity value is determined by establishing a spontaneous fluid uptake value divided by a total fluid uptake value.

In some embodiments, the solid substrates as herein defined will be characterized as having a contact angle value of less than 60 degrees, when in contact with a fluid.

Figure 8C:
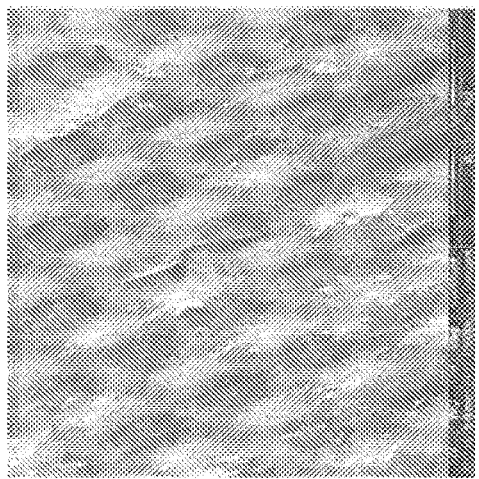
FIGS. 8A-8F demonstrate the microscopic structure as determined by ESEM, of isolated substrates characterized by minimal biologic fluid uptake (FIGS. 8A-8C), versus those characterized by substantial biologic fluid uptake (FIGS. 8D-8F) at various magnifications in samples with minimal biologic fluid uptake indicate a much smoother external surface as compared to samples with substantial uptake (FIGS. 8A-8C versus 8D-8F).
Figure 8F:
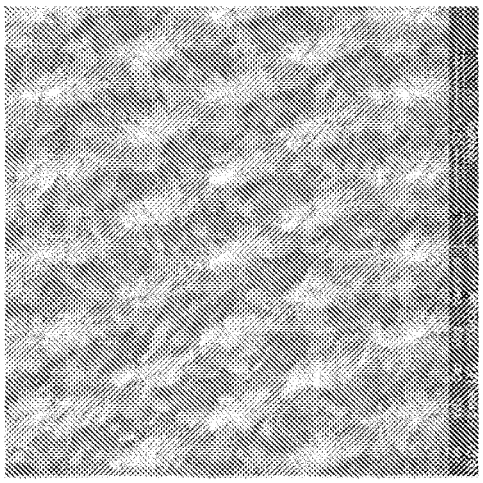
Figure 8B:
Figure 8E:
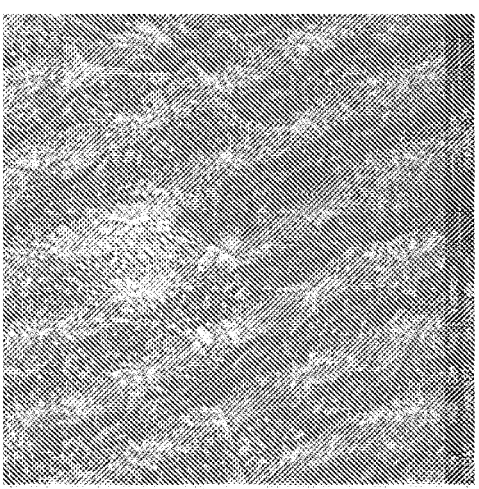
Figure 8A:
Figure 8D:
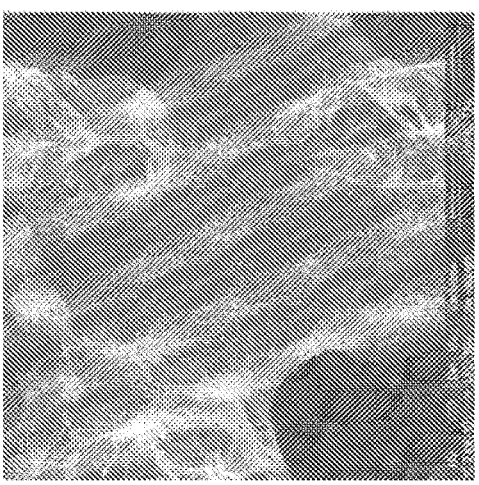

In some embodiments, the solid substrates as herein defined will be characterized by a structure such as that evident in FIGS. 8D-8F, when assessed by scanning electron microscopy. In some embodiments, the solid substrates as herein defined will be characterized by a structure such as that evident in FIGS. 9D-9F, when assessed by atomic force microscopy.

In some embodiments, when a solid substrate is prepared by a process comprising:
- isolating a marine organism skeletal derivative-based solid material;
- establishing a specific fluid uptake capacity value of said marine organism skeletal derivative-based solid material, which specific fluid uptake capacity value is determined by establishing a spontaneous fluid uptake value divided by a total fluid uptake value; and
- selecting a marine organism skeletal derivative-based solid material characterized by a specific fluid uptake capacity value of at least 75%, or in some embodiments, when a solid substrate is prepared by a process comprising:
- Isolating or preparing a organism skeletal derivative-based solid material;
- contacting said organism skeletal derivative-based solid material with a fluid and establishing a contact angle for said organism skeletal derivative; and
- selecting a organism skeletal derivative-based solid material characterized by a contact angle of less than 60 degrees;

or in some embodiments, such marine organism skeletal derivative-based solid material will be characterized by a substantial surface roughness (Ra) as measured by scanning electron microscopy or atomic force microscopy.

In some embodiments, the present invention provides processes for converting sub-optimized marine organism skeletal derivatives to marine organism skeletal derivatives providing for cell or tissue growth or restored function. In some embodiments, the present invention provides processes for optimizing marine organism skeletal derivatives providing for enhanced cell or tissue growth or restored function. In some embodiments, according to this aspect, the initial isolation and processing of such marine organism skeletal derivatives so as to be in a form compatible with implantation within mammalian tissue, for example, in human or veterinary applications, may diminish the specific fluid uptake capacity value and the optimization processes of this invention facilitate improvement of such value.

According to this aspect, and in some embodiments, such isolation and processing of marine organism skeletal derivatives for use in accordance with this invention includes exposure to a solution of sodium hypochlorite and hydrogen peroxide. According to this aspect, it is standard practice to treat coral/aragonite samples with sodium hypochlorite as part of a first cleaning/processing protocol [see for example, U.S. Pat. No. 5,433,751].

While various groups have proposed the use of coral-based materials in therapeutic applications in human subjects, there has been, to date, no indication that not all coral samples of a given species provide a therapeutic effect.

Surprisingly, it has now been found that there exists variability in the physical characteristics of the coral, which impact its therapeutic application, and moreover, that certain standard processing steps negatively impact the therapeutic potential of coral-based materials.

Even more surprising is the finding herein that the therapeutic activity can be restored and/or improved, by the application of certain process steps, for example, the selective application of ethanol to the sample as part of the processing steps of the coral-based materials of this invention.

In some embodiments, this invention provides a process for converting a suboptimal marine organism skeletal derivative-based solid substrate to an optimized marine organism skeletal derivative-based solid substrates for promoting cell or tissue growth or restored function, said process comprising:
- a) establishing a specific fluid uptake capacity value for a group of marine organism skeletal derivative-based solid materials, which specific fluid uptake capacity value is determined by establishing a spontaneous fluid uptake value divided by a total fluid uptake value for each sample in said group;
- b) selecting a marine organism skeletal derivative-based solid material characterized by a specific fluid uptake capacity value;
- c) contacting said marine organism skeletal derivative-based solid material of (b) with an amphiphilic material, a polar solvent, an a-polar solvent, a cationic material, an anionic material, or a combination thereof;
- d) determining a specific fluid uptake capacity as in (a) in said marine organism skeletal derivative-based solid materials obtained in (c); and
- e) selecting marine organism skeletal derivative-based solid materials obtained in (d) having a newly established increased specific fluid uptake capacity value.

In some embodiments, the increased specific fluid uptake capacity value is increased by at least 3%. In some embodiments, the increased specific fluid uptake capacity value is increased by at least 5%. In some embodiments, the increased specific fluid uptake capacity value is increased by at least 4.5%. In some embodiments, the increased specific fluid uptake capacity value is increased by from at least 3%-15%.

According to this aspect, and in some embodiments, such a marine organism skeletal derivative-based solid material is characterized by a specific fluid uptake capacity value of between 75% and 95%.

In some embodiments, the increased specific fluid uptake capacity value is increased by at least 10-15%. According to this aspect, and in some embodiments, such marine organism skeletal derivative-based solid material is characterized by a specific fluid uptake capacity value of between 45% and 70%.

In some embodiments, the increased specific fluid uptake capacity value is increased by at least 20-35%. According to this aspect, and in some embodiments, such marine organism skeletal derivative-based solid material is characterized by a specific fluid uptake capacity value of between 1% and 40%.

In some embodiments, the amphiphillic material is a detergent or surfactant. In some embodiments, the amphiphillic material is tween or a non-ionic copolymers composed of a central hydrophobic chain of for example polyoxypropylene (poly(propylene oxide)) flanked by two hydrophilic chains of for example polyoxypropylene.

In some embodiments, the polar solvent is an alcohol, such as ethanol, methanol, acetone, isopropanol and others.

In some embodiments, the a-polar solvent is toluene, hexane, xylene and others.

In some embodiments, the method further comprises the step of applying a secondary cleansing method to said marine organism skeletal derivative-based solid materials of (b), following or prior to contacting the substrate with the materials listed in (c).

In some embodiments, the secondary cleansing method includes applying pressure, heat, sonication, ethanol, organic solvent, salt buffer such as phosphate buffer, steam treatment or a combination thereof.

In some embodiments, the secondary cleansing method includes treatment with an organic solvent. In some embodiments, the secondary cleansing method includes enzymatic treatment, such as, but not limited to, use of papain, trypsin or chondroitinase ABC. In some embodiments, the secondary cleansing method includes sonication, heating, freeze drying, high pressure application, immersion under high pressure and the like.

In another embodiment, the invention provides a process for selection of an optimized marine organism skeletal derivative-based solid substrate for promoting cell or tissue growth or restored function, said process comprising:
  Isolating or preparing a marine organism skeletal derivative-based solid material;
  establishing the presence of a substantially rough surface on said marine organism skeletal derivative-based solid material, which substantially rough surface is determined by scanning electron microscopy or atomic force microscopy; and
  selecting a marine organism skeletal derivative-based solid material characterized by a determination of the presence of a substantially rough surface on said marine organism skeletal derivative-based solid material.

In some embodiments, according to this aspect, the process further comprises the step of contacting said marine organism skeletal derivative-based solid material with a fluid and applying negative pressure to said marine organism skeletal derivative-based solid material to promote maximal uptake of said fluid within said marine organism skeletal derivative-based solid material to arrive at said total fluid uptake value.

In some embodiments, the invention provides a solid substrate produced by the process according to any aspect as herein described.

It will be apparent to those skilled in the art that various modifications and variations can be made in the solid substrates, kits, process and methods of the present invention without departing from the spirit or scope of the invention.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Physical Properties Variability in Coralline-Based Solid Substrates of this Invention Materials and Methods A diamond disk saw was used to remove an outer coral layer, and large sections from which representative smaller sections of desired dimensions were cut from the coral block.

Coral from the hydrocoral *Porites lutea* which has an average pore size of 100-150 µm was harvested from various regions within a coral. The coral was evaluated visually for its appearance, density, and porosity. Coral was then optionally immersed in 5% sodium hypochlorite for removal of external organic tissue. Briefly, coral was first exposed to a 5% sodium hypochlorite solution for 30 minutes, 3 exchanges at temperature range RT at 50° C., and sub-atmospheric pressure using vacuum pressure ranging from 0.2-0.00001 Bar. The coral sections were then exposed to a 10% solution of hydrogen peroxide for 15 minutes at a temperature range of from RT –50° C., and subatmospheric pressure using vacuum pressure ranging from 0.2-0.00001 Bar. The cleaned sections were then washed in distilled water for 30 minutes, 3 exchanges at a temperature range of from RT –50° C., and sub-atmospheric pressure using vacuum pressure ranging from 0.3-0.00001 Bar.

The coral was optionally sterilized by exposure to gamma radiation at a strength of at least 22.5 kGy and can then be stored aseptically, in packaging material, and in particular, the smaller samples were irradiated, whereas larger blocks assessed were not irradiated.

Each section was then place in a plastic petri dish and 2 ml of fluid was applied to each dish. Observations regarding absorption of the fluid were recorded. Fluids used included animal blood, plasma, water and various colored solutions.

Results

To determine whether sample removal from various regions provides for materials, which vary in their physical characteristics and whether such variability provides for alternative qualities to the same, blood and other fluids listed were applied to the coral samples and absorption of the fluid within the coral samples was assessed.

FIGS. 1A-1F depict the results of a representative absorption study conducted as described. Coral samples were isolated from different regions of a coral block, and assessed for their pattern and intensity of absorption of blood applied thereto. Surprisingly, there appears to be no uniformity in terms of the absorption profile, and the same is not an "all or none" phenomenon.

Figure 1B:
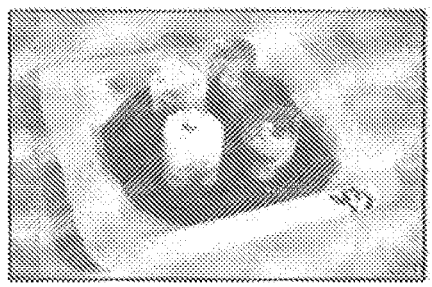
Figure 1C:
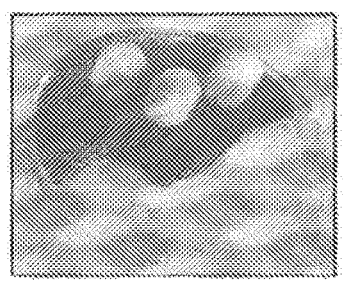
Figure 1D:
Figure 1E:
Figure 1F:
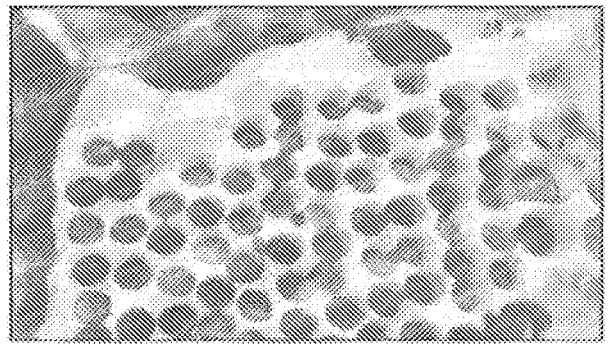

FIG. 1A for example, shows reasonably substantial absorption throughout the structure, whereas FIG. 1C shows poor to no absorption throughout, and FIG. 1B provides an interim phenomenon within the structure in that some regions substantially absorb the fluid and some regions absorb minimal to no fluid. FIGS. 1D-1F show cross-sectional slices through coral pieces from which coral plugs were cut and prepared, providing different patterns of absorption within the macrostructures, as well.

Other fluids were assessed in terms of their absorption within parallel samples comparable to the sample in FIG. 1C. To serve as a stain, a salt solution, and protein solution, carbohydrate solutions, ionic solutions were prepared and applied, and the results substantially mirrored that of the applied blood in that poor to no absorption occurred in the sample of FIG. 1C. Plain water applied thereto provided substantially the same, resulting in poor to no absorption within the coral sample of FIG. 1C.

FIGS. 1D-1F provide images of larger blocks of coral from which the samples of FIGS. 1A-1C were taken, respectively. As can be seen in FIG. 1D, the region from which the sample of 1A was taken shows good uptake of the fluid applied, in this case, blood, whereas the region from which the sample was taken in FIG. 1C (i.e. the block of FIG. 1F) shows minimal uptake, and the region from which the sample of FIG. 1B was taken, shown in FIG. 1E shows an intermediate uptake, in that some regions show good uptake, whereas other regions show minimal uptake.

As demonstrated herein, the size of the sample assessed is not limiting, and indeed samples of various sizes and thicknesses may be thus assessed. Furthermore, differences in surface tension are evident (compare FIG. 1C to FIG. 1A).

Example 2

Establishing a Screening Protocol for Coralline-Based Solid Substrates

Figure 2:
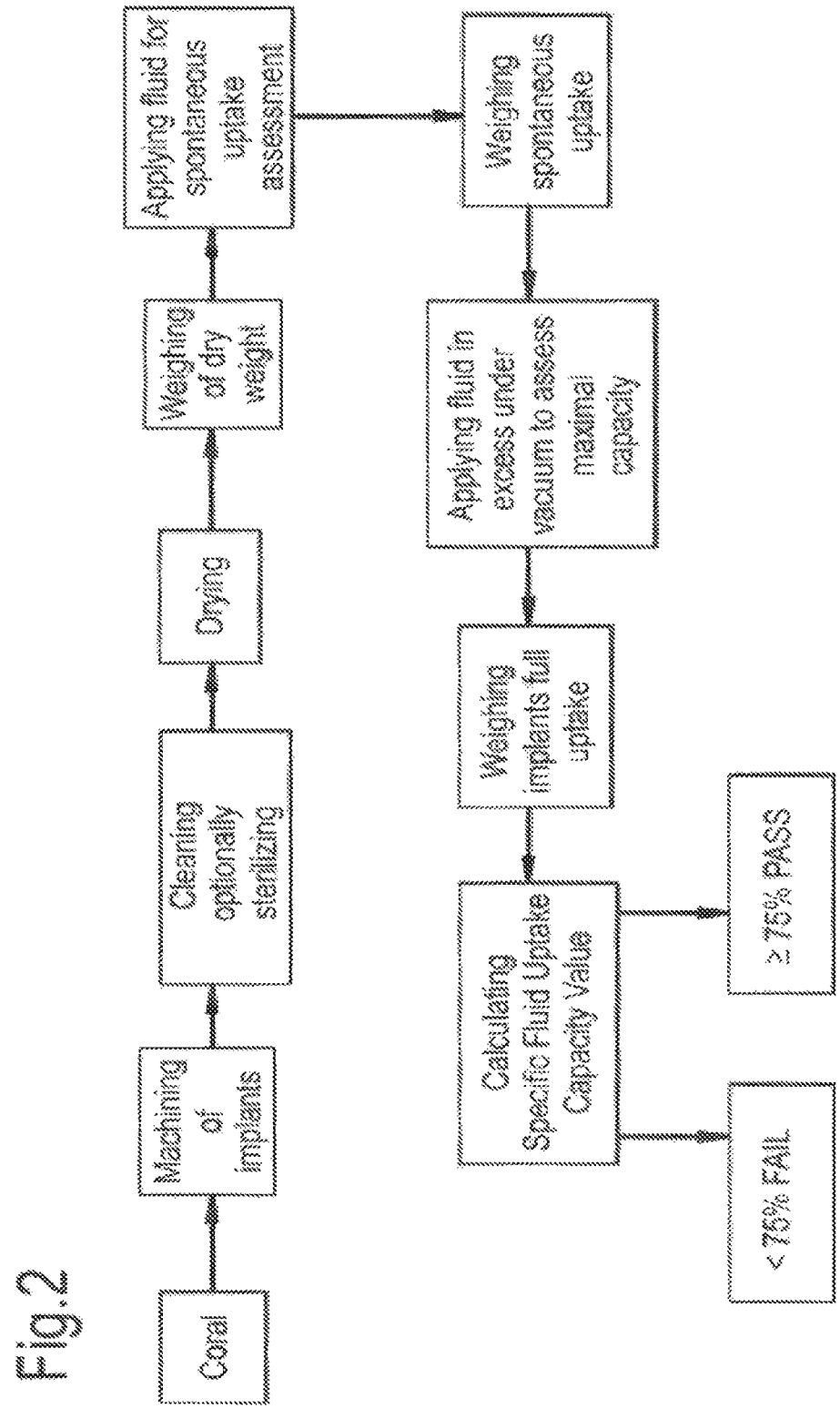
FIG. 2 presents a flow chart for an embodied screening protocol for the identification of optimized marine organism skeletal derivative-based solid substrates for promoting cell or tissue growth or restored function.

Based on the findings in Example 1, a screening protocol may be established to select for an optimized coral-based solid substrate for promoting cell or tissue growth or restored function. FIG. 2 provides a flow diagram of an envisioned screening protocol process. Coral samples are identified, isolated and machined to a desired size and shape, or assessed in blocks. The samples are then cleaned and optionally sterilized, then dried. The coral sample being assessed may be dried under vacuum and/or heated toward this end.

A dry weight for each sample may then be recorded.

Fluid as described herein is added to each assay container in an approximately 1:1 ratio or slightly more, i.e. equal to or slightly more than the size of the sample in mm as compared to the volume of fluid in ml is added to the container.

The sample may then be weighed and a spontaneous fluid uptake value is determined.

Samples may optionally be dried, prior to further manipulation of the sample.

A significantly increased amount of fluid is brought into contact with the sample and a vacuum is applied for a period of time to ensure maximal uptake of the applied fluid into the coral sample.

A total fluid uptake capacity is assessed and the specific fluid uptake capacity value is determined by dividing the spontaneous fluid uptake value by the total fluid uptake capacity.

If the value exceeds the cutoff value of 75%, then the sample will be noted for its suitability as a solid substrate for promoting cell or tissue growth or restored function. When the sample is utilized in vivo in subsequent applications, in some aspects, the sample is first contacted with autologous biological fluids or materials from the host prior to implantation into the same. If the value is less than the stated cutoff value, then the sample is not used as a solid substrate for promoting cell or tissue growth or restored function.

Example 3

Improved Solid Substrate Incorporation as a Function of Certain Physical Properties in Coralline-Based Solid Substrates of this Invention In order to assess the consequence of the phenotypic variability in blood absorption in the plugs of Example 1, coral plugs were prepared using a standard production method including three hypochlorite washes, hydrogen peroxide treatment and multiple double distilled water washes. Their spontaneous fluid uptake and total fluid uptake values were determined as described in Example 2, with water being the sample fluid assessed in this case. Sample implants exhibiting a spontaneous fluid uptake value of more than 75% were also checked for their spontaneous blood uptake ability.

Implants were graded as red, white, and intermediate, with intermediate referring to regions that are red and regions that remain white. Implants were placed in each goat knee so that each goat received implants characterized by a spontaneous fluid uptake value of more than 75% and implants which were characterized by a spontaneous fluid uptake value of less than 50%. The animals were followed for 4 weeks and then sacrificed.

Early cartilage formation was assessed macroscopically and histologically. Osteointegration and early bone formation or resorption was assessed using X-ray, micro-CT and histology FIGS. 3A-3F demonstrate the correlation between biologic fluid uptake before implantation and site healing over time. Implants characterized by significant water and blood uptake, or minimal uptake thereof within the implant, were implanted within a defect site and evaluated macroscopically, at 4 weeks post-implantation. Tissue consistent with hyaline cartilage appearance substantially covered the implant, in samples with significant fluid uptake, whereas samples which were characterized by minimal/diminished fluid uptake presented with a more fibrous capsule covering over the implant implantation (FIG. 3A versus 3D, respectively). X-ray and micro-CT analysis of the respective implants characterized by minimal/diminished fluid uptake [FIGS. 3B and 3C] versus those characterized by significant fluid uptake [FIGS. 3E and 3F] demonstrated that implants characterized by significant fluid uptake appear to be properly integrated within the implantation site with no significant adverse reaction. Implants characterized by minimal/diminished fluid uptake appear to induce bone resorption, lysis and loosening of the implant.

Example 4

Prescreening Coralline-Based Solid Substrates for Implantation

For applications in promoting cell or tissue growth or restored function, solid substrates are assessed for their ability to absorb fluid, such as, for example, water. Substrates that provide a specific fluid uptake capacity value of at least 75% are then implanted in the desired tissue site. For example, and representing one embodiment, such a solid substrate may be implanted within cartilage and neighboring bone for applications in repairing or regeneration in osteochondral defects or disease.

Solid substrates may be prepared according to any embodiment as described herein, as will be appreciated by the skilled artisan.

The substrates are envisioned for use in veterinary applications, as well as in the treatment of human subjects. At appropriate intervals, standard methodology is employed to assess good incorporation of the substrates and healing of the affected tissue, for example, X-ray, CT or MRI imaging may be performed to verify the position of the implants.

Implantation may be at any suitable location, for example, for knee joint repair, implantation may be within the Medial Femoral Condyle (MFC), Lateral Femoral Condyle (LFC), Patela, Trochlear Groove (TG) and the Tibia.

In applications relating to promoting cell or tissue growth or restored function, it is noted that solid substrates characterized by a specific fluid uptake capacity value of at least 75% will significantly outperform solid substrates characterized by a specific fluid uptake capacity value of less than 40%, in terms of their ability to promote cell or tissue growth or restored function at the site, promote healing at the implantation site, promote returned tissue function, or a combination thereof.

Example 5

Physical Properties Variability in Coralline-Based Solid Substrates of this Invention Natural surfaces are heterogenic due to their variable material composition, surface roughness and porosity and thus demonstrate variable water repellence/adhesion characteristics. Contact angle measurements can characterize the wetting of rough surfaces, taking the topography and the chemical structure of the surface into account.

Contact angle measurement was with goniometry. The contact angle is an equilibrium contact angle measured macroscopically on a solid surface. The same is to be distinguished from Young contact angles, measured on atomically smooth, chemically homogeneous surfaces.

The regions were classified into three classes and their relative surface areas were approximated as a percentage out of the total surface area:

Regions characterized by contact angles of between 0 and 60 deg, appear as white regions in the figures provided. Regions characterized by a contact angle of between 60 and 90 deg and regions characterized by a contact angle of 90 deg and higher are shaded in the figures provided.

Water drops of 1 ul-10 ul volume were deposited on cleaned and dried coral samples with a precise micro-dosing syringe. The contact angles were measured with a Rame-Hart goniometer (Model 500) with an accuracy of 0.1 deg (Bormashenko, 2012). Measurements were assessed for both sides of the drop and averaged. The test medium employed was physiologic saline.

Three 3×3 mm coral samples termed, R43, R34, and R44 were assessed. Prior to evaluation of contact angles, the specific fluid uptake capacity value was assessed for samples from each block, and the results are presented in Table 1.

| Coral | Specimen (Name) | specific fluid uptake capacity value |
|---|---|---|
| 43 | 1 | 0.62 |
|  | 2 | 0.46 |
|  | 3 | 0.60 |
|  | 4 | 0.31 |
|  | por1 | 0.17 |
|  | por2 | 0.17 |
|  | por3 | 0.37 |
| 44 | 1 | 0.32 |
|  | 2 | 0.82 |
|  | 3 | 0.88 |
| 34 | 1 | 0.70 |
|  | 2 | 0.39 |
|  | 3 | 0.33 |

Figure 4A:
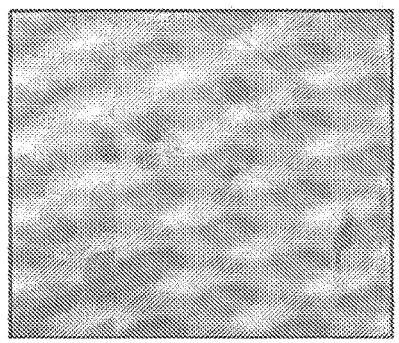
FIGS. 4A-4D provide photographs of embodied implants evaluated for their contact angle, when exposed to fluid.
Figure 4B:
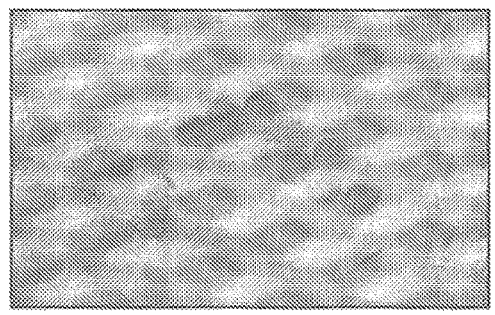
Figure 4C:
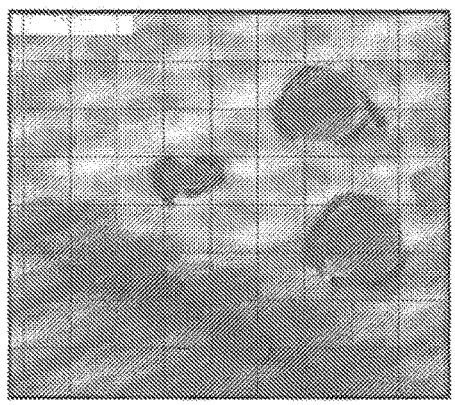
Figure 4D:
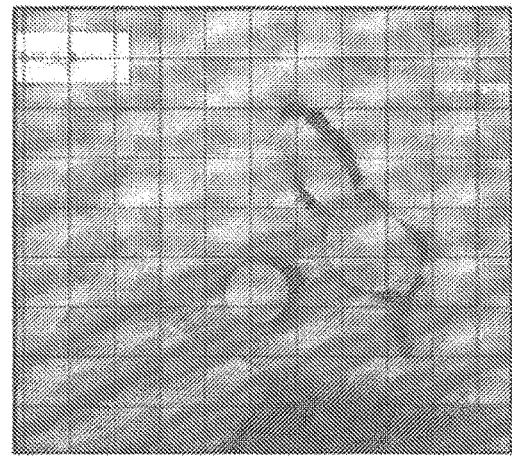

FIGS. 4A-4D provide photographs of coral sample R43 specimens evaluated for their contact angles. FIGS. 4A and 4B show regions cut from the larger block, which were assessed for their contact angle characterization. The majority of regions of the block assessed in FIGS. 4A and 4B provided for a contact angle primarily of less than 60 degrees. Certain areas in FIGS. 4C and 4D provided for a contact angle of between 60 and 90 degrees (FIG. 4C) and over 90 degrees (FIG. 4D).

Figure 5C:
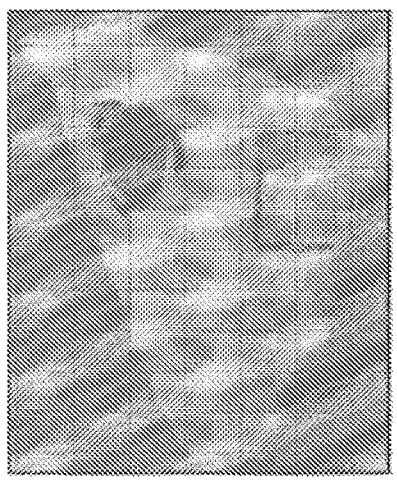
FIGS. 5A-5C are photographs of embodied implants evaluated for their contact angle, when exposed to fluid.
Figure 6B:
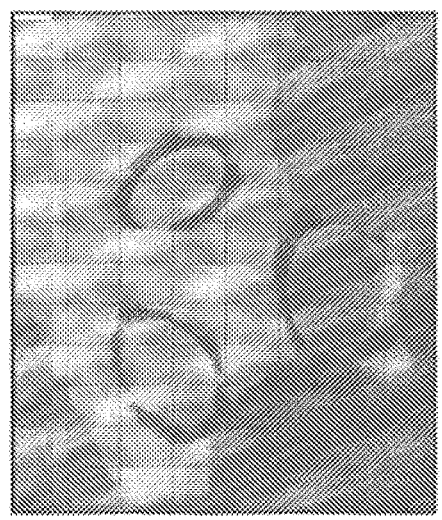
FIGS. 6A and 6B similarly provide photographs of embodied implants evaluated for their contact angle, when exposed to fluid.
Figure 5B:
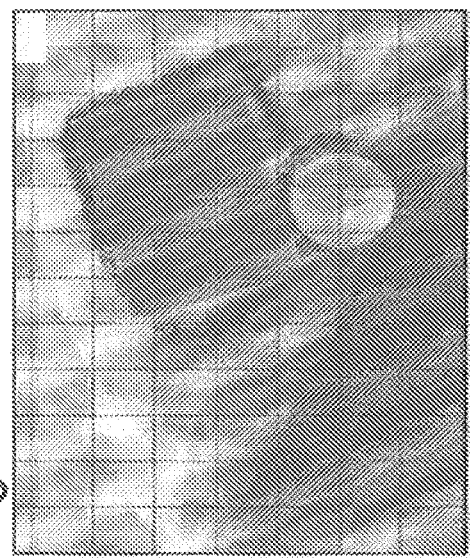
Figure 5A:
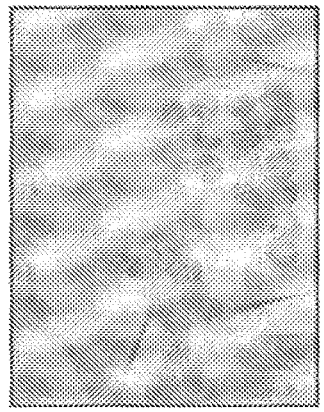
Figure 6A:
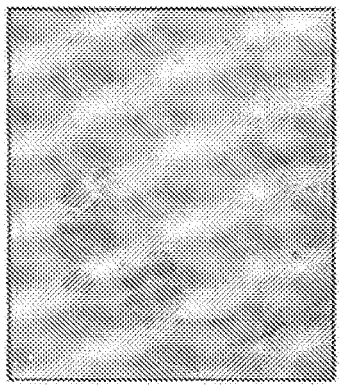

FIGS. 5A-5C provide provides photographs of coral sample R34 specimens evaluated for their contact angles. FIG. 5A shows regions cut from the larger block, which were assessed for their contact angle characterization. The majority of regions of the block assessed in FIGS. 5B and 5C provided for a contact angle primarily of less than 60 degrees. Certain areas in FIGS. 5B and 4C provided for a contact angle of between 60 and 90 degrees and over 90 degrees. FIGS. 6A and 6B similarly provide photographs of coral sample R44 specimens evaluated for their contact angles. FIG. 6A shows regions cut from the larger block, which were assessed for their contact angle characterization. The majority of regions of the block assessed in FIG. 6B provided for a contact angle primarily of less than 60 degrees. Certain areas in FIG. 6B provided for a contact angle of between 60 and 90 degrees and over 90 degrees.

The contact angle measurements parallel the specific fluid uptake capacity values obtained for respective coral samples. Accordingly, the improved solid substrates for promoting cell or tissue growth or restored function of this function may be characterized by either a determination of a contact angle, or a specific fluid uptake capacity value.

Furthermore, environmental scanning electron microscopy (ESEM) studies confirmed the results of the contact angle studies presented herein.

Table 2 presents the specific fluid uptake capacity values for the coral samples evaluated by ESEM.

| Coral | Specimen (Name) | specific fluid uptake capacity value |
|---|---|---|
| R27 | 7 | 0.87 |
| R30 | 40 | 0.04 |
| R43 | 1 | 0.62 |

FIGS. 7A-7E present the results of ESEM analysis conducted on the samples described in Table 2. Samples assessed from the R27-7 block provided for a zero drop angle value, and no drop formation seen (FIG. 7A). FIG. 7B-7C present the results for sample R30-40. FIG. 7B was taken following application of fluid, and it was noted that the sample failed to "wet" when water was applied. FIG. 7C shows that following re-desiccation, water droplets were evident on the surface, consistent with a phenotype of poor surface wetting.

FIGS. 7D-7E present the results for sample R43-1, with results consistent with those seen for sample R30-40.

Taken together, these results are corroborative of the contact angle data, as well specific fluid uptake capacity values obtained for respective coral samples. A sample having a specific fluid uptake capacity values obtained for respective coral samples of more than 75% exhibited no drop formation on the surface, consistent with a "good wetting" phenotype (FIG. 7A), whereas samples with a lower specific fluid uptake capacity value exhibited droplet formation during dessication.

Example 6

Physical Characteristics of Improved Coralline-Based Solid Substrates of this Invention Coral samples were processed as described in Example 1, hereinabove. Samples were then subjected to environmental scanning electron microscopy and atomic force microscopy, according to standard methods.

FIGS. 8A-8C demonstrate the surface structure of a solid substrate with a minimal specific fluid uptake capacity value as compared to that of substrates with a substantial specific fluid uptake capacity value (compare FIGS. 8A-8C and 8D-8F). Substrates with a lower specific fluid uptake capacity value exhibited a smoother outer surface structure, as compared to those with a higher specific fluid uptake capacity value, while the crystalline structure of the latter sample was easily seen.

Figure 9A:
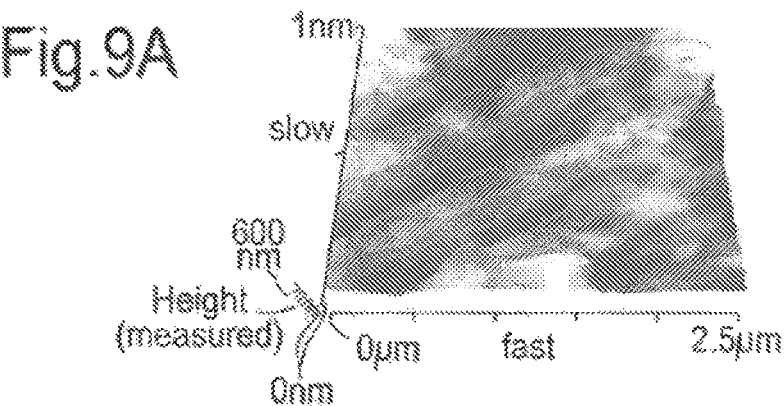
FIGS. 9A-9F demonstrate the microscopic structure as determined by AFM, of isolated substrates characterized by minimal biologic fluid uptake, versus those characterized by substantial biologic fluid uptake at various magnifications in samples with minimal biologic fluid uptake indicate a much smoother external surface as compared to samples with substantial uptake (FIGS. 9A-9C versus 9D-9F).
Figure 9B:
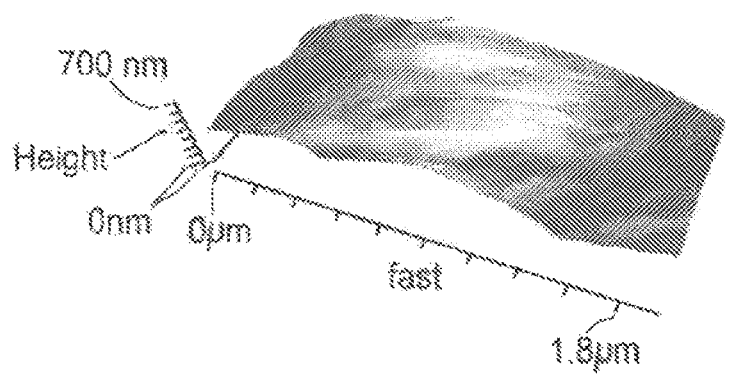
Figure 9C:
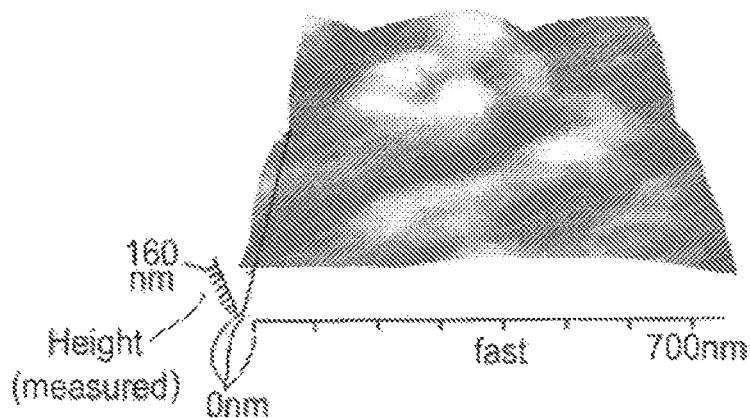
Figure 9D:
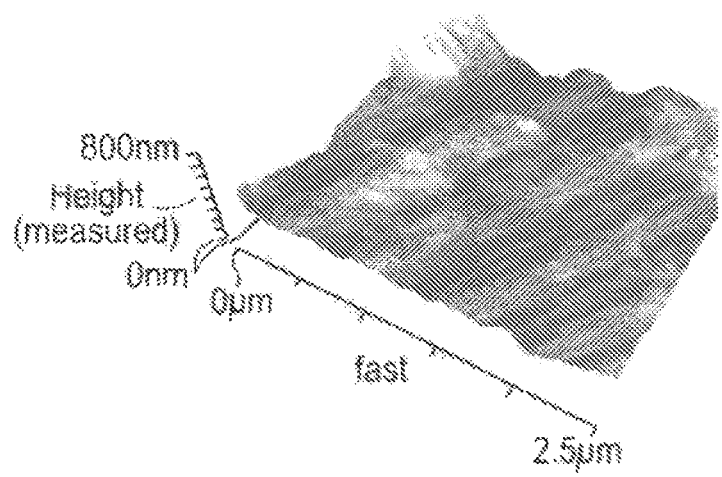
Figure 9E:
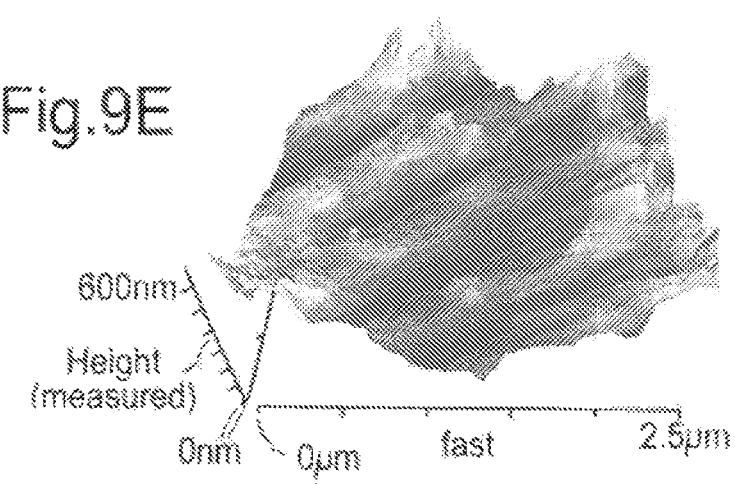
Figure 9F:
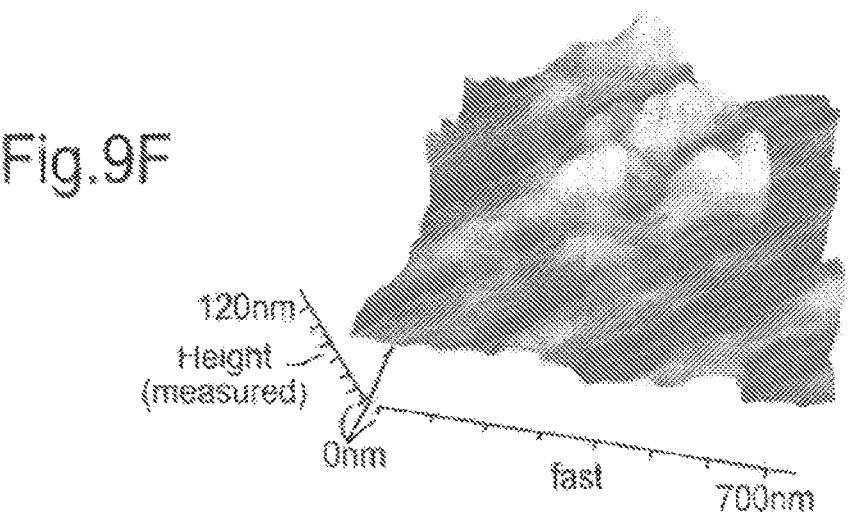

Furthermore, atomic force microscopy demonstrated that substrates with a lower specific fluid uptake capacity value were characterized by a smoother outer surface (FIGS. 9A-9C). In marked contrast, substrates characterized by a higher specific fluid uptake capacity value, exhibited a rougher surface (FIGS. 9D-9F).

Taken together, these results are corroborative of the fact that surface structure characterization correlates with specific fluid uptake capacity values obtained for respective coral samples. A sample having a specific fluid uptake capacity values obtained for respective coral samples of more than 75% exhibited a rougher surface, whereas samples with a lower specific fluid uptake capacity value exhibited a smoother surface.

Example 7

Development of a Process for Converting a Suboptimal Group of Marine Organism Skeletal Derivative-Based Solid Substrates to Optimized Marine Organism Skeletal Derivative-Based Solid Substrates Materials and Methods Coral samples of the hydrocoral *Porites lutea* were isolated as described in Example 1 and plugs were prepared.

Plugs were then weighed, establishing a dry weight per sample. Plugs were exposed to 2 ml of double distilled water for 5 minutes, then weighed, providing a spontaneous uptake value. Plugs were then exposed to an excess of double distilled water for 30 minutes under vacuum and then weighed, to determine the total fluid uptake value for each plug. The specific fluid uptake capacity value was then determined by dividing the spontaneous fluid uptake values by the total fluid uptake values obtained.

Each section was optionally placed in a plastic petri dish and 2 ml of fluid was applied to each dish, such as blood, and the respective phenotype of fluid uptake was preserved in samples which yielded a specific particular fluid uptake capacity value.

Samples shown to yield poor uptake and having a specific fluid uptake capacity value of less than 40%, samples shown to yield an intermediate overall specific fluid uptake capacity value of between 41% and 74% and samples shown to yield a specific fluid uptake capacity value of between 75% and 99% were then contacted with test materials. In some aspects, the test conditions included the application of 5 ml of 0.5% Tween 80.

In some aspects, the test conditions included sonication for 15 minutes; application of absolute ethanol; application of 5 ml pluronic with or without prior tween 80 application. In some aspects, the test conditions included the application of 5 ml of Methylene blue in 0.03% acetic acid or 3M 0.05% hyaluronic solution in DDW.

Following such treatments, the samples were then contacted again with a fluid as described above, such as water, and a specific fluid uptake capacity value was assessed again for each sample. Uptake of a fluid within the plug, such as uptake of blood was verified macroscopically, as well.

Samples providing a specific fluid uptake capacity value of more than 50% were similarly evaluated and compared to those with a value of less than 50%.

Results

Example 2 demonstrated that solid substrates characterized by a specific fluid uptake capacity value of at least 75% provide for cell or tissue growth or restored function and in a given isolated block of a marine organism skeletal derivative, there is variability in terms of the number of plugs that can be isolated therefrom, exhibiting the desired specific fluid uptake capacity value. It was therefore of interest to determine whether samples characterized by a specific fluid uptake capacity value of less than 40%, or of between 41% and 74%, or of between 75% and 99% could be increased, improving each substrates ability to provide for cell or tissue growth or restored function.

In order to determine if it were possible to isolate samples of such skeletal derivatives characterized by the indicated ranges for each specific fluid uptake capacity value, respectively, and to treat the sample to thereby improve the specific fluid uptake capacity value to be greater than that previously obtained, a number of manipulations of the sample were undertaken.

Figure 10:
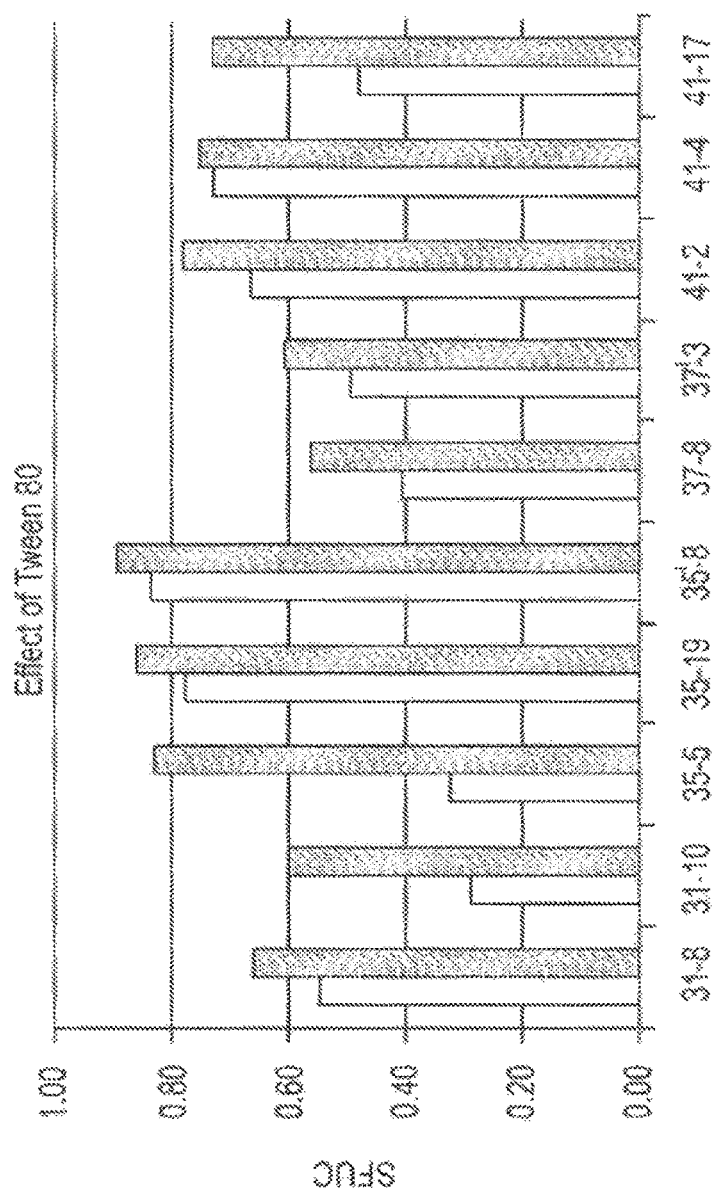
FIG. 10 plots the SFUC value as a function of coral sample assessed, prior to and following application of Tween 80 to such samples.

Tween 80 is a non-ionic surfactant and emulsifier derived from polyethoxylated sorbitan and oleic acid. Tween 80 was therefore assessed for its ability to alter the specific fluid uptake capacity value of the coral samples tested. FIG. 10 provides the results of a number of samples assessed. In essentially every sample assessed, tween treatment increased the specific fluid uptake capacity (SFUC) value. Some samples exhibiting lower SFUC values were significantly enhanced. Sample 31-10, 35-5 and others, exhibited an initial SFUC value of less than about 30% and showed a marked increase in SFUC following tween 80 treatment, to values as high as over 60% and even over 80%. When blood was applied to the samples, rapid uptake occurred, in marked contrast to prior poor uptake (FIG. 10). Since treatment of the plugs with an amphiphillic compound provided for increased SFUC in all samples evaluated, it was of interest to determine whether other manipulations would improve this phenomenon.

Figure 11:
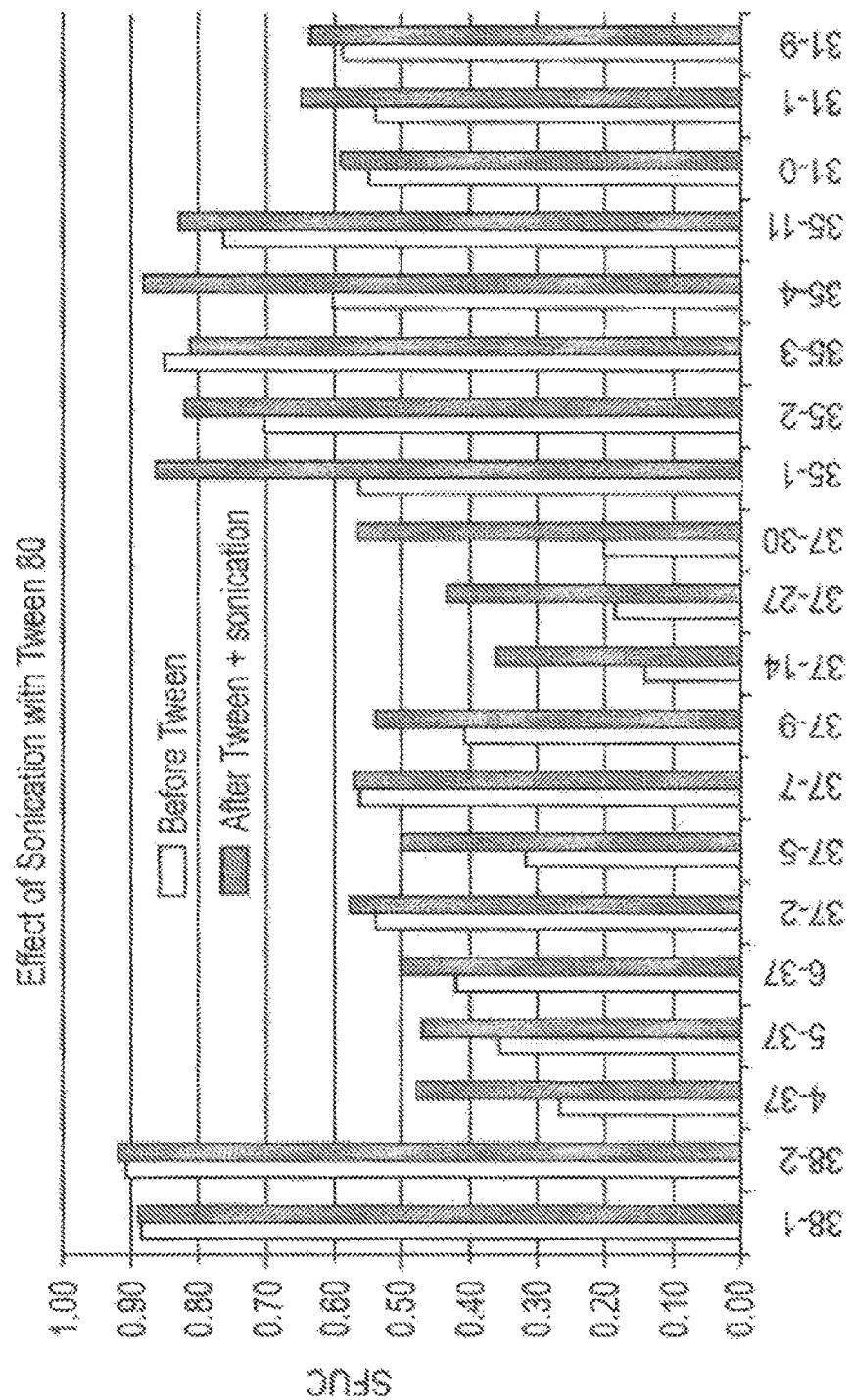
FIG. 11 plots the SFUC value as a function of coral sample assessed, prior to and following application of Tween 80 and sonication to such samples.

Toward this end, samples to which Tween 80 had been applied were then subjected to sonication, as well. FIG. 11 demonstrates the results of such process. As can be seen in the figures, in most samples, the SFUC obtained with tween 80 treatment and sonication improved the subsequent SFUC value. Sample 37-30, 37-14 and others, exhibited an SFUC increase to more than double the initial value In a number of samples, tween 80 and sonication treatment resulted in SFUC values of more than 85%.

Figure 12:
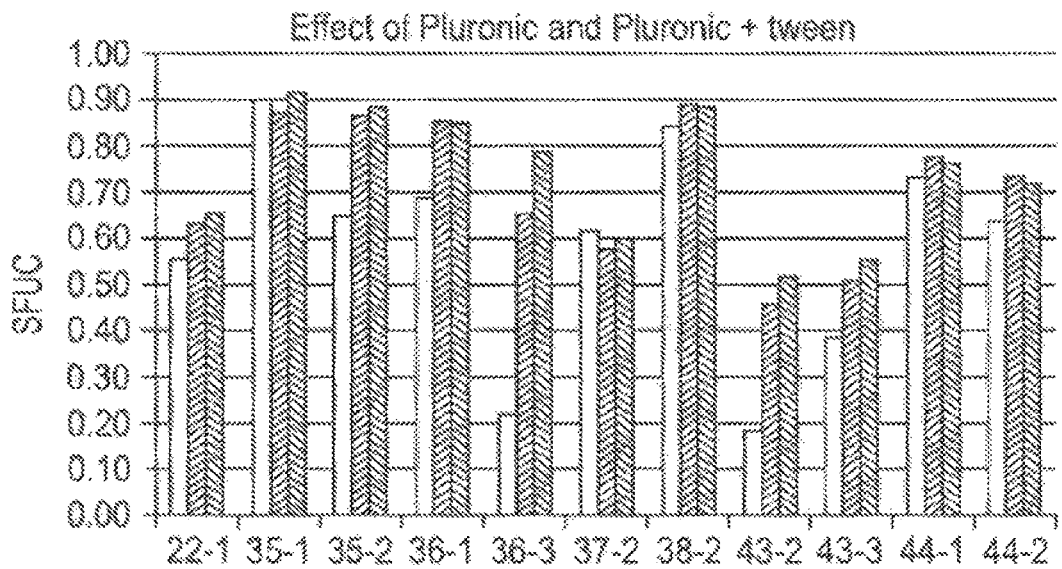
FIG. 12 plots the SFUC value as a function of coral sample assessed, prior to and following application of pluronic with or without Tween 80 to such samples FIG. 13 plots the SFUC value as a function of coral sample assessed, prior to and following application of absolute ethanol to such samples FIG. 14 plots the SFUC value as a function of coral sample assessed, prior to and following application of methylene blue to such samples.

In order to determine whether other amphiphilic compounds would provide the same results as that seen with tween in terms of increasing an SFUC value, pluronic (non-ionic tri-block copolymers composed of a central hydrophobic chain of polyoxypropylene (poly(propylene oxide)) flanked by two hydrophilic chains of polyoxypropylene) was applied to the samples, instead of tween, in accordance with the methods described hereinabove. As can be seen in FIG. 12, treatment with pluronic increased SFUC in essentially every sample tested (compare light grey bars with darker grey bars in FIG. 12). In most cases, applying both pluronic and tween 80 to the samples further increased the SFUC value obtained.

Figure 13:
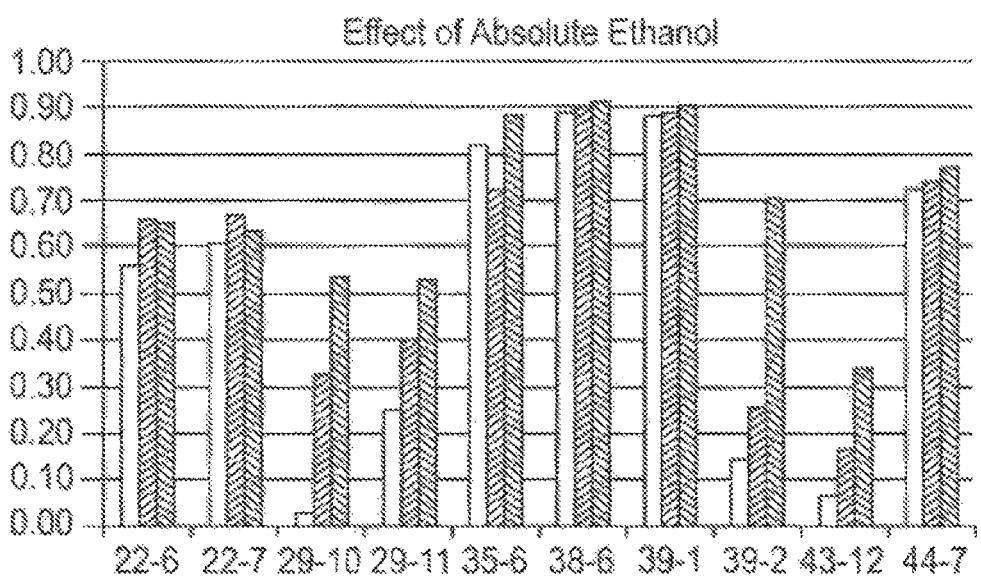

In order to determine whether polar solvents would provide the same results as that seen with tween in terms of increasing an SFUC value, absolute ethanol was applied to the samples. FIG. 13 demonstrates that as was seen with tween and pluronic, when ethanol was applied a large number of the samples evaluated showed an increase in SFUC, although in this case, the increase was less substantial when samples with an initial SFUC of more than 70% were evaluated.

Figure 14:
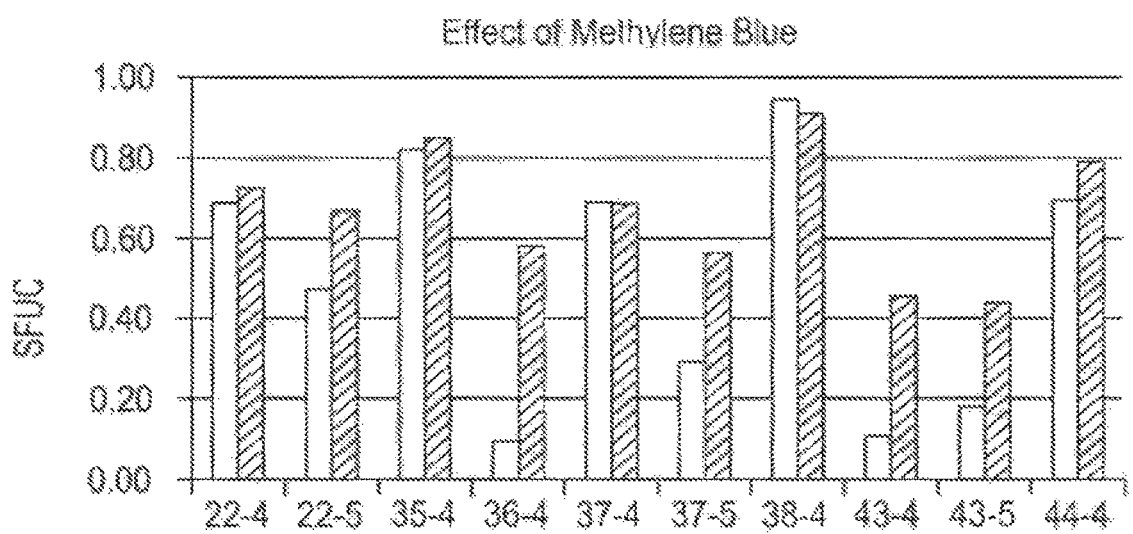

In order to determine whether cationic compounds would provide the same results as that seen with tween in terms of increasing an SFUC value, samples were exposed to methylene blue, similarly to that described for Tween 80 in the methods section hereinabove. As can be seen in FIG. 14, indeed application of methylene blue to samples paralleled the phenomenon observed with ethanol somewhat, in that the greater increases were found with samples having an SFUC value of less than 30%.

Figure 15:
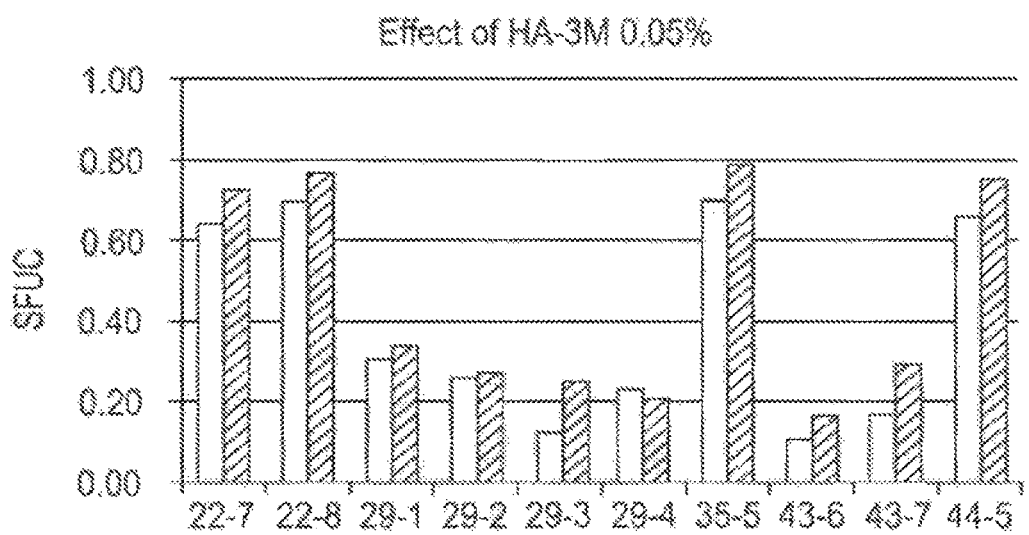
FIG. 15 plots the SFUC value as a function of coral sample assessed, prior to and following application of hyaluronic acid to such samples.

In order to determine whether anionic compounds would provide the same results as that seen with tween in terms of increasing an SFUC value, samples were exposed to hyaluronic acid, similarly to that described for Tween 80 in the methods section hereinabove. As can be seen in FIG. 15, indeed application of hyaluronic acid to samples increased SFUC values in most samples evaluated, however, such increases were more modest than that assessed for Tween 80.

Figure 16:
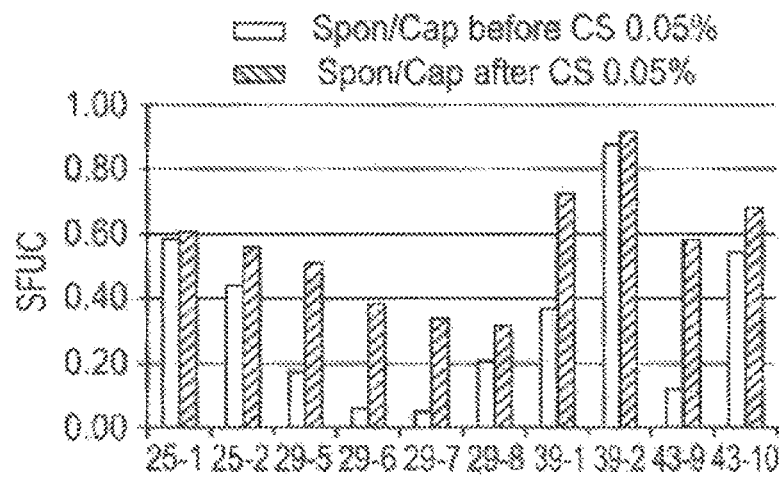
FIG. 16 plots the SFUC value as a function of coral sample assessed, prior to and following application of chondroitin sulfate to such samples.

Similarly, as can be seen in FIG. 16, when chondroitin sulphate was used, an increase in SFUC was evident in each sample.

To further the results reported hereinabove, a series of implants exhibiting a specific fluid uptake capacity value of at least 75% (n=42) from 3 different coral slabs (R-76, R-77, R-78) were subjected to a purification process, as follows: samples were immersed in a 5% NaOCl (W/W) solution at a ratio of 1:20 (plug volume:NaOCl) for 30 minutes under an applied negative pressure of at least 0.03 bar, after which the liquid was decanted and samples were exposed to applied negative pressure of at least 0.03 bar for 30 additional minutes. Samples were then immersed and immersed in 10% (W/W) $H_2O_2$ solution at a ratio of 1:20 (plug volume:$H_2O_2$) under an applied negative pressure of at least 0.03 bar for 15 minutes, after which the liquid was decanted and samples were exposed to applied negative pressure of at least 0.03 bar for 30 additional minutes. Samples were washed repeatedly in water, followed by being immersed in sterile water at a ratio of 1:20 (plug volume:H2O) and then exposed to applied negative pressure of at least 0.03 bar for 30 additional minutes. The wash step was repeated at least three times. Samples were then dried under a vacuum pressure of 0.03 bar for at least 4 to 6 hours. The specific fluid uptake capacity value was then ascertained for representative samples.

Figure 17:
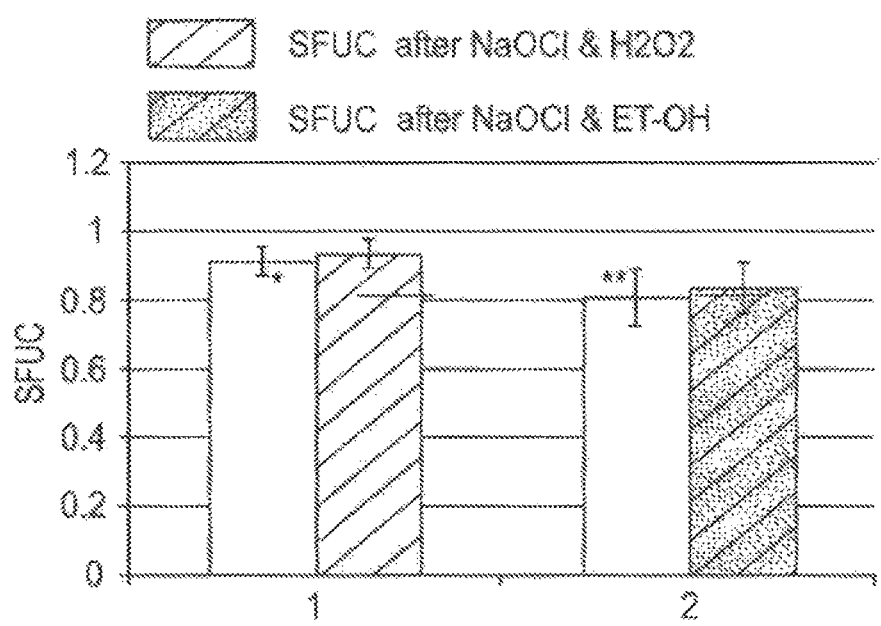
FIG. 17 plots the SWC values of implants from two samples (a first evaluating (n=13) and the second evaluating (n=15) corals) successively exposed to purification chemicals: hypochlorite and hydrogen peroxide and followed by an absolute ethanol extraction. *P<0.05; **P<0.01.

Samples were then immersed in absolute ethanol at a ratio of 1:10 (plug volume:ethanol) under vacuum conditions of at least 0.03 bar for 30 minutes, followed by decanting of the solution, and washes in sterile water as described in the previous paragraph. The specific fluid uptake capacity value (SWC) was then ascertained for representative samples and the results are provided in FIG. 17, showing the average SWC values of the indicated samples. As is evident from the figure, the SWC value improved in a statistically significant manner when the basic cleaning protocol was followed by an extraction step with a polar solvent, in this case, ethanol.

Figure 18:
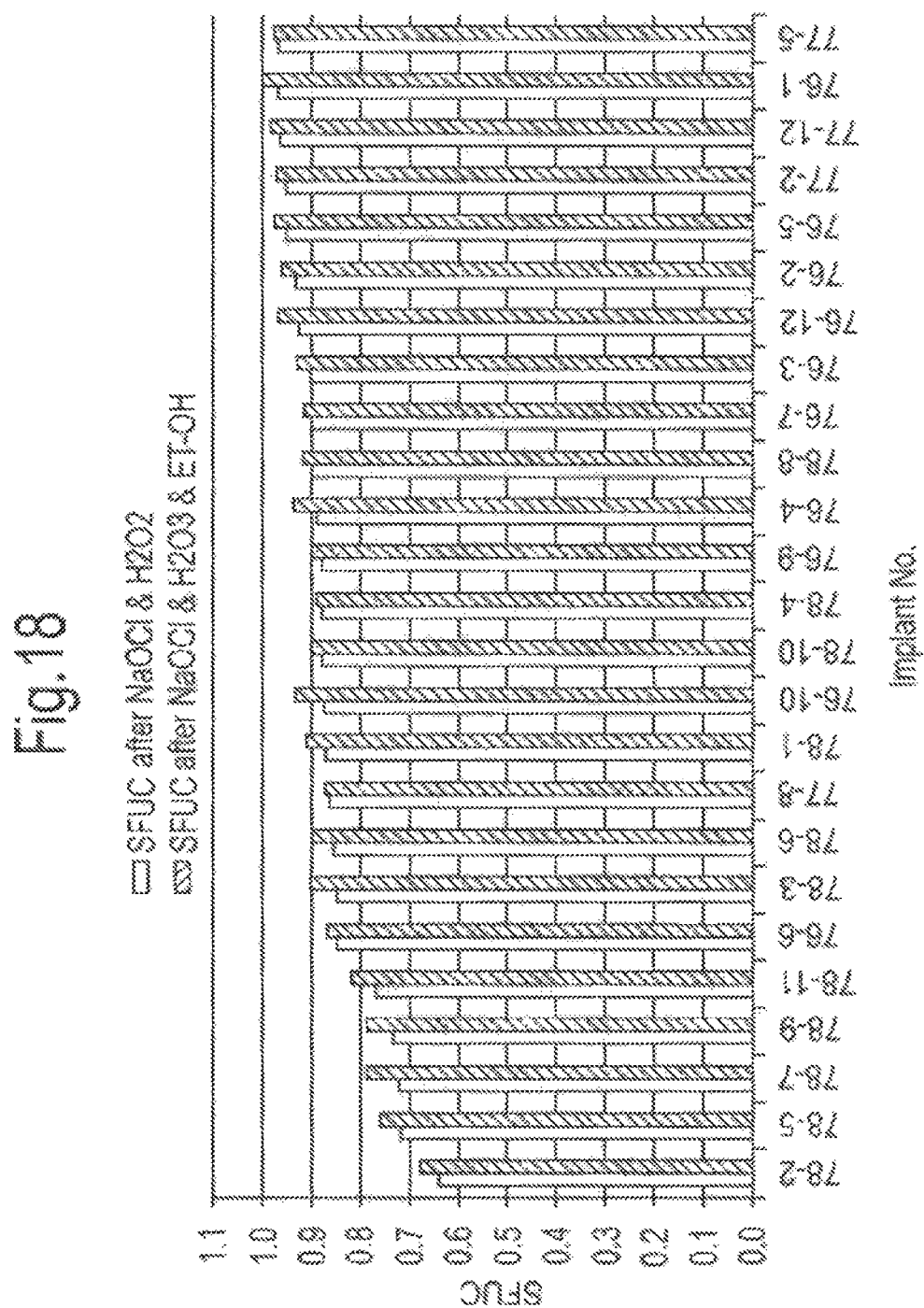
FIGS. 18 and 19 similarly plot the average SWC values for implants exposed to the purification step and following an ethanol extraction step.
Figure 19:
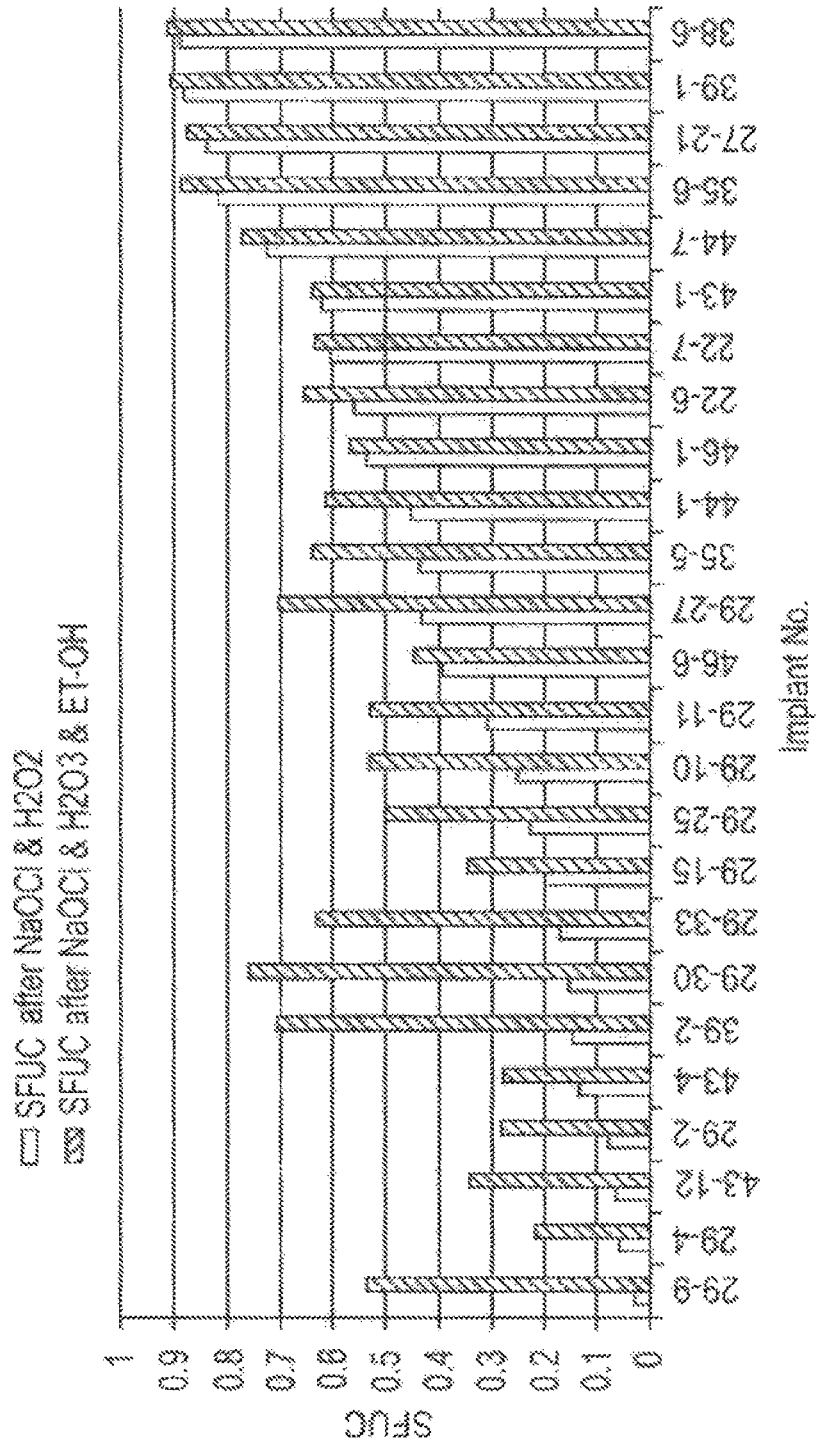
Figure 20A:
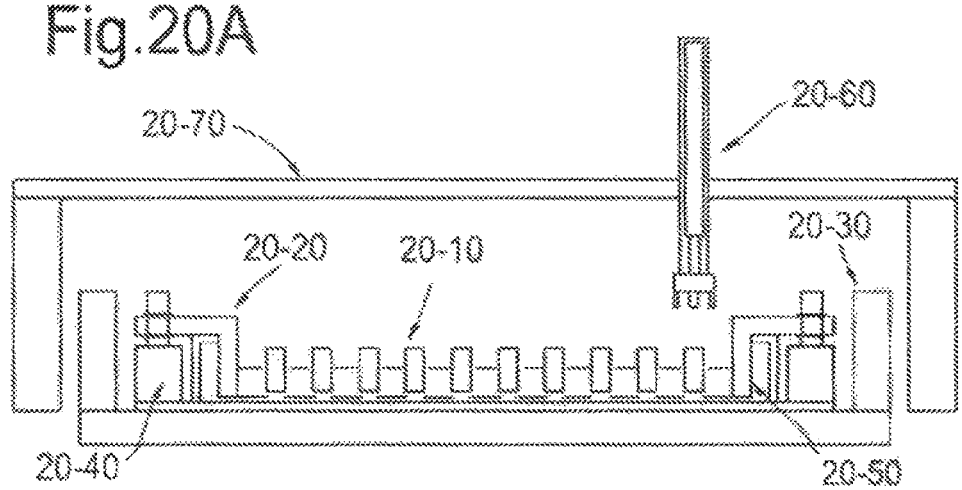
FIGS. 20A and 20B schematically depict an embodied automated apparatus of this invention in side and top view.
Figure 20B:
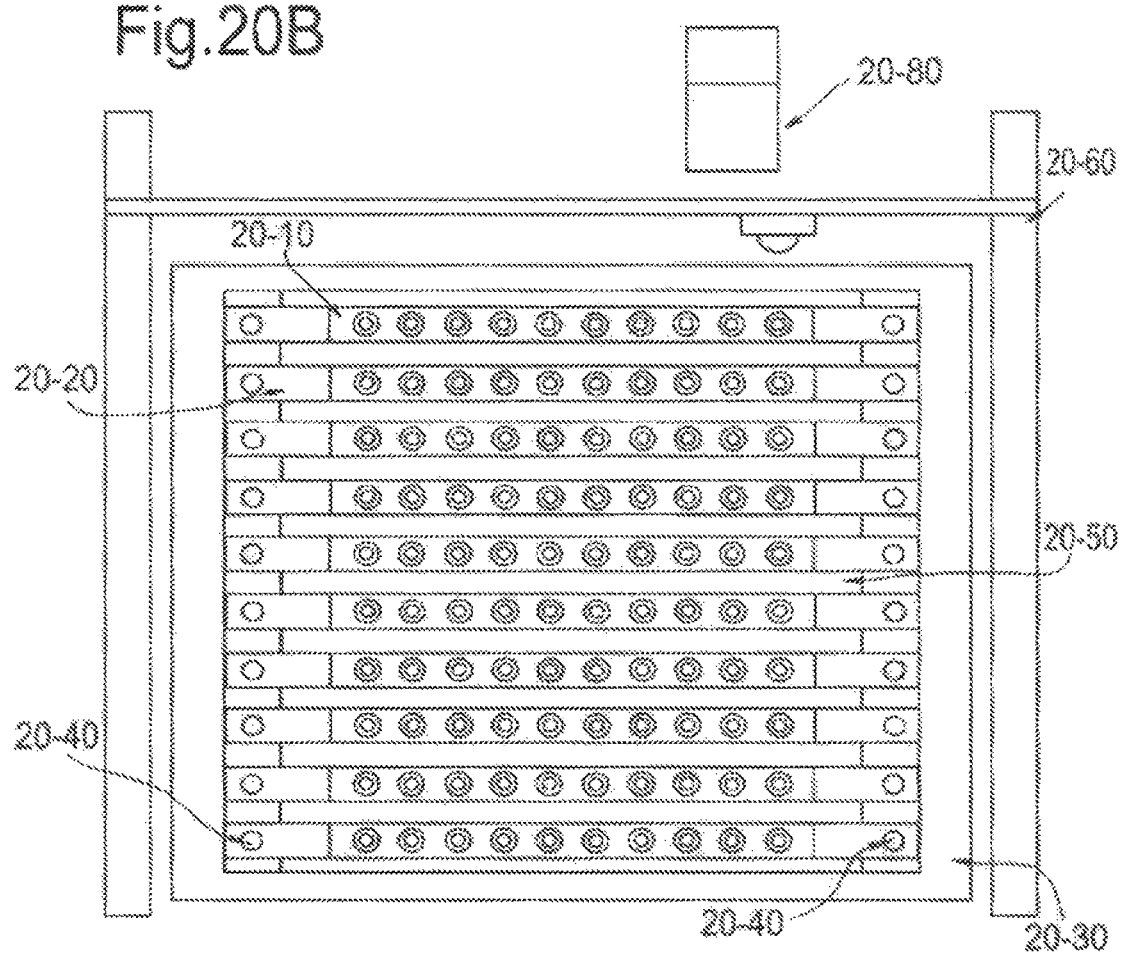

FIGS. 18-19 show the average SWC values obtained for numerous samples, before and after an ethanol extraction step applied following the basic isolation/processing step. As is clear from the myriad of samples assessed, unexpectedly, the specific fluid uptake capacity value is increased following the basic isolation/processing step, when an extraction step is executed using a polar solvent, such as ethanol.

Example 8

Automated Process and Apparatus for Isolating and Preparing Optimized Marine Organism Skeletal Derivative-Based Solid Substrates Coral samples of the hydrocoral *Porites lutea* are isolated as described in Example 1 and implants are prepared. The implants 20-10 are placed in the holding cassette 20-20, and the cover 20-70 is placed on the device. Negative pressure is applied via the vacuum 20-30 for a prescribed period of time, until the implants are fully dry and then the application is halted. The apparatus then individually weighs each implant to establish a dry weight. An automated cycle is initiated, which facilitates filling and a desired fluid level is maintained during the process. The cassettes 20-20 are individually raised and lowered into a first fluid level, via the cassette manipulator 20-40 within the fluid to enable spontaneous fluid uptake, and the implant manipulator 20-60 individually orients/moves the individual implants for weight determination, to determine the spontaneous fluid uptake value followed by optionally a pass of each implant past a drying/blotting station. The individual implants are all weighed and returned to their place within the cassettes. The cassettes 20-20 are then again individually raised and lowered into a second, significantly higher fluid level, via the cassette manipulator 20-40 within the excess fluid to facilitate full immersion of the implants, and negative pressure is applied again via the vacuum 20-30 for a defined period of time, ensuring maximum fluid uptake within each implant. The implant manipulator 20-60 again individually orients/moves the individual implants for a second weight determination, which provides the total fluid uptake value. The data processing unit of the apparatus determines and provides an output of the specific fluid uptake value, optionally specifically identifying which samples are to be selected based on indicated criteria.

It will be understood that the dimensions of the cassette will be constructed to accommodate implants of varying size. The apparatus can be built to scale, as well, to accommodate a larger or smaller number of cassettes, and the materials will be appropriate for the various fluids being assessed for their uptake within the stated implants. Sensors and appropriate relays are incorporated to, for example, provide a warning system in case of malfunction and the apparatus may further comprise a data processing unit, to calculate the specific fluid uptake capacity value from the determined spontaneous and total fluid uptake values obtained. Statistical analysis may also be included as part of the data processing package provided optionally with the claimed apparatuses of this invention.

Example 9

Improved Cell Adhesion and Viability with Optimized Marine Organism Skeletal Derivative-Based Solid Substrates Materials and Methods Human Embryonic Palatal Mesenchyme (HEPM) cells were grown in appropriate growth medium.

Implants of optimized (having a specific fluid uptake capacity value of more than 75%) and nonoptimized coral (having a specific fluid uptake capacity value of less than 60%) of each coral were seeded with HEPM cells at a density of $1.65 \times 10^4$ and $0.8 \times 10^4$ cells/10 µl, respectively, by incubating the cells with the scaffold for 15 min at 37° C., followed by the addition of more medium and further incubation for up to 7 days. Growth medium was replaced every 2 days.

Scaffolds containing cells were fixed in 4% formaldehyde, washed and dried via ethanol gradient solutions, and HMDS gradient solutions, then assessed by SEM.

Cell attachment and morphology was observed by SEM at day 1, 3, and 7 post seeding, following fixation.

Cell viability was assessed with an alamarBlue® metabolic assay, following the manufacturer's protocol. Samples were taken at day 1 and 7 post seeding. Fluorescence was evaluated at 544 nm and 590 nm (excitation and emission, respectively) using Fluoreskan ascent, a microplate fluorescence reader (Labotal), data in triplicates.

F fresh 200 l alamarBlue® containing medium (1:10 respectively) was added to each scaffold and incubate for 18 more hours (total of 24 hours).

Results

Cell attachment was found as early as 1 day post seeding in all samples evaluated, where optimized (opt), i.e. having a specific fluid uptake capacity value of more than 75%, and nonoptimized (nonopt), i.e. having a specific fluid uptake capacity value of less than 60%, as evaluated by SEM analysis.

Figure 21A:
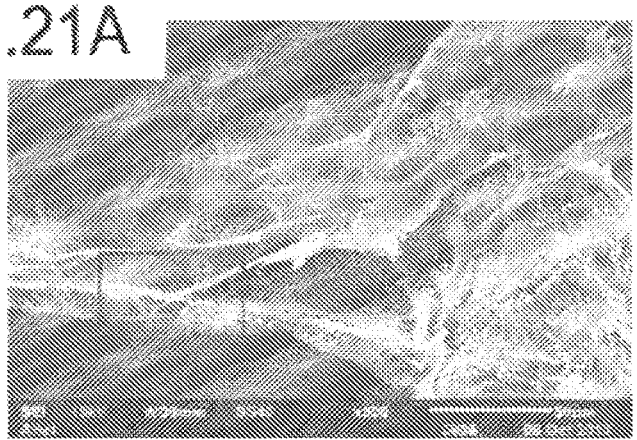
FIGS. 21A-21C present scanning electron micrographs of cell adhesion to coral substrates having a low specific fluid uptake capacity value (FIG. 21A and FIG. 21B) versus a high specific fluid uptake capacity value (FIG. 21C).
Figure 21B:
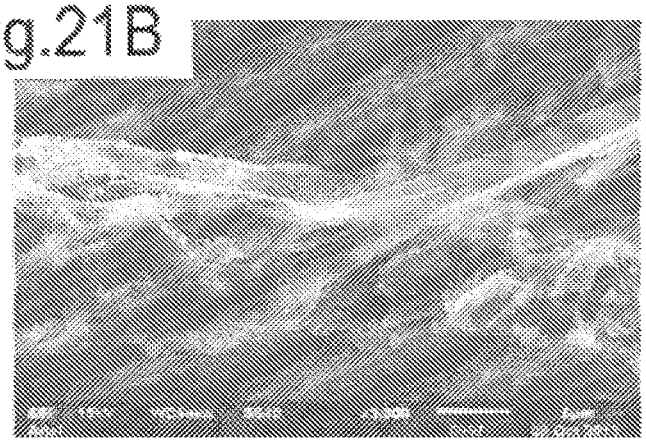

Non-optimized samples, having a specific fluid uptake capacity value of 26% showed that the cells adhered to the coral, with visible cell extensions (pods) proximally located the coral surface (FIG. 21A). Although cellular extensions make contact with coral substrate, the majority of the cell body does not seem to readily make contact. FIG. 21B presents a higher magnification of the "boxed" area in FIG. 21A, showing contact of the terminal cellular extensions with the coral, but the cell is not flattened or in full contact over its entire cell body with the coral.

Figure 21C:
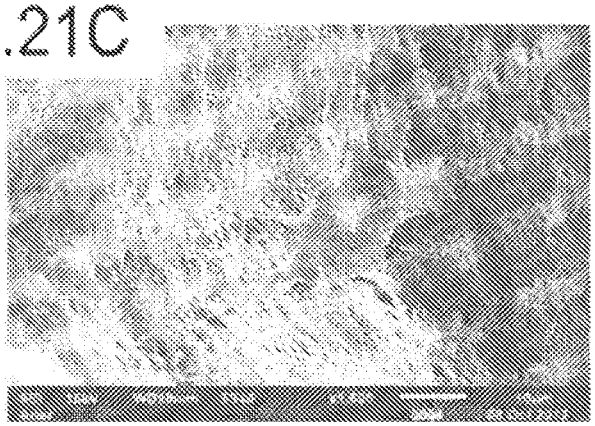

In marked contrast, optimized samples, having a specific fluid uptake capacity value of 95% showed that the cells adhered well to the coral, including full cell body spread over the coral (FIG. 21C).

Figure 22A:
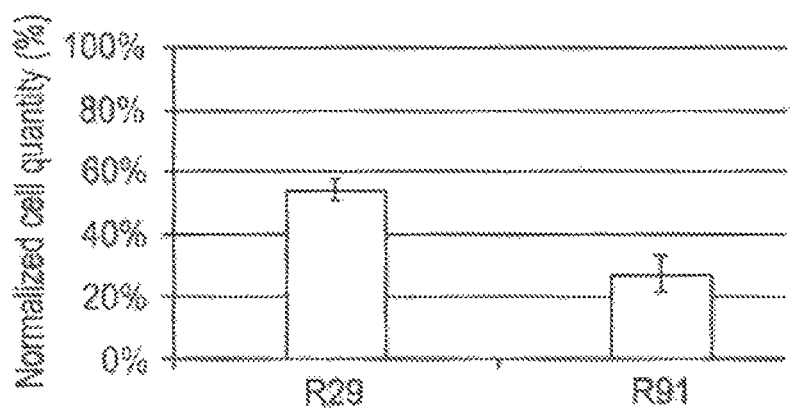
FIGS. 22A-22B graphically depict the HEPM cell proliferation and viability values as determined by alamarBlue® assay in samples having a low versus high specific fluid uptake capacity value.
Figure 22B:
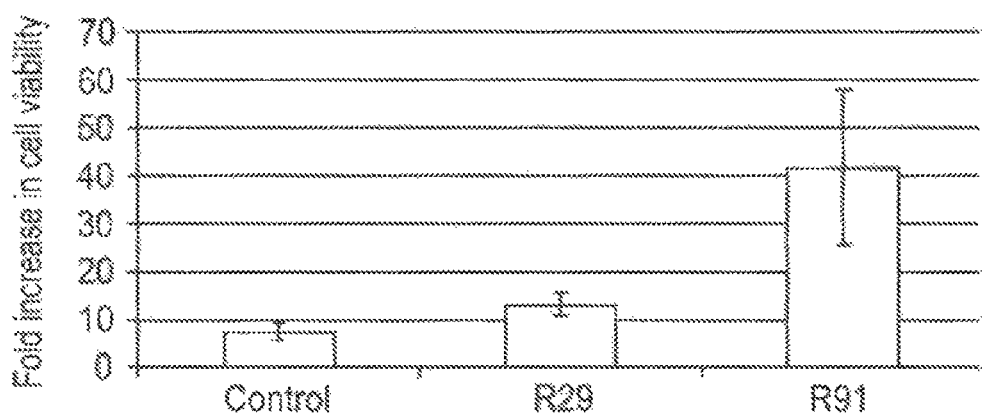

HEPM cells seeded on non-opt and opt coral samples were assessed by alamarBlue® assay, which quantitates the proliferation of various human and animal cell lines. At 1 day post seeding, values are normalized to those obtained for cultures of cells seeded on a polystyrene well, alone. 100% is determined as the cell viability value on the polystyrene well at day 1 (FIG. 22A). FIG. 22B represents HEPM cell viability on the various corals 7 days post seeding. In each coral, the values of the 7-day were divided by the values of the 1-day, so that the fold increase in cell viability is shown. As is readily appreciated, optimized samples yielded a significantly increased cell viability value compared to non-optimized samples. The HEPM cell viability increased with an average of 42 times higher in day 7 compared to day 1, whereas the increases in the low SWC coral R29 and the control group were only 13 and 7 times, respectively.

Taken together, the cell adhesion and cell viability assays demonstrate that samples considered to be optimized for fluid uptake promote greater full cell adherence and viability over time.

Example 10

Crystalline Form Association with the Isolation and Processing of Implants to Yield Optimized Marine Organism Skeletal Derivative-Based Solid Substrates

Materials and Methods

Coral samples were isolated and prepared in accordance with the methods described for Example 1. Samples were stained according to the protocol as described in [Chemical staining methods used in the identification of carbonate minerals, Tamer AYAN, Mineral Research and Exploration Institute of Turkey http://www.mta.gov.tr/v2.0/eng/dergi_pdf/65/11.pdf]. Briefly, Feigl solution is prepared according to standard methods. The coral samples are then stained with Feigl solution, and samples previously assessed for their specific fluid uptake capacity value are stained therewith. In this case, 2 samples as assessed in Example 9, a Sample R91, having a specific fluid uptake capacity value of 95%, and a Sample R48, having a specific fluid uptake capacity value of 42% were assessed.

Results

Corals are composed mainly of calcium carbonate (~98%). The calcium carbonate can be in different crystalline forms such as aragonite and calcite. Coral polyps may secrete an aragonite skeleton beneath their basal ectoderm forming a complex exoskeleton, which represents a chronological layered archive. In some regions, the aragonite structure dissolves and calcite or micrite is formed, usually at a later stage, by a process known as Diagenesis.

Figure 23A:
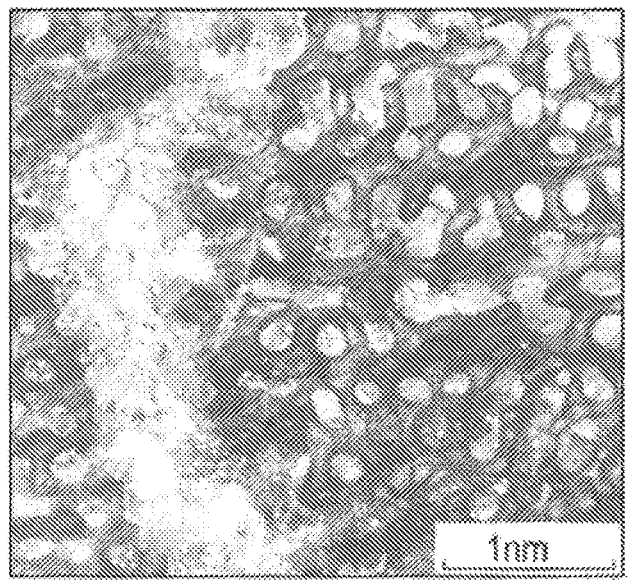
Figure 23B:

It has been shown that more calcite precipitates are found in ancient corals (Miocene epoch) compared to modern corals. FIG. 23A shows Miocene coral stained with Feigl solution, where the black region represents the aragonite crystalline structure. FIG. 23B shows a coral stained by Feigl staining, when no aragonite was present in the sample since no black color is observed [Both figures are taken from Diagenesis of growth bands in fossil scleractinian corals: identification and modes of preservation, Reuter et al. Facies (2005), 51: 146-159, which reference is fully incorporated herein in its entirety].

Feigl's solution stains aragonite black. When coral samples are viewed macroscopically, in the absence of aragonite in a given sample, the sample will appear white or gray in color.

It was therefore of interest to determine whether the crystal structure correlated with the specific fluid uptake capacity value and whether the optimization processes herein were impacted in terms of the Feigl staining protocol. Toward this end, coral samples R91 and R48 were assessed for their specific fluid uptake capacity value, including a first macroscopic evaluation of uptake of goat blood, and subjected to further processing, including an ethanol extraction step as described in Example 7.

FIGS. 23C-23F present the results of analysis of essentially identical samples taken from R91 and R48, both prior to and following an ethanol further purification step. Whereas the gross pattern of Feigl staining approximated that of the uptake of blood in each respective sample (compare FIG. 23C versus FIG. 23D and FIG. 23E versus FIG. 23F), the staining patterns are not identical. Moreover, as is more readily observed when comparing samples of R48 before and after ethanol treatment, increased blood uptake and Feigl positive staining was observed, indicating greater optimization of the samples, when subjected to a described further processing step.

Taken together, it appears that samples enriched for aragonite versus non-aragonite are more readily associated with a higher specific fluid uptake capacity value, spontaneous blood absorption and black stain using Feigl solution, which can be further improved by the specific further processing steps, as herein described.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value. In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A process of promoting cartilage and/or bone repair or repair of an osteochondral defect, the process comprising implanting, in a subject, a solid substrate within a site in need of cartilage and/or bone repair, or in need of repair of an osteochondral defect,
    wherein the solid substrate is a marine organism skeletal derivative-based solid material that comprises a coral or a coral-based derivative,
    and wherein the specific fluid uptake capacity of the solid substrate is at least 75% when the specific fluid uptake capacity is determined by establishing the spontaneous fluid uptake value in water, establishing the total fluid uptake value in water under pressure, and dividing the spontaneous fluid uptake value by the total fluid uptake value.

2. The process of claim 1, wherein the marine organism skeletal derivative-based solid material comprises the coral-based derivative.

3. The process of claim 2, wherein the coral-based derivative comprises aragonite, calcite, mixtures thereof, or other polymorphs of the same.

4. The process of claim 2, wherein the coral-based derivative comprises aragonite, calcite, hydroxyapatite, or a combination thereof.

5. The process of claim 1, wherein the marine organism skeletal derivative-based solid material comprises a bone filler or bone substitute material.

6. The process of claim 1, wherein the marine organism skeletal derivative-based solid material comprises a biocompatible polymer.

7. The process of claim 6, wherein the biocompatible polymer is incorporated within voids or pores in the solid substrate or wherein the biocompatible polymer is attached to an outer surface of the solid substrate.

8. The process of claim 6, wherein the biocompatible polymer comprises a natural polymer comprising a glycosaminoglycan, collagen, fibrin, elastin, silk, chitosan, alginate, and any combination thereof.

9. The process of claim 8, wherein the biocompatible polymer comprises a glycosaminoglycan and the glycosaminoglycan is hyaluronic acid, sodium hyaluronate, cross linked hyaluronic acid, or a combination thereof.

10. The process of claim 1, wherein the marine organism skeletal derivative-based solid material further comprises a cytokine, a growth factor, a therapeutic compound, an osteoinductive agent, a bioactive glass, a bone filler, a bone cement, a drug, or any combination thereof, wherein the therapeutic compound or drug comprises an anti-inflammatory compound, an anti-infective compound, a pro-angiogenic factor or a combination thereof.

11. The process of claim 1, wherein the marine organism skeletal derivative-based solid material approximates the form of a cylinder, cone, tac, pin, screw, rectangular bar, plate, disc, pyramid, granule, powder, coral sand, condyle, rib, pelvis, vertebra, bone, cartilaginous tissue, ball or cube.

12. The process of claim 1, wherein the marine organism skeletal derivative-based solid material approximates a shape that accommodates a site of desired tissue growth or repair.

13. The process of claim 1, wherein the marine organism skeletal derivative-based solid material comprises a hollow or hollows along a Cartesian coordinate axis of the solid material.

14. The process of claim 1, wherein the process further comprises the step of contacting the marine organism skeletal derivative-based solid material with cells or tissue.

15. The process of claim 14, wherein the process comprises contacting the marine organism skeletal derivative-based solid material with cells and the cells comprise stem or progenitor cells or a combination thereof.

16. The process of claim 1, wherein the subject is a human subject.

17. The process of claim 1, wherein the subject is a veterinary subject.

18. The process of claim 1, wherein the subject is afflicted with a defect or disorder or disease of the cartilage or bone or a combination thereof.

19. The process of claim 18, wherein the cartilage defect or disorder or disease comprises a full or partial thickness articular cartilage defect; osteochondral defect; osteoarthritis, a joint defect or a defect resulting from trauma, sports, or repetitive stress.

20. The process of claim 18, wherein the defect or disorder or disease of the bone comprises a fracture, bone defect, bone edema, osteoporosis, bone tumor, bone cyst, or a defect resulting from trauma, sports, or repetitive stress.

21. The process of claim 1, wherein the marine organism skeletal derivative-based solid material contains ground particles derived from the coral-based derivative, suspended in a biocompatible matrix or further comprises a bone filler or bone substitute material.

22. The process of claim 21, wherein the biocompatible matrix is a hydrogel.

* * * * *